United States Patent
Ma et al.

(10) Patent No.: US 11,495,748 B2
(45) Date of Patent: Nov. 8, 2022

(54) ORGANIC COMPOUND HAVING ADAMANTYL FLUORENE LIGANDS ON 1,3,5-TRIAZINE AND ELECTRONIC DEVICE

(71) Applicant: Shaanxi Lighte Optoelectronics Material Co., Ltd., Xi'an (CN)

(72) Inventors: Tiantian Ma, Xi'an (CN); Kongyan Zhang, Xi'an (CN); Jiamei Cao, Xi'an (CN)

(73) Assignee: SHAANXI LIGHTE OPTOELECTRONICS MATERIAL CO., LTD., Shaanxi (CN)

( * ) Notice: Subject to any disclaimer, the term of this patent is extended or adjusted under 35 U.S.C. 154(b) by 0 days.

(21) Appl. No.: 17/623,355

(22) PCT Filed: Sep. 15, 2020

(86) PCT No.: PCT/CN2020/115338
§ 371 (c)(1),
(2) Date: Dec. 28, 2021

(87) PCT Pub. No.: WO2021/057550
PCT Pub. Date: Apr. 1, 2021

(65) Prior Publication Data
US 2022/0216420 A1 Jul. 7, 2022

(30) Foreign Application Priority Data
Sep. 25, 2019 (CN) .......................... 201910911675.4

(51) Int. Cl.
*C07D 251/24* (2006.01)
*H01L 51/00* (2006.01)
(Continued)

(52) U.S. Cl.
CPC ........ *H01L 51/0067* (2013.01); *C07D 251/24* (2013.01); *C07D 401/10* (2013.01);
(Continued)

(58) Field of Classification Search
CPC ............. H01L 51/0067; H01L 51/0056; H01L 51/0058; H01L 51/0072; H01L 51/0073;
(Continued)

(56) References Cited

U.S. PATENT DOCUMENTS

2016/0372678 A1* 12/2016 Arai .................... H01L 51/0072
2022/0017544 A1* 1/2022 Yoon .................... H01L 51/006

FOREIGN PATENT DOCUMENTS

| CN | 110128279 A | 8/2019 |
|---|---|---|
| CN | 110615759 A | 12/2019 |

(Continued)

OTHER PUBLICATIONS

International Search Report from corresponding International Application No. PCT/CN2020/115338, dated Nov. 18, 2020, 5 pages.

*Primary Examiner* — Michael Jung
(74) *Attorney, Agent, or Firm* — Tucker Ellis LLP

(57) ABSTRACT

The present disclosure provides an organic compound and an electronic device containing the organic compound, which relates to the technical field of organic materials. The structure of the organic compound is as shown in the following Chemical formula (1), where Y has a structure as shown in the following formula (2) or (3). The organic compound is used in, for example, an electronic device of an organic electroluminescent device, and can improve the lifetime property and deficiency property, electrochemical (Continued)

stability and thermal stability, and reduce the driving voltage of the organic electroluminescent device.

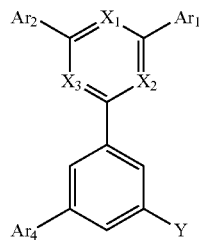

Chemical formula I

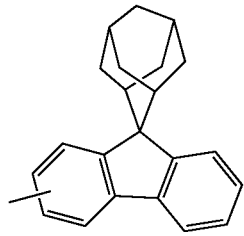

Formula (2)

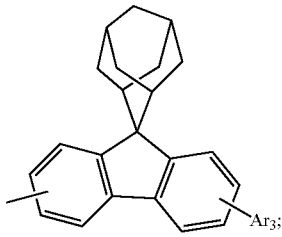

Formula (3)

(51) Int. Cl.
    *C07D 401/10*    (2006.01)
    *C09K 11/06*    (2006.01)
    *C07D 401/14*    (2006.01)
    *C07D 403/10*    (2006.01)
    *C07D 405/10*    (2006.01)
    *C07D 409/10*    (2006.01)
    *H01L 51/50*    (2006.01)

(52) U.S. Cl.
    CPC ......... *C07D 401/14* (2013.01); *C07D 403/10* (2013.01); *C07D 405/10* (2013.01); *C07D 409/10* (2013.01); *C09K 11/06* (2013.01); *H01L 51/0056* (2013.01); *H01L 51/0058* (2013.01); *H01L 51/0072* (2013.01); *H01L 51/0073* (2013.01); *H01L 51/0074* (2013.01); *C09K 2211/1018* (2013.01); *H01L 51/5072* (2013.01)

(58) Field of Classification Search
    CPC . H01L 51/0074; C07D 251/24; C07D 401/10; C07D 405/10; C07D 409/10; C09K 11/06
    See application file for complete search history.

(56) References Cited

FOREIGN PATENT DOCUMENTS

| | | | | |
|---|---|---|---|---|
| CN | 111018797 | A | 4/2020 | |
| CN | 111039881 | A | 4/2020 | |
| CN | 111138298 | A | 5/2020 | |
| CN | 111377853 | A | 7/2020 | |
| WO | WO-2015005351 | A1 * | 1/2015 | ........... C07C 309/06 |
| WO | 2020046049 | A1 | 3/2020 | |

* cited by examiner

7 Claims, 1 Drawing Sheet

ORGANIC COMPOUND HAVING ADAMANTYL FLUORENE LIGANDS ON 1,3,5-TRIAZINE AND ELECTRONIC DEVICE

CROSS-REFERENCING TO RELATED APPLICATIONS

The present application claims the priority of Chinese patent CN201910911675.4, filed on Sep. 25, 2019, the entirety of which is incorporated herein by reference.

TECHNICAL FIELD

The present disclosure relates to the technical field of organic materials, and specifically relates to an organic compound and an electronic device containing the organic compound.

BACKGROUND

In recent years, the organic electroluminescent device (OLED), as a new generation of display technology, has gradually come into people's vision. Common organic electroluminescent devices consist of an anode, a cathode, and more than one organic layers disposed between the cathode and the anode. When voltage is applied at both cathode and anode, an electric field is generated between the two electrodes; under the action of the electric field, electrons on the side of cathode move towards a light-emitting layer in an organic layer, and holes on the side of anode also move towards the light-emitting layer, then the electrons and the holes combine with each other to form excitons, and the excitons are in an excited state to release energy to the outside, thereby emitting light to the outside in the changing process of releasing energy to a ground state from the excited state. Therefore, it is crucial to improve the recombination between electrons and holes in the OLED device.

Generally, there exist problems, such as, increase of driving voltage, decrease of luminous efficiency and shortened lifetime during the process of driving an organic electroluminescent device at high temperature, thus leading to the performance decline of the organic electroluminescent device.

At present, even although a large number of organic electroluminescent materials with excellent performance have been developed successively, there are still lots of problems in the technology. Therefore, how to design a new material with better performance to render the device made therefrom to achieve the effects of voltage reduction, efficiency enhancement and lifetime improvement is always the problem to be solved by a person skilled in the art urgently.

SUMMARY

The objective of the present disclosure is to provide an organic compound and an electronic device containing the organic compound, thus solving one or more problems existing in the prior art.

According to an aspect of the present disclosure, an organic compound is provided, having a structure as shown in a chemical formula 1:

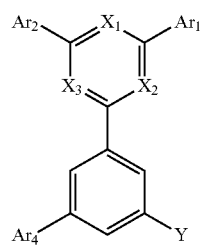

Chemical formula 1 wherein $X_1$, $X_2$ and $X_3$ are the same or different, and respectively represent C or N;

Y is

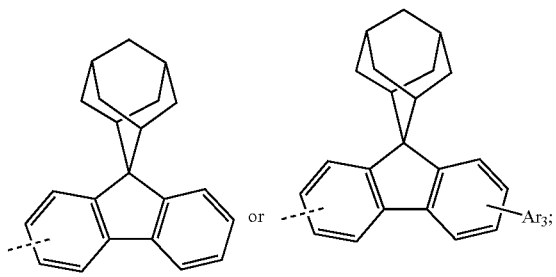

and $Ar_1$, $Ar_2$, $Ar_3$ and $Ar_4$ are the same or different, and are each independently selected from a substituted or unsubstituted alkyl with 1 to 35 carbon atoms, a substituted or unsubstituted alkenyl with 2 to 35 carbon atoms, a substituted or unsubstituted alkynyl with 2 to 35 carbon atoms, a substituted or unsubstituted cycloalkyl with 3 to 35 carbon atoms, a substituted or unsubstituted heterocycloalkyl with 2 to 35 carbon atoms, a substituted or unsubstituted aralkyl with 7 to 30 carbon atoms, a substituted or unsubstituted heteroaralkyl with 2 to 30 carbon atoms, a substituted or unsubstituted aryl with 6 to 30 carbon atoms, or a substituted or unsubstituted heteroaryl with 1 to 30 carbon atoms.

According to another aspect of the present disclosure, an electronic device is further provided, comprising a cathode, an anode and a functional layer located between the cathode and the anode; where the functional layer contains the above compound.

The compound of the present disclosure uses 2,4-diphenyl-1,3,5-triazine as the electron injection and transport group, and on this basis, introduces the core structure of adamantane-fluorenyl group; the group has an electron-rich characteristic to enhance the polarity of the whole molecule, which is beneficial to directional arrangement of material molecules, thereby enhancing the injection and transporting of electrons, and promoting the photoelectric conversion efficiency of the device. Meanwhile, the adamantane-fluorenyl group has a high molecular weight and steric-hinderance effect, which may effectively increase the glass-transition temperature of the material and inhibit the crystallization of the material, such that the material has longer lifetime in a photoelectric conversion device. As an electron transport layer material, the compound can improve the lifetime property, efficiency property, electrochemical stability and thermal stability and reduce the driving voltage of the organic electroluminescent device.

It should be understood that the above general description and detail description hereafter are merely exemplary and explanatory, but do not limit the present disclosure.

BRIEF DESCRIPTION OF THE DRAWINGS

Drawings here are incorporated into the description to constitute a part of the specifications, show the embodiments conforming to the present disclosure and are used to explain the principle of the present disclosure together with the description. Apparently, the drawings described below are merely some embodiments of the present disclosure. A person skilled in the art may further obtain other drawings according to these accompanying drawings without any inventive efforts.

In FIG. 1, 10: Anode; 20: Functional layer; 201: Hole injecting layer; 202: Hole transporting layer; 203: Electron blocking layer; 204: Light-emitting layer; 205: Hole blocking layer; 206: Electron transporting layer; 207: Electron injecting layer; 30: Cathode; 40: Capping layer;

In FIG. 2, 50: Anode; 60: Functional layer; 601: Hole transporting layer; 602: Photosensitive active layer; 603: Electron transporting layer; and 70: Cathode.

DETAILED DESCRIPTION

Figure 1:
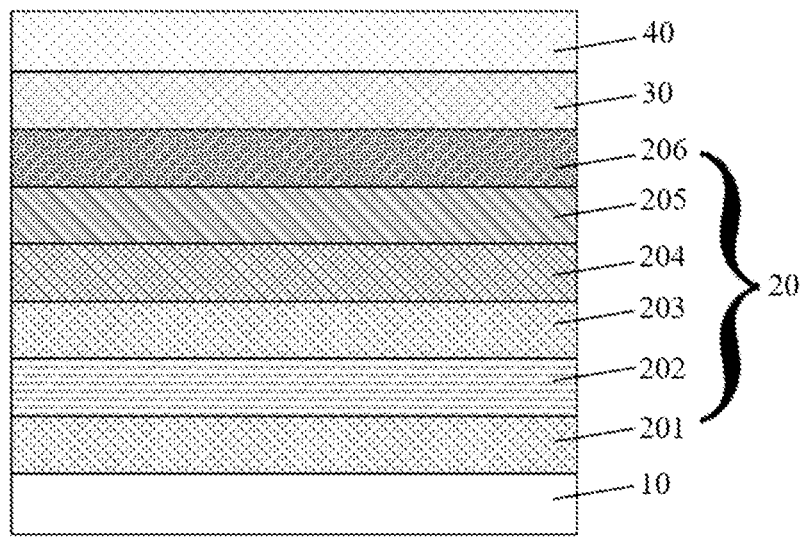
FIG. 1 is a structural schematic diagram of an organic electroluminescent device in an embodiment of the present disclosure.

Exemplary embodiments are now described more comprehensively. However, exemplary embodiments can be implemented in various forms, and should be not construed as being limited to the embodiments described here. On the contrary, these embodiments are provided to make the present disclosure more comprehensive and intact, and the idea of the exemplary embodiments will be comprehensively conveyed to the skilled in the art.

The present disclosure provides an organic compound, having a structure as shown in Chemical formula 1:

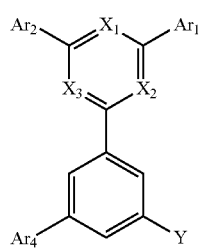

Chemical formula 1 wherein $X_1$, $X_2$ and $X_3$ are the same or different, and respectively represent C or N;

Y is

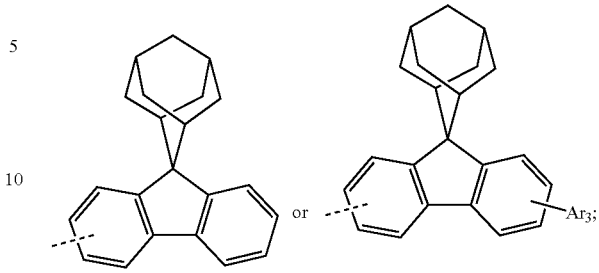

and
where the dotted line on the left of Y represents the linkage between any position on the left side of the benzene ring with

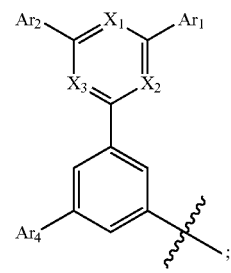

the connecting bond of $Ar_3$ represents the substitution $Ar_3$ at any position of the benzene ring on the right side.

$Ar_1$, $Ar_2$, $Ar_3$ and $Ar_4$ are the same or different, and are each independently selected from a substituted or unsubstituted alkyl with 1 to 35 carbon atoms, a substituted or unsubstituted alkenyl with 2 to 35 carbon atoms, a substituted or unsubstituted alkynyl with 2 to 35 carbon atoms, a substituted or unsubstituted cycloalkyl with 3 to 35 carbon atoms, a substituted or unsubstituted heterocycloalkyl with 2 to 35 carbon atoms, a substituted or unsubstituted aralkyl with 7 to 30 carbon atoms, a substituted or unsubstituted heteroaralkyl with 2 to 30 carbon atoms, a substituted or unsubstituted aryl with 6 to 30 carbon atoms, or a substituted or unsubstituted heteroaryl with 1 to 30 carbon atoms.

The aryl group may be a monocyclic aryl group or a fused cyclic aryl group, two monocyclic aryl groups conjugated via a carbon-carbon bond, a monocyclic aryl group and a fused cyclic aryl group conjugated via a carbon-carbon bond, and two fused cyclic aryl groups conjugated via a carbon-carbon bond. That is, two or more aromatic groups conjugated via a carbon-carbon bond may be regarded as the aryl group of the present disclosure. Among them, the aryl group does not contain heteroatoms such as B, N, O, S or P. The examples of the aryl group may include, but not limited to, phenyl, naphthyl, fluorenyl, anthracyl, phenanthryl, biphenyl, terphenylyl, benzo[9,10]phenanthryl, pyrenyl, benzofluoranthenyl, chrysenyl, and the like.

The substituted aryl refers that one or two or more hydrogen atoms in the aryl are substituted by groups such as, deuterium atom, halogen group, —CN, aryl, heteroaryl, alkyl, cycloalkyl, alkoxy and alkylthio. When a same atom has two substituents, optionally, the two substituents may be connected with each other to form a ring together with the atom to which they are jointly connected, for example, to form a saturated or unsaturated 5- to 15-membered ring. The group as a substituent of aryl, for example, may be phenyl, naphthyl, and biphenyl, etc. Specific examples of heteroaryl-substituted aryl include, but not limited to, dibenzofuryl-substituted phenyl, dibenzothienyl-substituted phenyl, pyridyl-substituted phenyl, carbazolyl-substituted phenyl, and the like. Furthermore, fluorenyl may be substituted, and the two substituents may be combined with each other to form a spiro structure. Specific examples of the substituted fluorenyl include, but not limited to, the following structures:

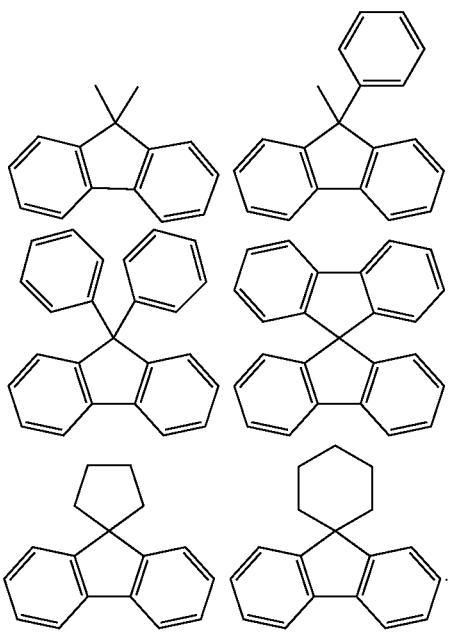

When there is no specific definition provided additionally, "hetero" refers that one functional group includes at least one heteroatoms such as B, N, O, S, or P, etc., and the rest are carbon and hydrogen.

The heteroaryl may be a monocyclic heteroaryl; a fused cyclic heteroaryl; two aromatic ring systems conjugated via a carbon-carbon bond and at least one of the aromatic ring systems contains a heteroatom, where the aromatic ring system may be a monocyclic aromatic ring system or a fused cyclic aromatic ring system. For example, the heteroaryl may include, but not limited to, thienyl, furyl, pyrryl, imidazolyl, thiazolyl, oxazolyl, pyridyl, pyrimidyl, triazinyl, acridinyl, pyridazinyl, pyrazinyl, quinolyl, quinazolinyl, quinoxalinyl, phenoxazinyl, phthalazinyl, pyridinopyrimidyl, pyridinopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuryl, phenanthrolinyl, isoxazolyl, thiadiazolyl, benzothiazolyl, phenothiazinyl, silicon-fluorenyl, dibenzofuryl, and N-arylcarbazolyl (e.g., N-phenylcarbazolyl), N-heteroarylcarbazolyl (e.g., N-pyridylcarbazolyl), N-alkylcarbazolyl (e.g., N-methylcarbazolyl), and the like. Among them, thienyl, furyl, phenanthrolinyl, and the like are heteroaryl groups of a single aromatic ring system; N-arylcarbazolyl and N-heteroarylcarbazolyl are heteroaryl groups of a polycyclic system conjugated via a carbon-carbon bond.

The substituted heteroaryl may refer that one or two or more hydrogen atoms in heteroaryl are substituted by groups such as deuterium atom, halogen group, aryl, heteroaryl, alkyl, cycloalkyl, alkoxy and alkylthio, etc. Specific examples of the aryl-substituted heteroaryl include, but not limited to, phenyl-substituted dibenzofuryl, phenyl-substituted dibenzothienyl, phenyl-substituted pyridyl, phenyl-substituted carbazolyl, and the like. The heteroaryl as a substituent may be, for example, pyridyl, dibenzofuryl, dibenzothienyl, carbazolyl, N-phenylcarbazolyl, and the like.

It should be noted that the ring-forming carbon atom refers to the number of carbon atoms located on the aromatic rings of aryl and heteroaryl. For example, the ring-forming carbon atoms of naphthyl is 10, the ring-forming carbon atoms of biphenyl is 12, the ring-forming carbon atoms of dibenzofuryl is 12, the ring-forming carbon atoms of phenyl-substituted dibenzofuryl is 18, and the ring-forming carbon atoms of N-phenylcarbazolyl is 18.

In the present disclosure, the descriptions used "each . . . independently", " . . . respectively independently" and " . . . independently selected from" may be exchanged with each other, and should be understood in broad sense, which means that specific items expressed between identical symbols in different groups are not influenced with each other, or means that specific items expressed between identical symbols in the same group are not influenced with each other.

The term "optional" or "optionally" means that the subsequently described incident or environment may, but need not occur; which includes the occasion where the incident or environment occurs or does not occur. For example, the expression "optionally, two adjacent substituents xx form a ring" means that such two substituents may, but not inevitably, form a ring, which includes the occasion where two adjacent substituents form a ring and two adjacent substituents do not form a ring.

In the present disclosure, the non-locating linking bond involved refers to a single bond " -§- " stretching out of the cyclic system, indicating that one end of the linking bond may be linked to any position of the cyclic system penetrated by the bond, and another end is linked with the rest part of the compound molecule.

For example, as shown in Formula (f) below, the naphthyl denoted by Formula (f) is linked with other positions of the molecule via two non-locating linking bonds penetrating the dual rings, and the meaning includes any possible linking mode as shown in Formulas (f-1)-(f-10).

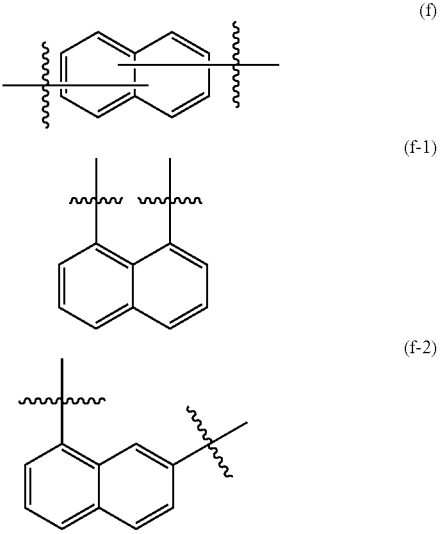

(f-3) 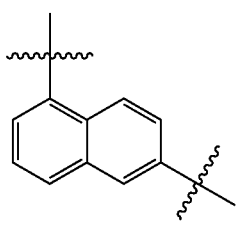
(f-4) 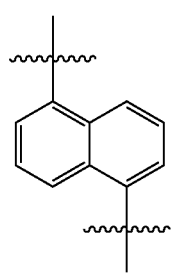
(f-5) 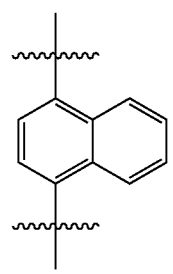
(f-6) 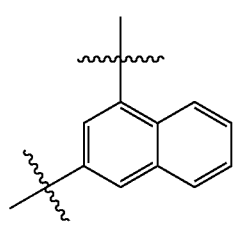
(f-7) 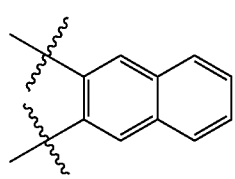
(f-8) 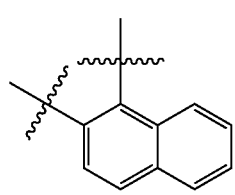
(f-9) 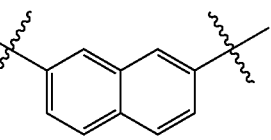
(f-10) 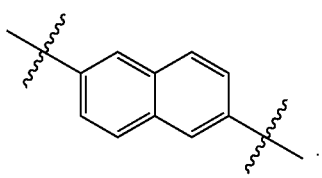
For another example, as shown in Formula (X') below, the phenanthryl denoted by Formula (X') is linked with other positions of the molecule via a non-locating linking bond stretching from the middle part of one side of the benzene ring, and the meaning includes any possible linking mode as shown in Formulas (X'-1)-(X'-4).
(X') 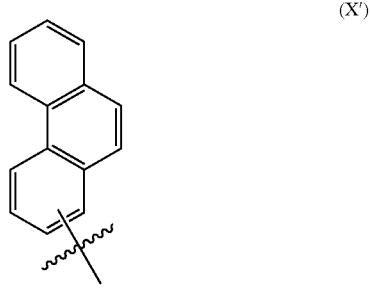
(X'-1) 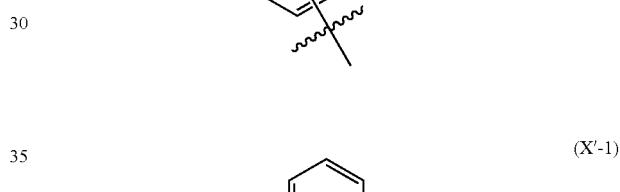
(X'-2) 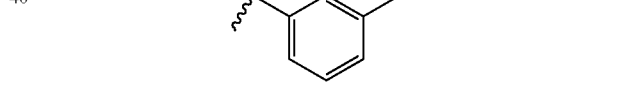
(X'-3) 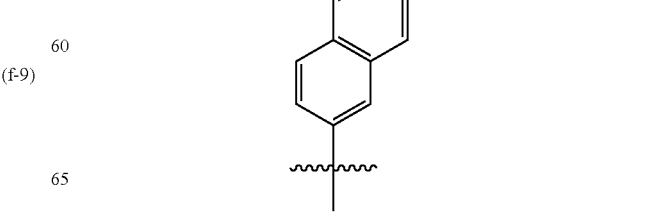

-continued (X'-4)

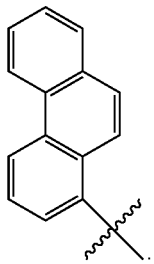

In the present disclosure, the alkyl may be, for example, an alkyl with 1 to 10 carbon atoms, and specifically may include a linear alkyl with 1 to 10 carbon atoms and a branched alkyl with 3 to 10 carbon atoms. The carbon number may be specifically 1, 2, 3, 4, 5, 6, 7, 8, 9 or 10. Specific examples of the alkyl include, but not limited to, methyl, ethyl, n-propyl, isopropyl, n-butyl, isobutyl, tert-butyl, n-pentyl, isopentyl, neo-pentyl, cyclopentyl, n-hexyl, heptyl, n-octyl, 2-ethylhexyl, nonyl, decyl, 3,7-dimethyloctyl, and the like.

Halogen group may include F, I, Br, Cl, and the like.

As a substituent, the carbon number of aryl may be 6 to 33. For example, the carbon number may be 6 (phenyl), 10 (naphthyl), 12 (e.g., biphenyl), 14, 15, 16, 20 or 25; and the carbon number may be selected from any range consisting of the preceding numerical values.

As a substituent, the carbon number of heteroaryl may be 1 to 33, for example, the carbon number may be 5 (e.g., pyridyl), 8, 12 (e.g., dibenzofuryl, dibenzothienyl or carbazolyl), 15, 18 (e.g., N-phenylcarbazolyl), and the like; the carbon number may be further selected from any range consisting of the preceding numerical values.

As a substituent, the carbon number of cycloalkyl may be 3 to 10, and specific examples of cycloalkyl include, but not limited to, cyclopentyl, cyclohexyl, adamantyl, and the like.

As a substituent, arylamino refers to a group formed by substituting one or two hydrogen atoms in amino (—NH$_2$) with aryl, where the aryl may be, for example, phenyl, naphthyl, biphenyl, and the like. Specific examples of arylamino include, but not limited to the following groups:

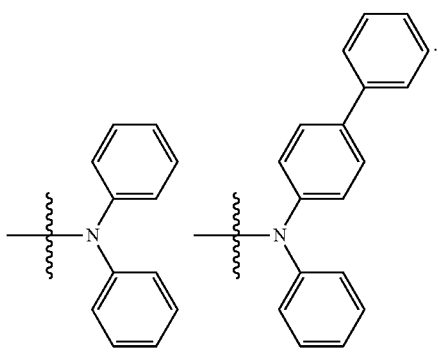 [SMILES: *N(c1ccccc1)c1ccccc1 ; *N(c1ccccc1)c1ccc(-c2ccccc2)cc1]

Optionally, the substituents of Ar$_1$, Ar$_2$, Ar$_3$ and Ar$_4$ are the same or different, and are each independently selected from deuterium, cyano, nitro, halogen, hydroxy, a substituted or unsubstituted alkyl with 1 to 33 carbon atoms, a substituted or unsubstituted cycloalkyl with 3 to 33 carbon atoms, a substituted or unsubstituted alkenyl with 2 to 33 carbon atoms, a substituted or unsubstituted alkynyl with 2 to 33 carbon atoms, a substituted or unsubstituted heterocycloalkyl with 2 to 40 carbon atoms, a substituted or unsubstituted aralkyl with 7 to 33 carbon atoms, a substituted or unsubstituted heteroaralkyl with 2 to 33 carbon atoms, a substituted or unsubstituted aryl with 6 to 33 carbon atoms, a substituted or unsubstituted heteroaryl with 1 to 33 carbon atoms, a substituted or unsubstituted alkoxy with 1 to 40 carbon atoms, a substituted or unsubstituted alkylamino with 1 to 33 carbon atoms, a substituted or unsubstituted arylamino with 6 to 33 carbon atoms, a substituted or unsubstituted alkylthio with 1 to 33 carbon atoms, a substituted or unsubstituted aralkylamino with 7 to 33 carbon atoms, a substituted or unsubstituted heteroarylamino with 1 to 24 carbon atoms, a substituted or unsubstituted alkylsilyl with 1 to 33 carbon atoms, a substituted or unsubstituted arylsilyl with 6 to 33 carbon atoms, a substituted or unsubstituted aryloxy with 6 to 30 carbon atoms, or a substituted or unsubstituted arylthio with 6 to 30 carbon atoms.

In certain embodiments, Ar$_1$, Ar$_2$, Ar$_3$ and Ar$_4$ are the same or different, and are each independently selected from a substituted or unsubstituted alkyl with 1 to 10 carbon atoms, a substituted or unsubstituted aryl with 6 to 30 carbon atoms, or a substituted or unsubstituted heteroaryl with 3 to 30 carbon atoms.

In the present disclosure, one, two, or three of X$_1$, X$_2$ and X$_3$ are N. Optionally, X$_1$, X$_2$ and X$_3$ in the above structure are the same, and are N.

Optionally, substituents in Ar$_1$, Ar$_2$, Ar$_3$ and Ar$_4$ are the same or different, and are each independently selected from deuterium, cyano, halogen, an alkyl with 1 to 10 carbon atoms, a cycloalkyl with 3 to 10 carbon atoms, an aryl with 6 to 20 carbon atoms, a heteroaryl with 3 to 18 carbon atoms, an alkoxy with 1 to 10 carbon atoms, an alkylthio with 1 to 10 carbon atoms, a aryloxy with 6 to 18 carbon atoms, an arylthio with 6 to 18 carbon atoms, or an arylamino with 6 to 20 carbon atoms.

Optionally, substituents in Ar$_1$ and Ar$_2$ are the same or different, and are each independently selected from deuterium, cyano, fluorine, an alkyl with 1 to 4 carbon atoms, a cycloalkyl with 5 to 10 carbon atoms, an aryl with 6 to 12 carbon atoms, a heteroaryl with 5 to 12 carbon atoms, an alkoxy with 1 to 4 carbon atoms, or an alkylthio with 1 to 4 carbon atoms. Specific examples of the substituents in Ar$_1$ and Ar$_2$ include, but not limited to, methyl, ethyl, n-propyl, isopropyl, tert-butyl, cyclohexyl, methoxy, methylthio, phenyl, naphthyl, biphenyl, pyridyl, dibenzofuryl, dibenzothienyl, carbazolyl, and the like.

Optionally, substituents in Ar$_4$ are the same or different, and are each independently selected from deuterium, cyano, fluorine, an alkyl with 1 to 4 carbon atoms, a cycloalkyl with 5 to 10 carbon atoms, an aryl with 6 to 10 carbon atoms, a heteroaryl with 5 to 12 carbon atoms, an alkoxy with 1 to 4 carbon atoms, or an arylamino with 6 to 12 carbon atoms. Specific examples of the substituents in Ar$_4$ include, but not limited to, methyl, ethyl, n-propyl, isopropyl, tert-butyl, cyclohexyl, methoxy, methylthio, phenyl, naphthyl, biphenyl, pyridyl, dibenzofuryl, dibenzothienyl, carbazolyl, diphenylamino, and the like.

Optionally, Ar$_1$ and Ar$_2$ are the same or different, and are each independently selected from a substituted or unsubstituted aryl with 6 to 18 carbon atoms, or a substituted or unsubstituted heteroaryl with 3 to 12 carbon atoms.

Preferably, Ar$_1$ and the Ar$_2$ are each independently selected from a substituted or unsubstituted aryl or heteroaryl having 5 to 18 ring-forming carbons. That is, Ar$_1$ and Ar$_2$ are each independently selected from a substituted or unsubstituted aryl having 5 to 18 ring-forming carbons, or a substituted or unsubstituted heteroaryl having 5 to 18 ring-forming carbons.

Optionally, $Ar_1$ and $Ar_2$ are each independently selected from a substituted or unsubstituted Z, and the unsubstituted Z is selected from the following groups:

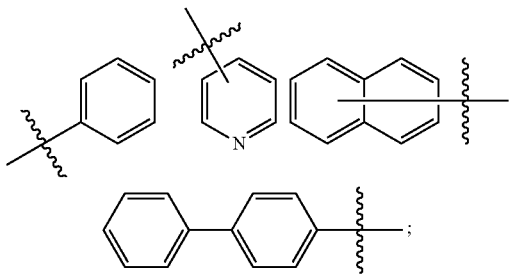

the substituted Z has one or two or more substituents, and the substituents are each independently selected from deuterium, fluorine, an alkyl with 1 to 4 carbon atoms, cyclopentyl, cyclohexyl, pyridyl, or phenyl.

Further, said $Ar_1$ and $Ar_2$ are each independently selected from the following groups:

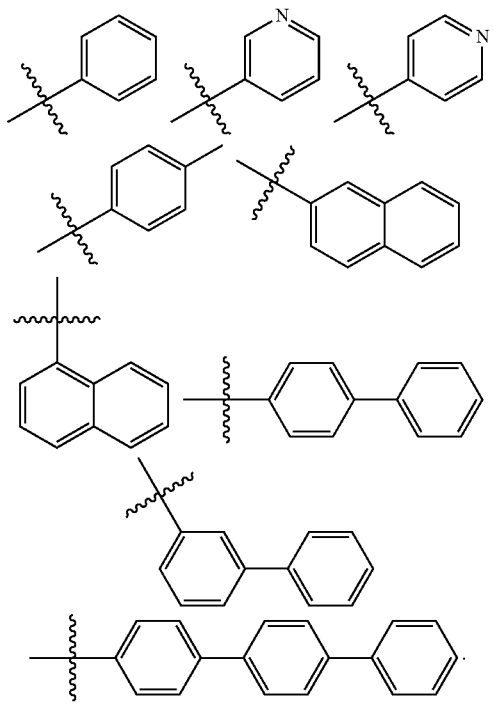

Optionally, said $Ar_3$ is selected from an alkyl with 1 to 4 carbon atoms, an aryl with 6 to 12 carbon atoms, or a heteroaryl with 4 to 12 carbon atoms.

Preferably, said $Ar_3$ is selected from the following groups:

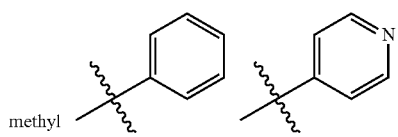

-continued

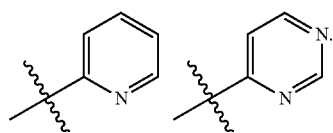

Optionally, $Ar_4$ is selected from an alkyl with 1 to 4 carbon atoms, or a substituted or unsubstituted V, and the unsubstituted V is selected from the following groups:

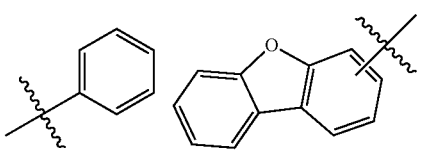

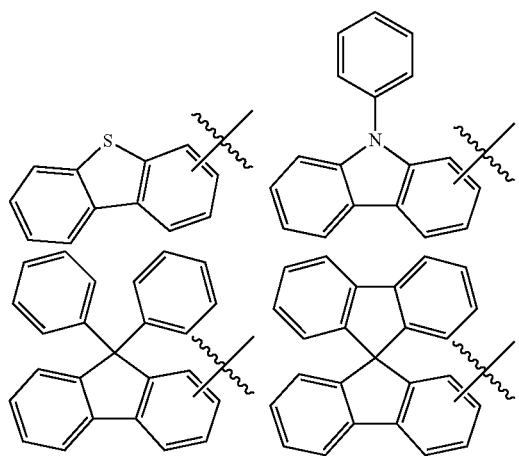

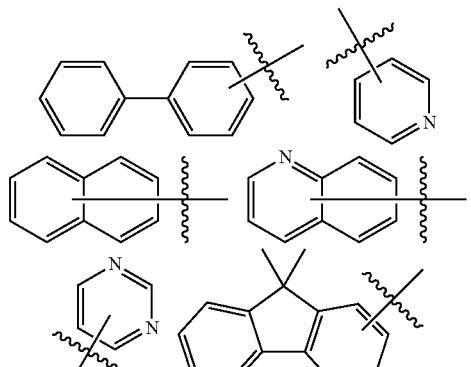

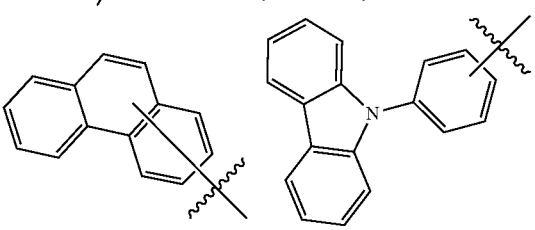

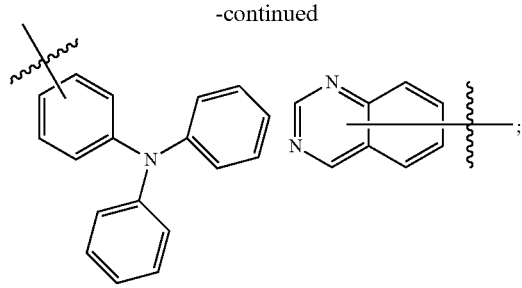

the substituted V has one or two or more substituents, and the substituents are each independently selected from deuterium, fluorine, an alkyl with 1 to 4 carbon atoms, a cycloalkyl with 3 to 10 carbon atoms, phenyl, naphthyl, or pyridyl.

Preferably, $Ar_4$ is selected from methyl, a substituted or unsubstituted aryl having 6 to 25 ring-forming carbon atoms, or a substituted or unsubstituted heteroaryl having 4 to 24 ring-forming carbon atoms.

Optionally, $Ar_4$ is selected from the following groups:

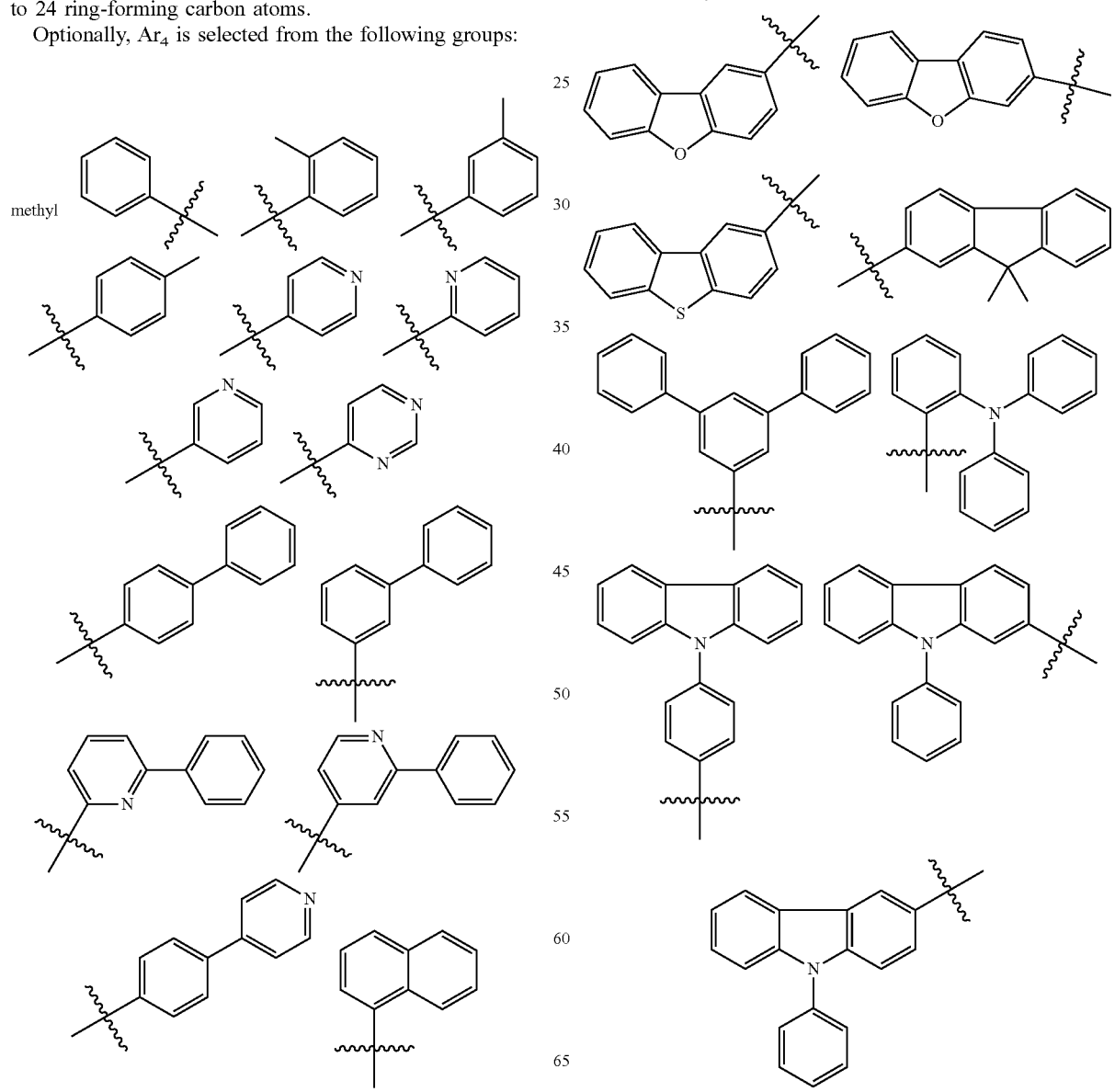

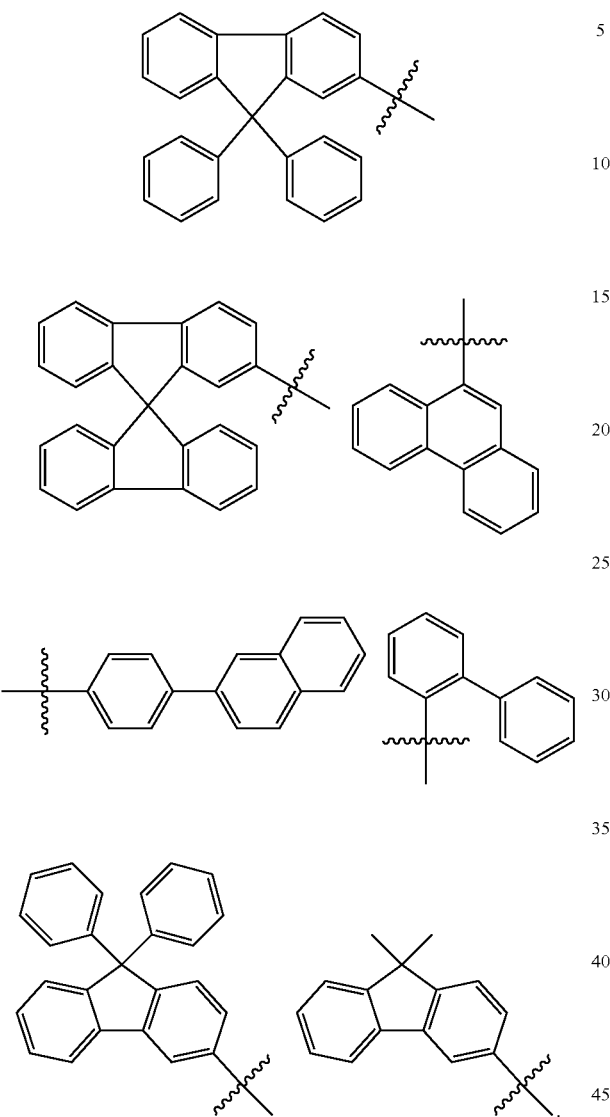
Optionally, the compound is selected from the following compounds:
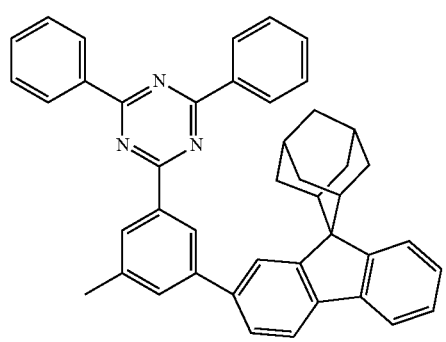
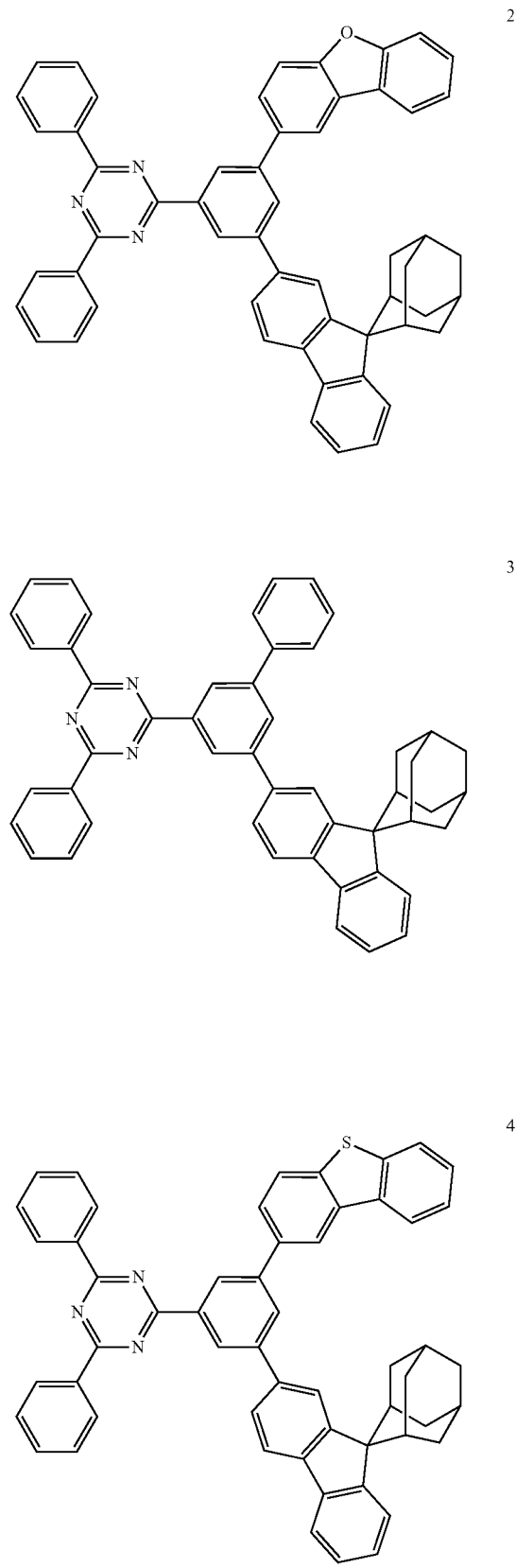

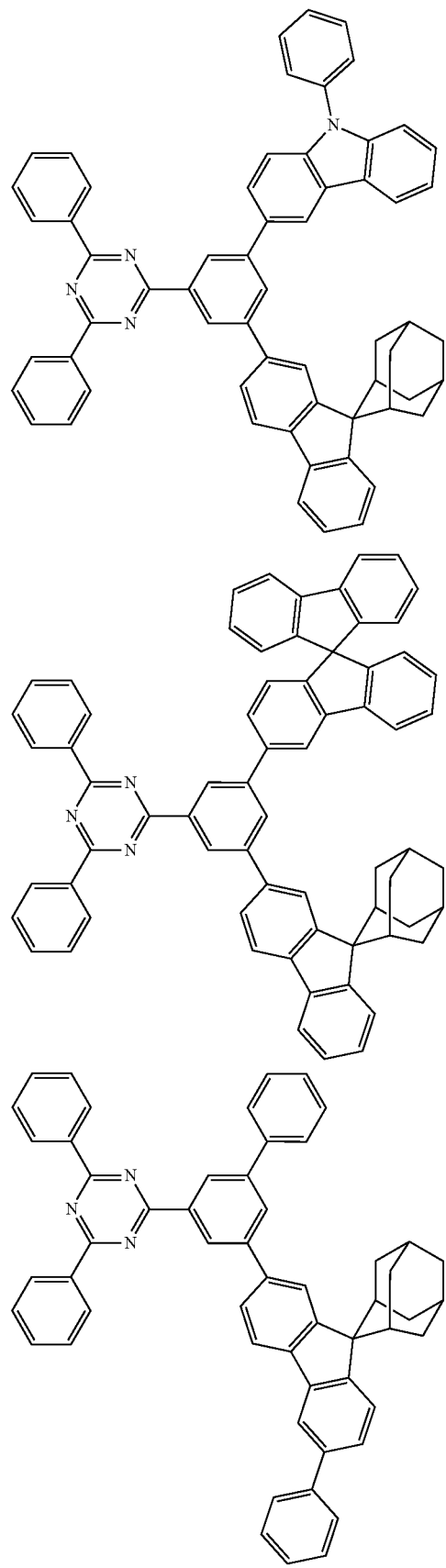
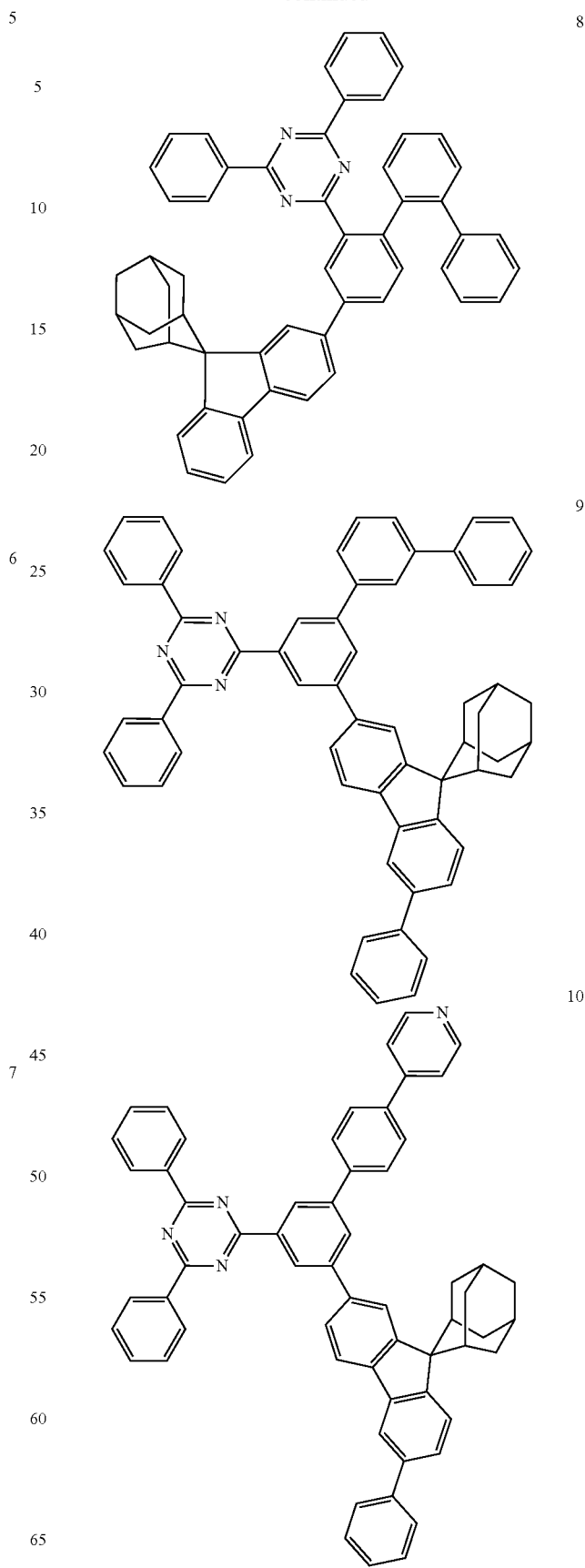

11
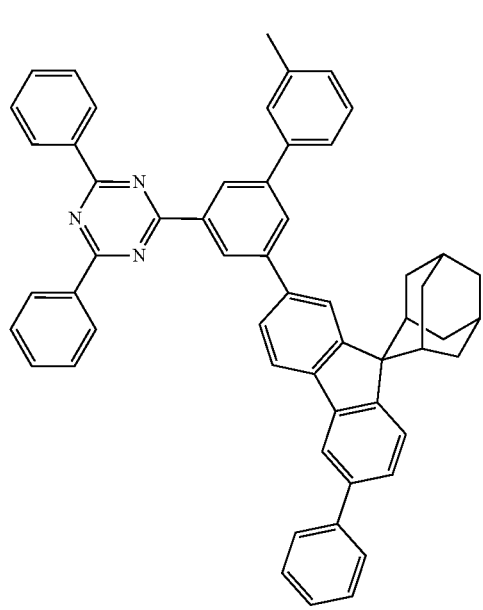
5
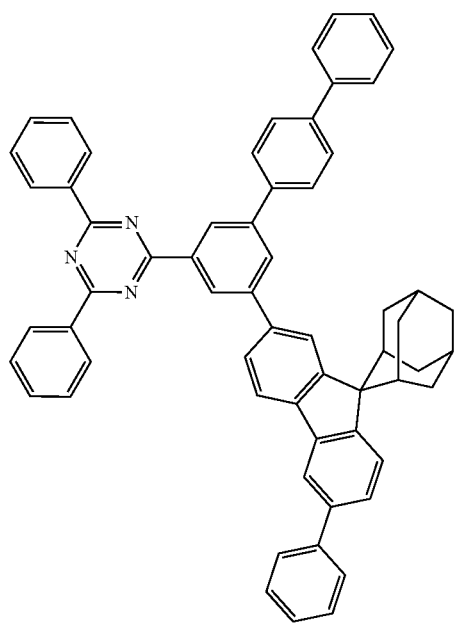
12
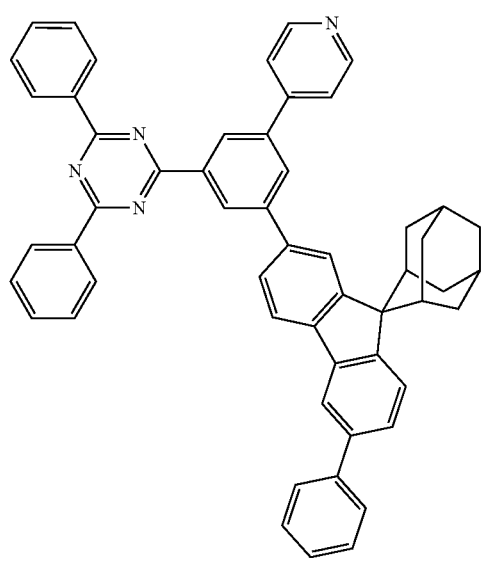
13
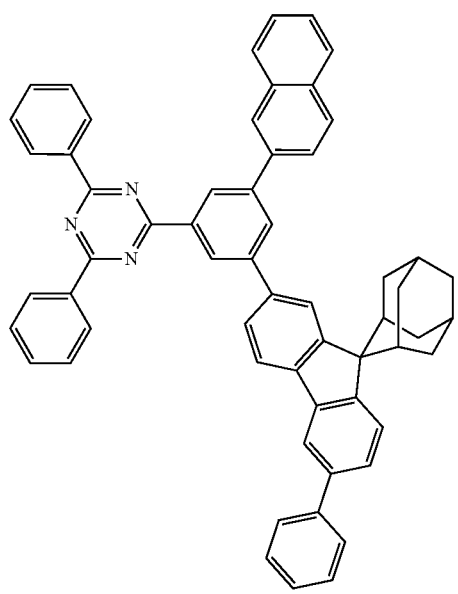
14

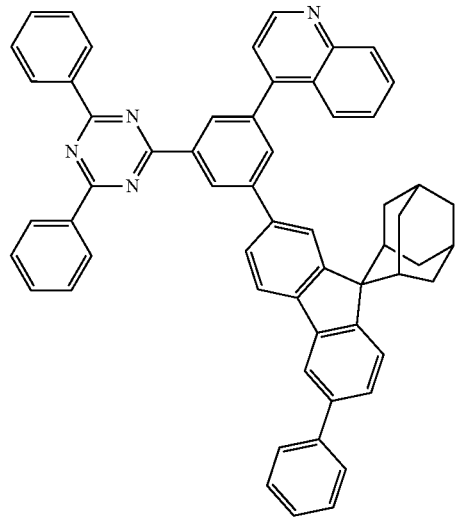
15
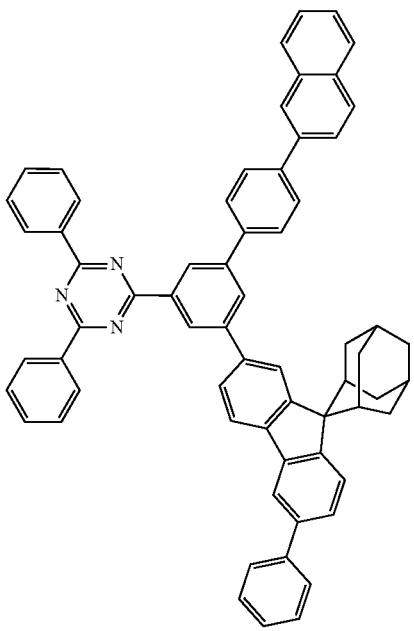
17
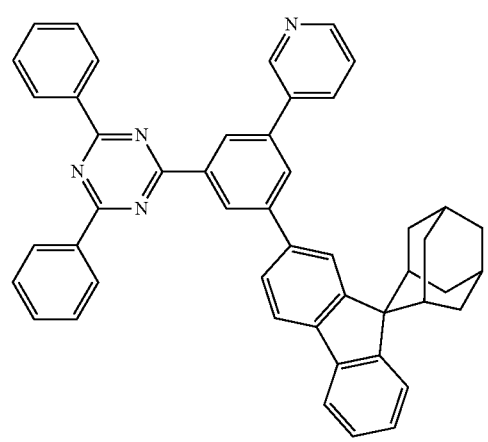
18
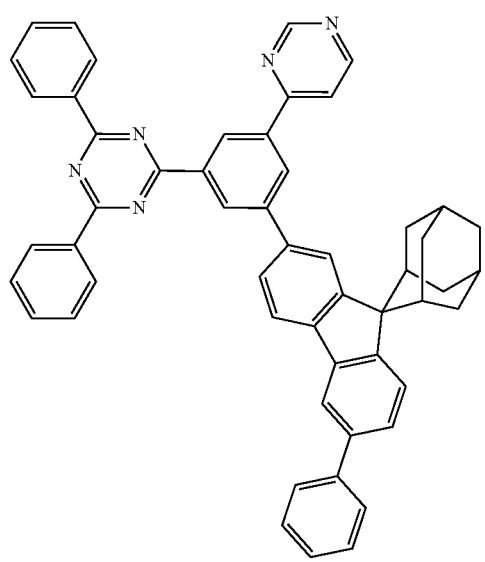
16
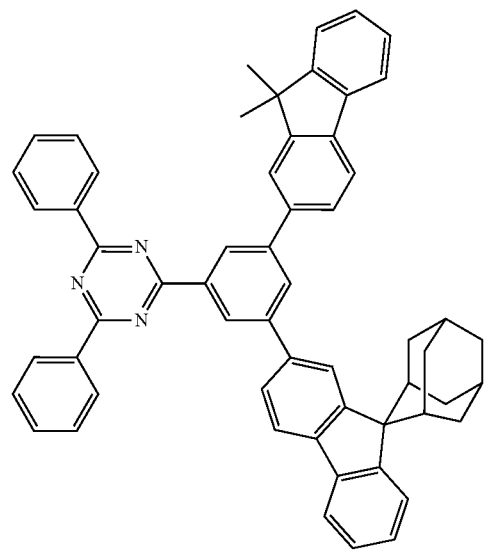
19

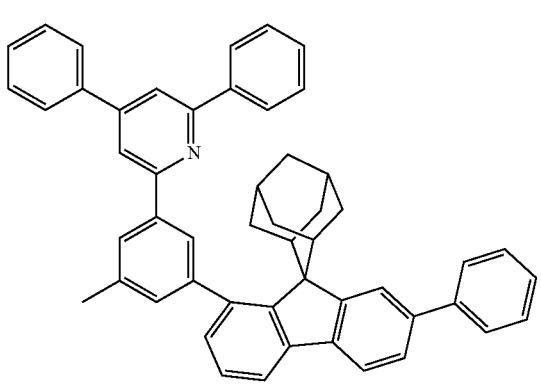
20
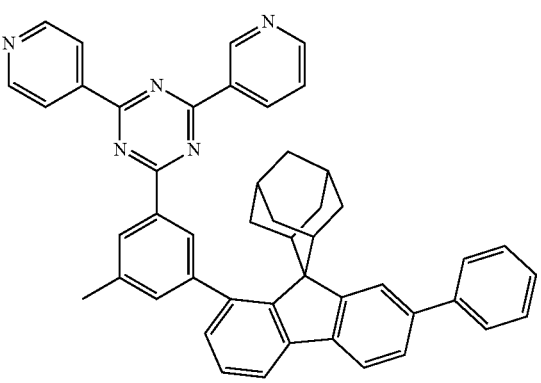
5
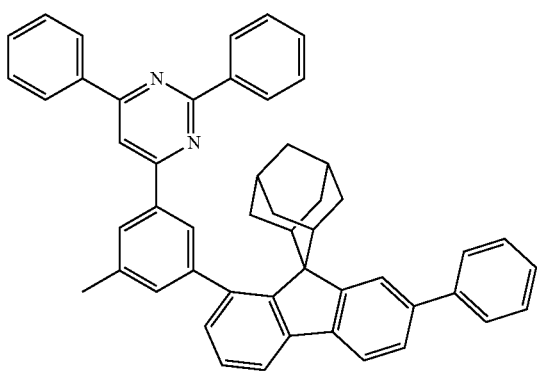
21
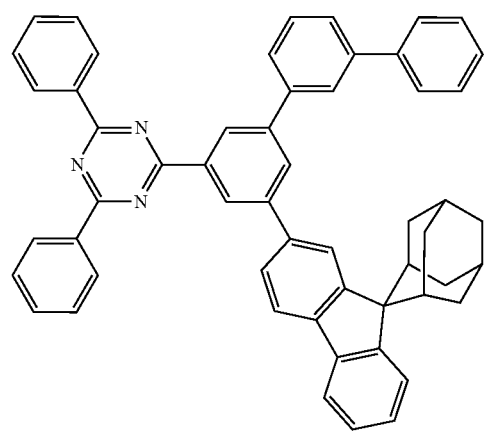
24
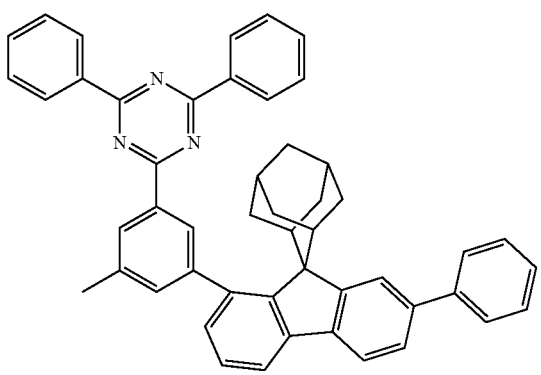
22
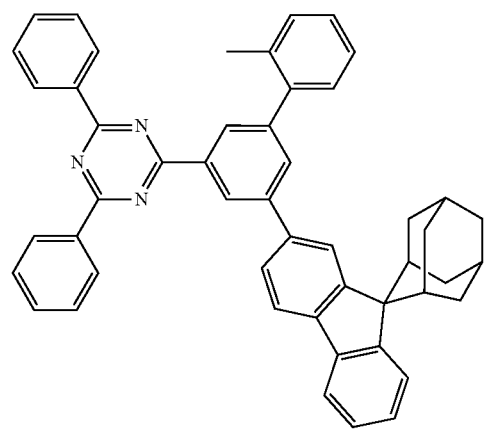
25
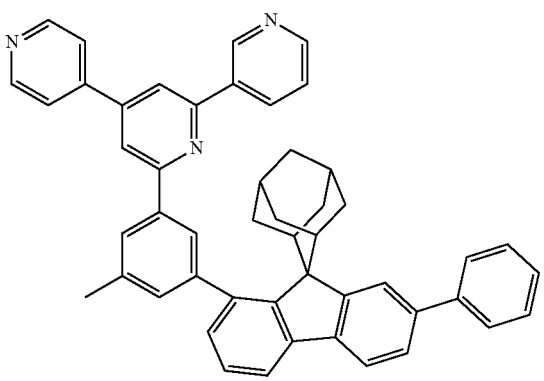
23
26

27
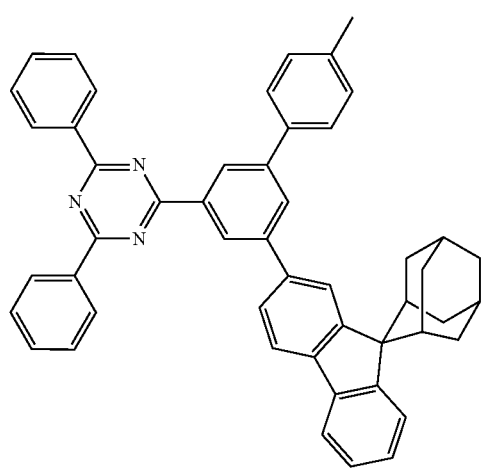
28
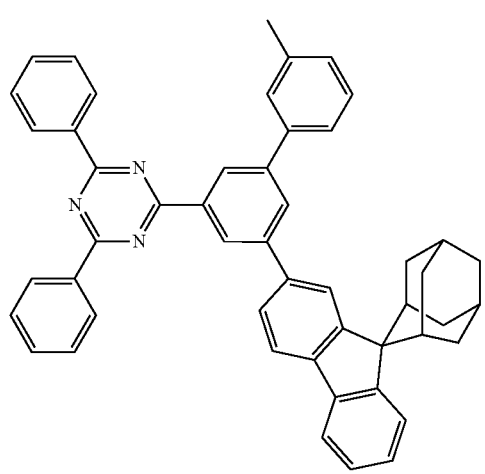
29
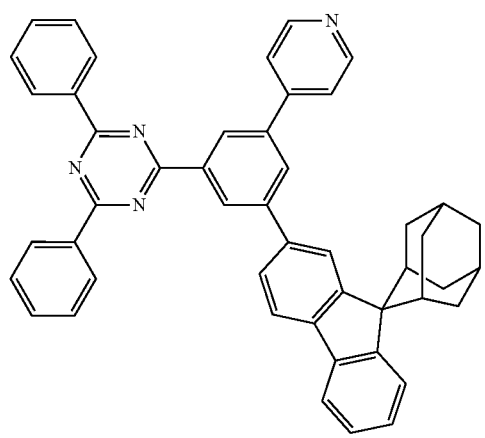
30
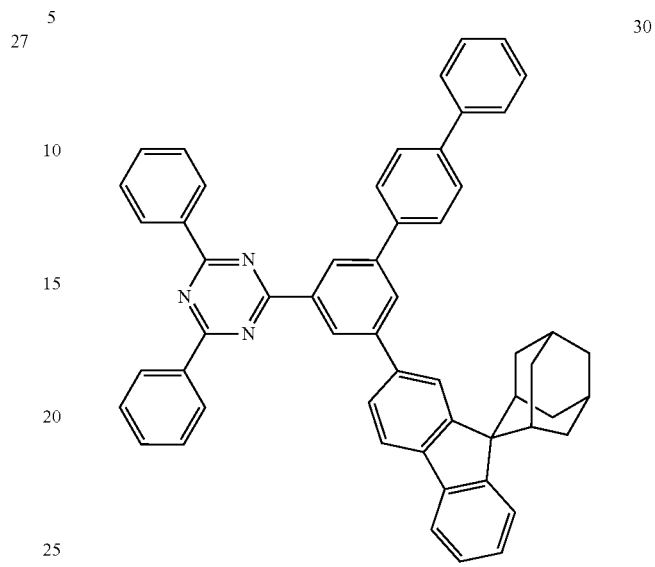
31
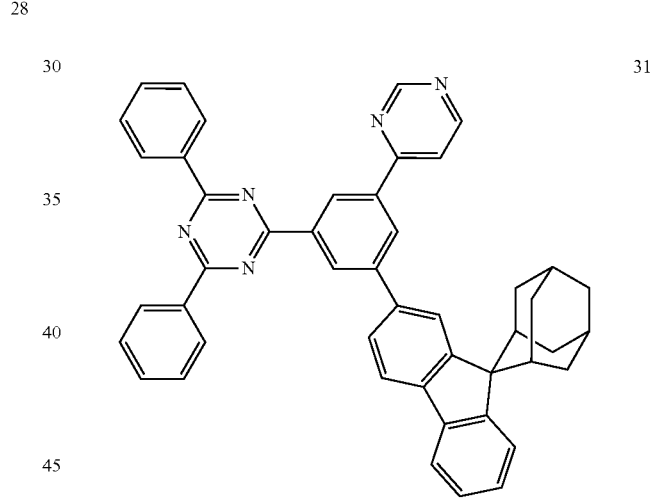
32
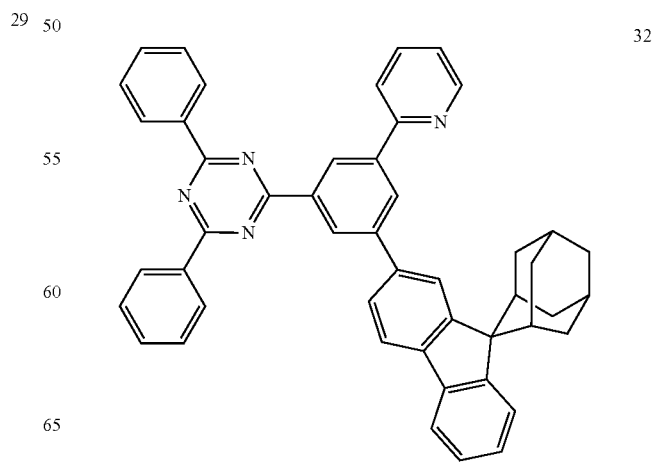

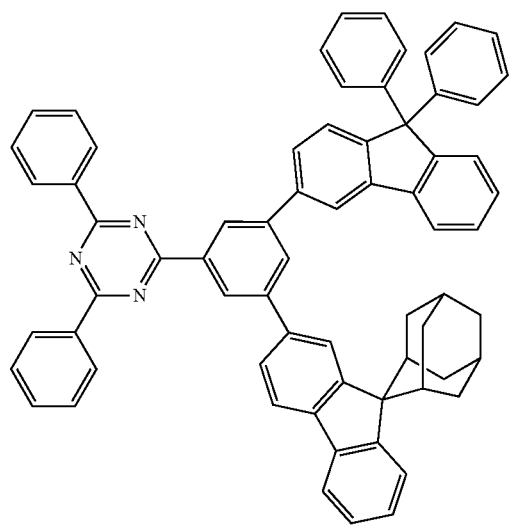
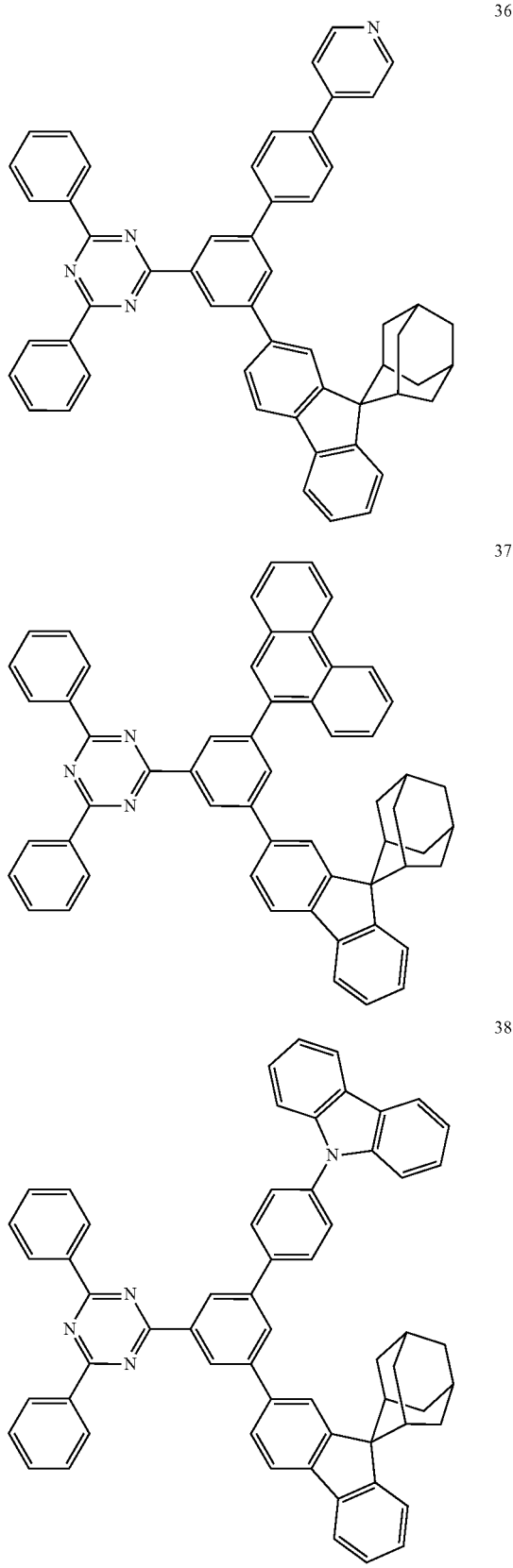

39
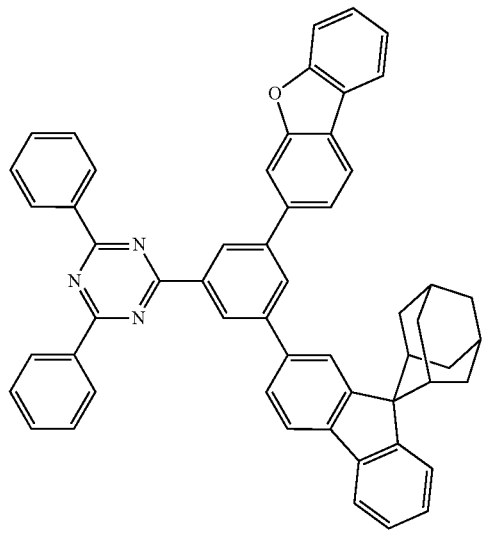
40
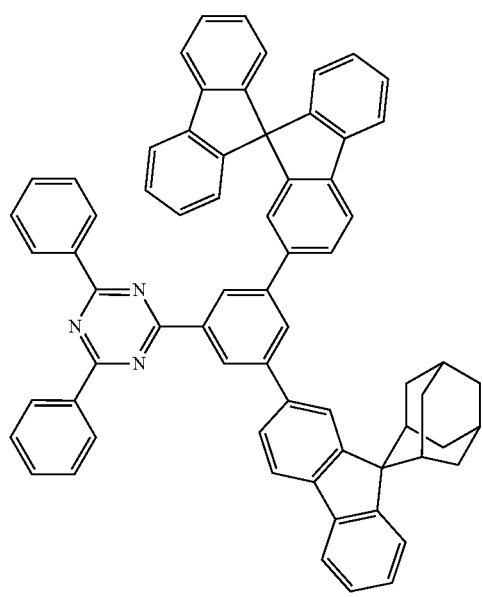
41
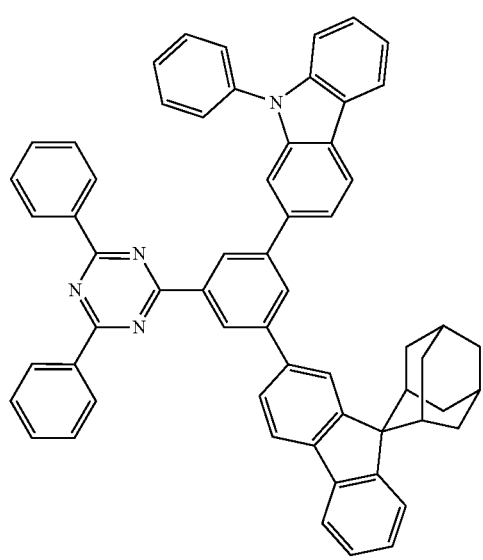
42
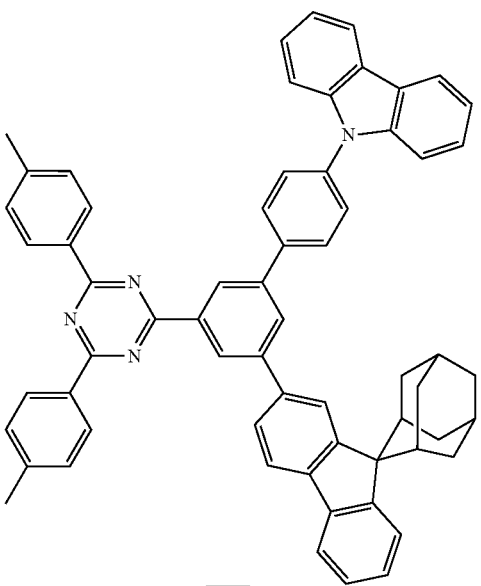
43
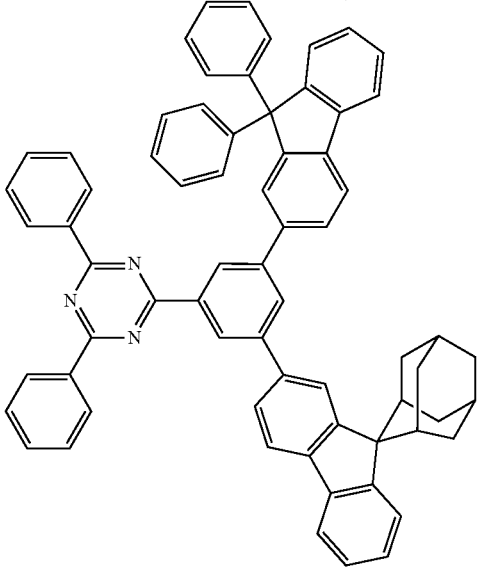
44
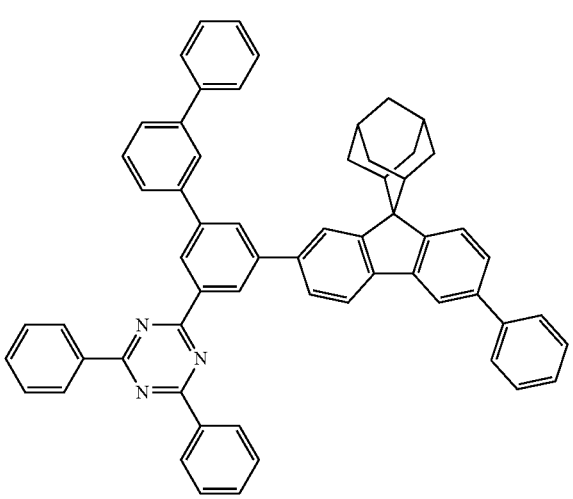

31
-continued
32
-continued
45
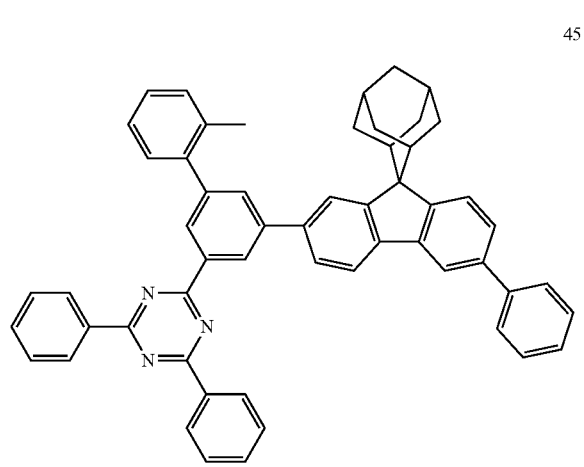
48
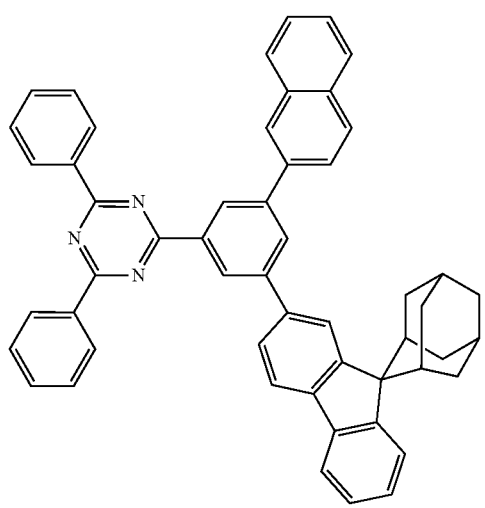
46
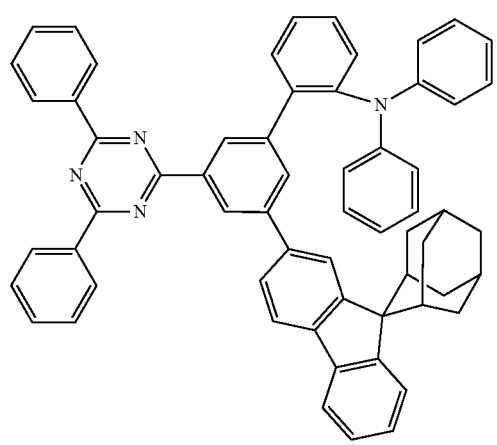
49
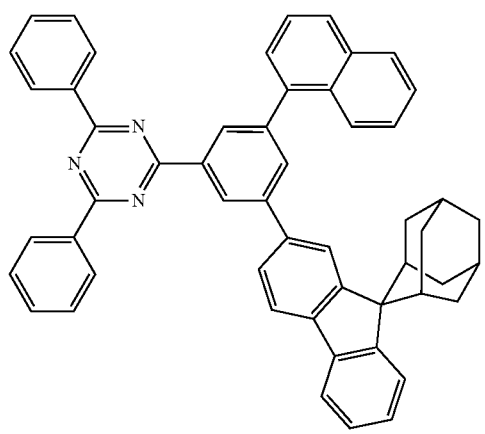
47
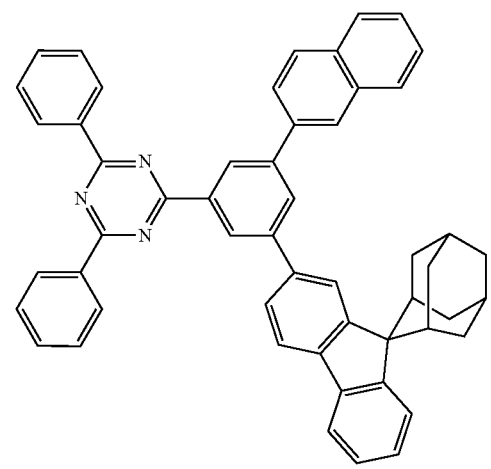
50
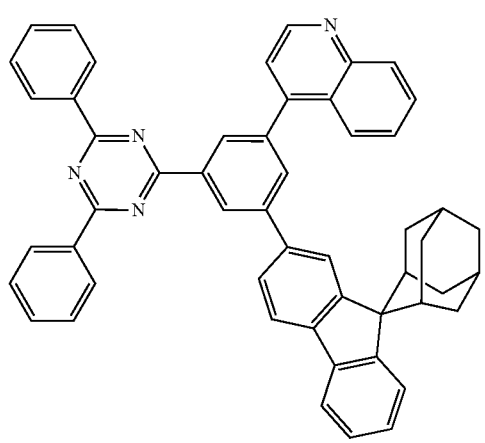

51
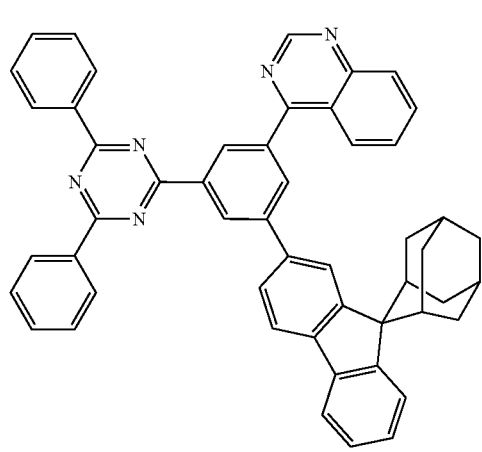
52
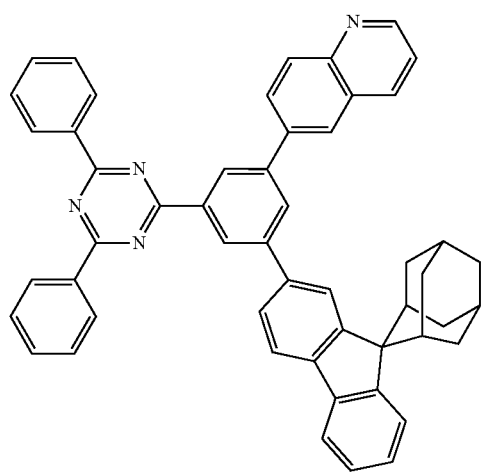
53
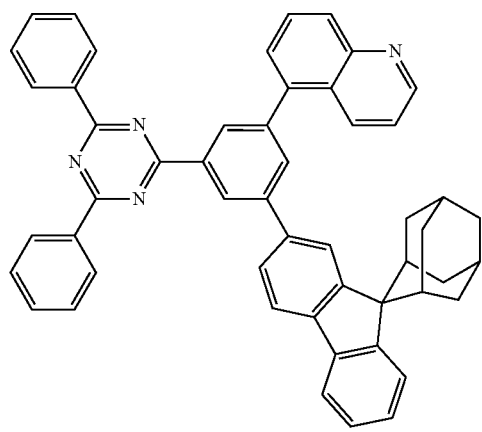
54
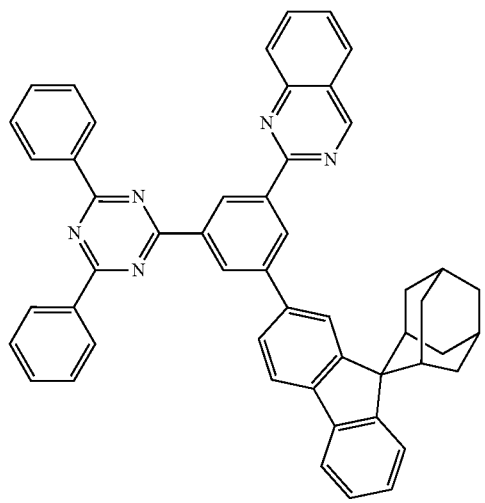
55
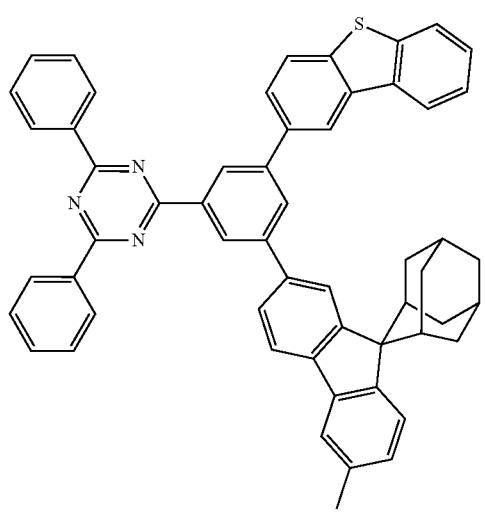
56
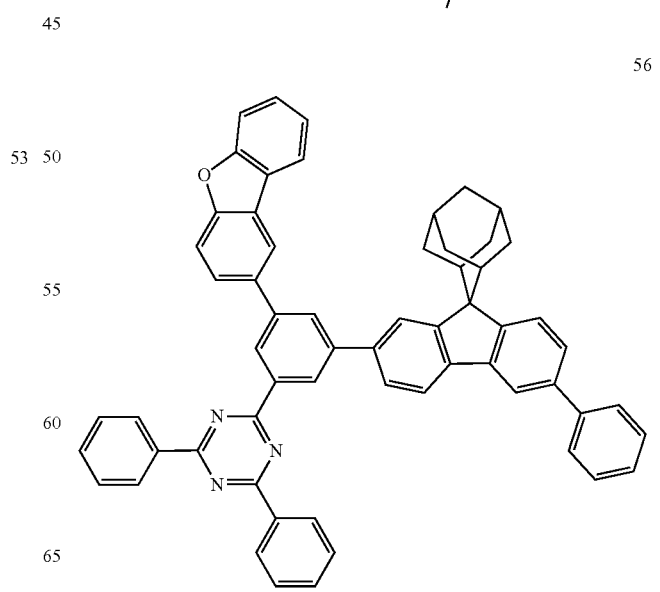

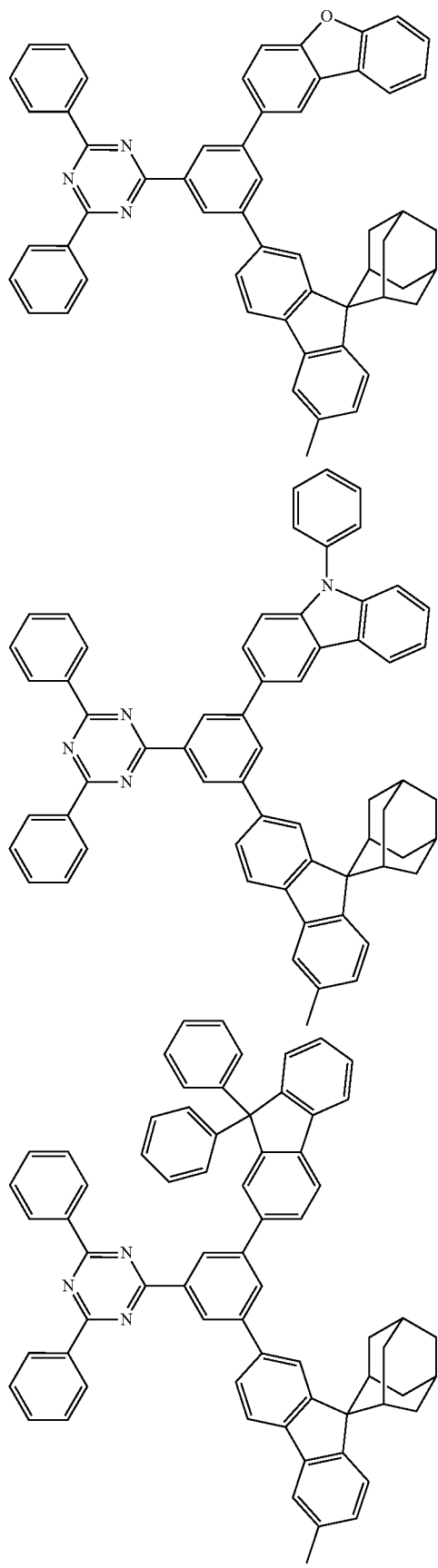
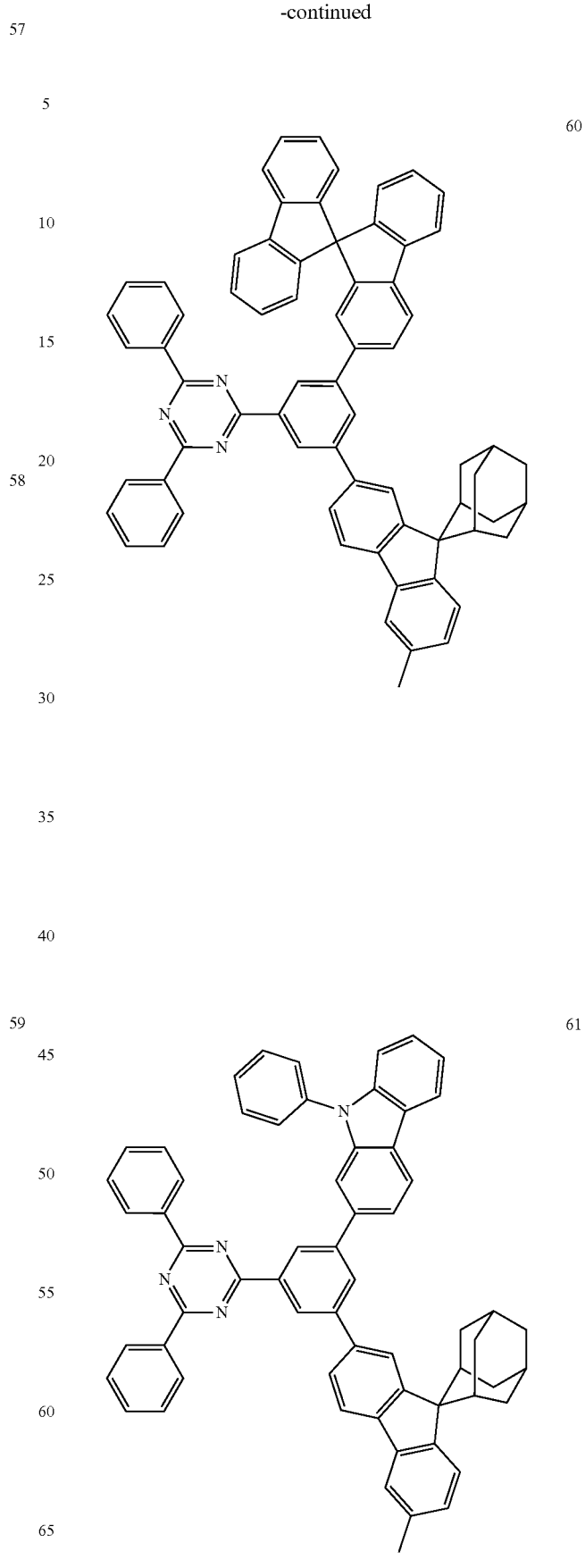

62
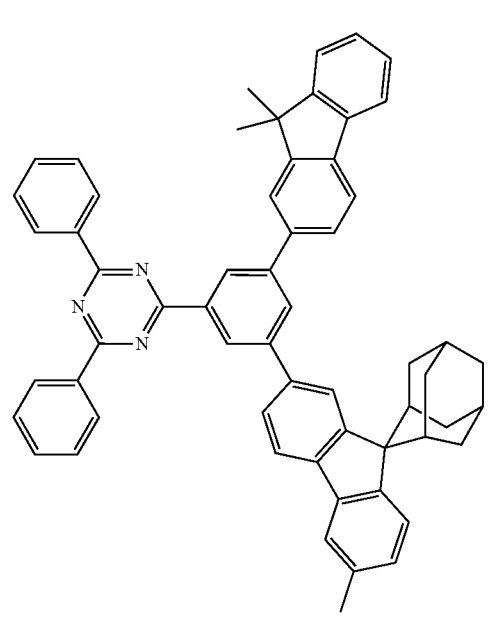
63
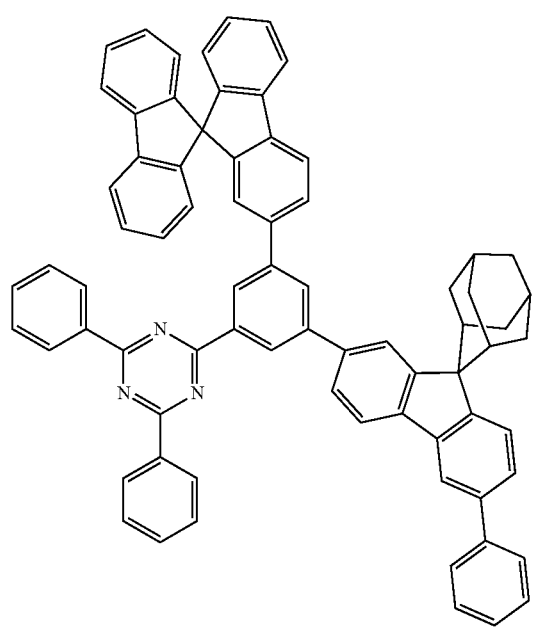
64
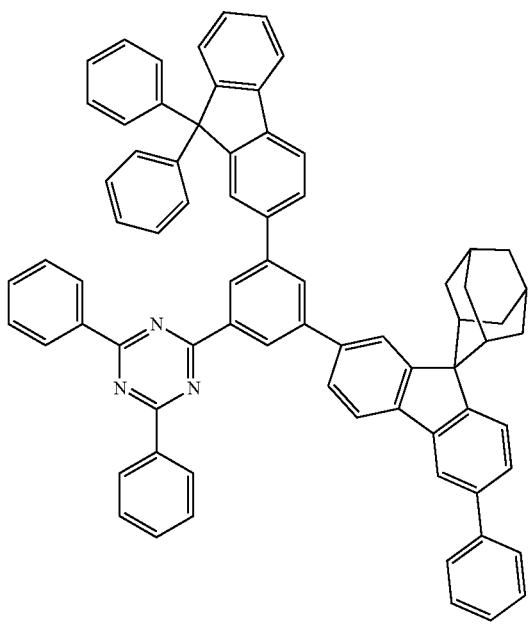
65
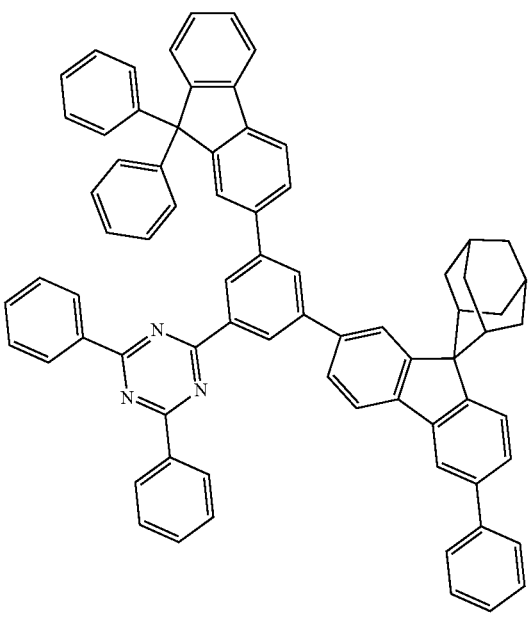

66
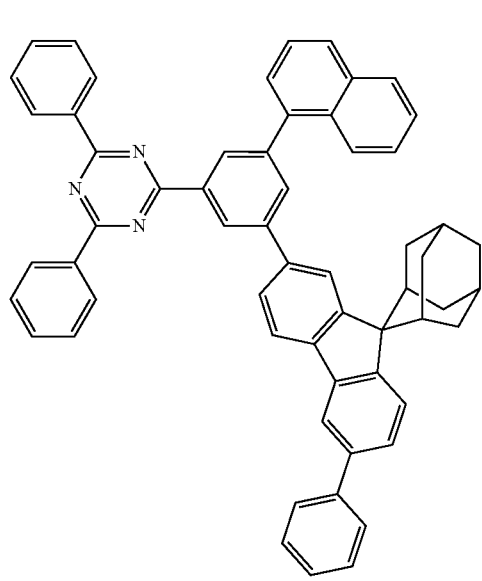
67
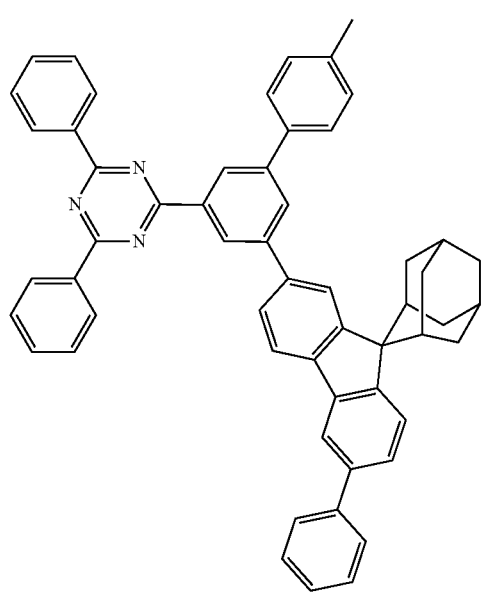
68
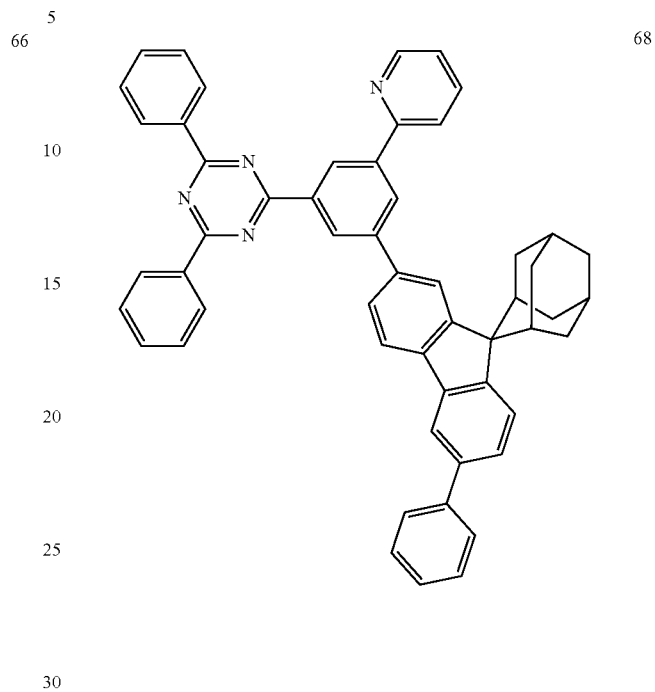
69
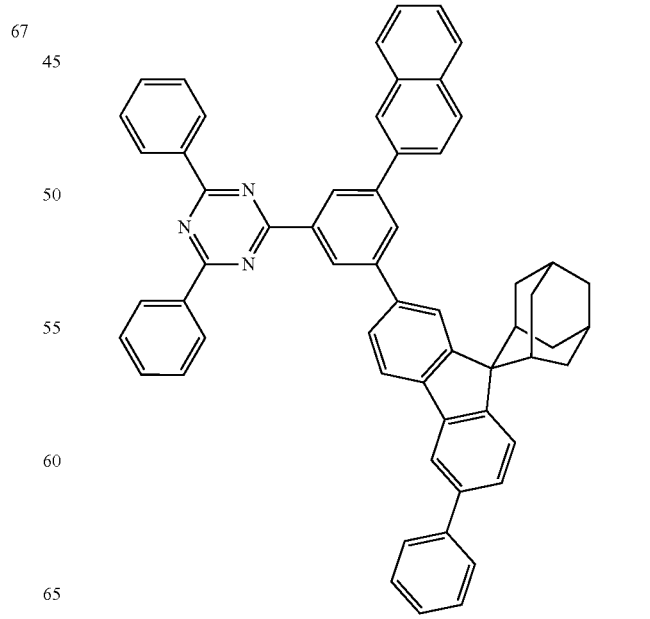

41
-continued
70
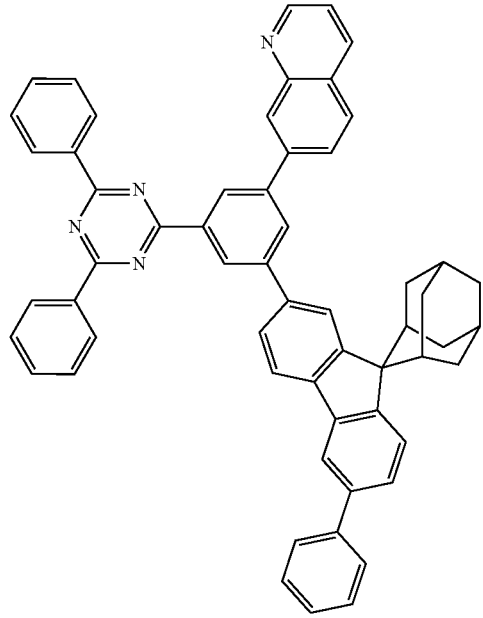
71
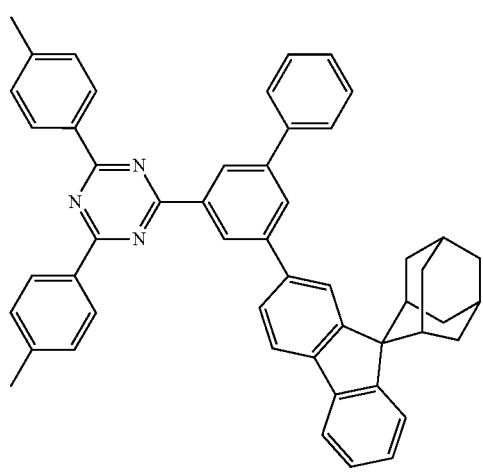
72
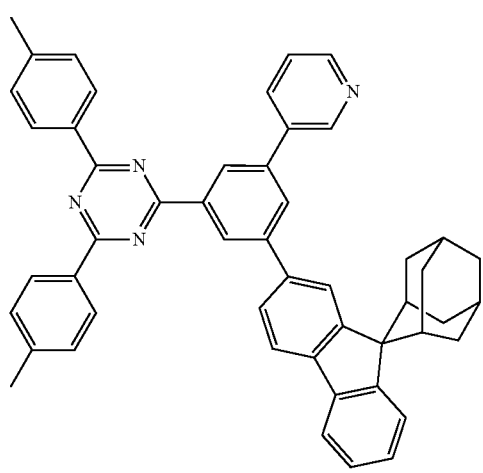
42
-continued
73
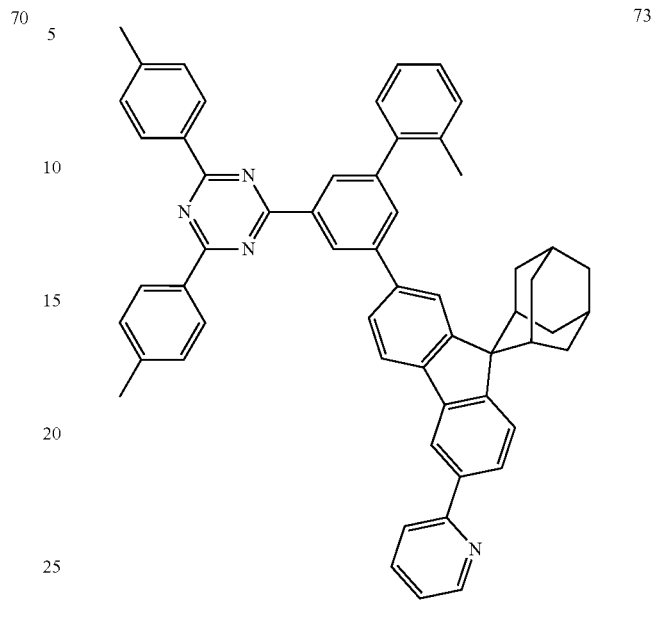
74
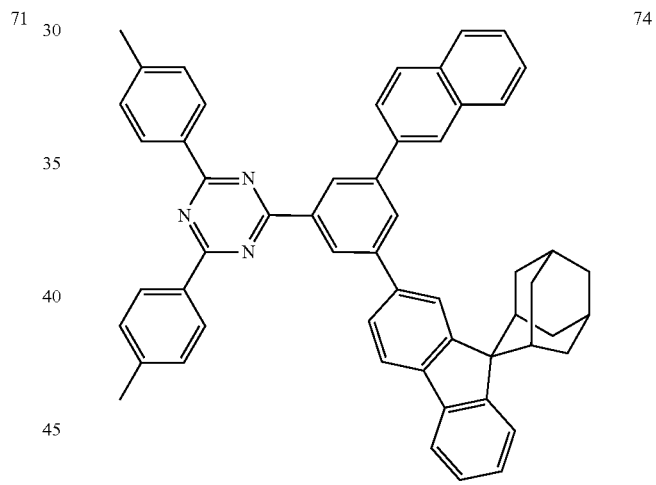
75
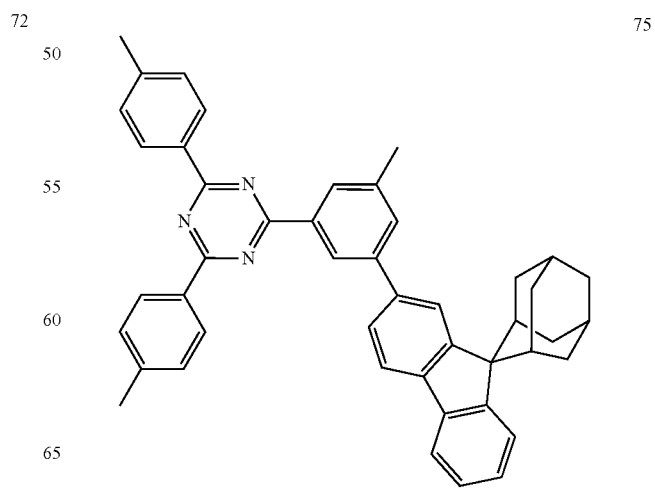

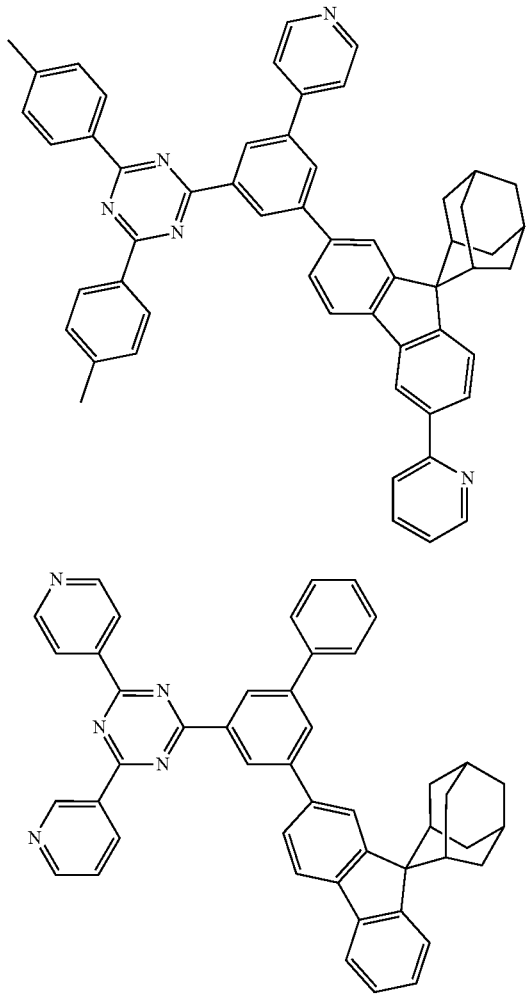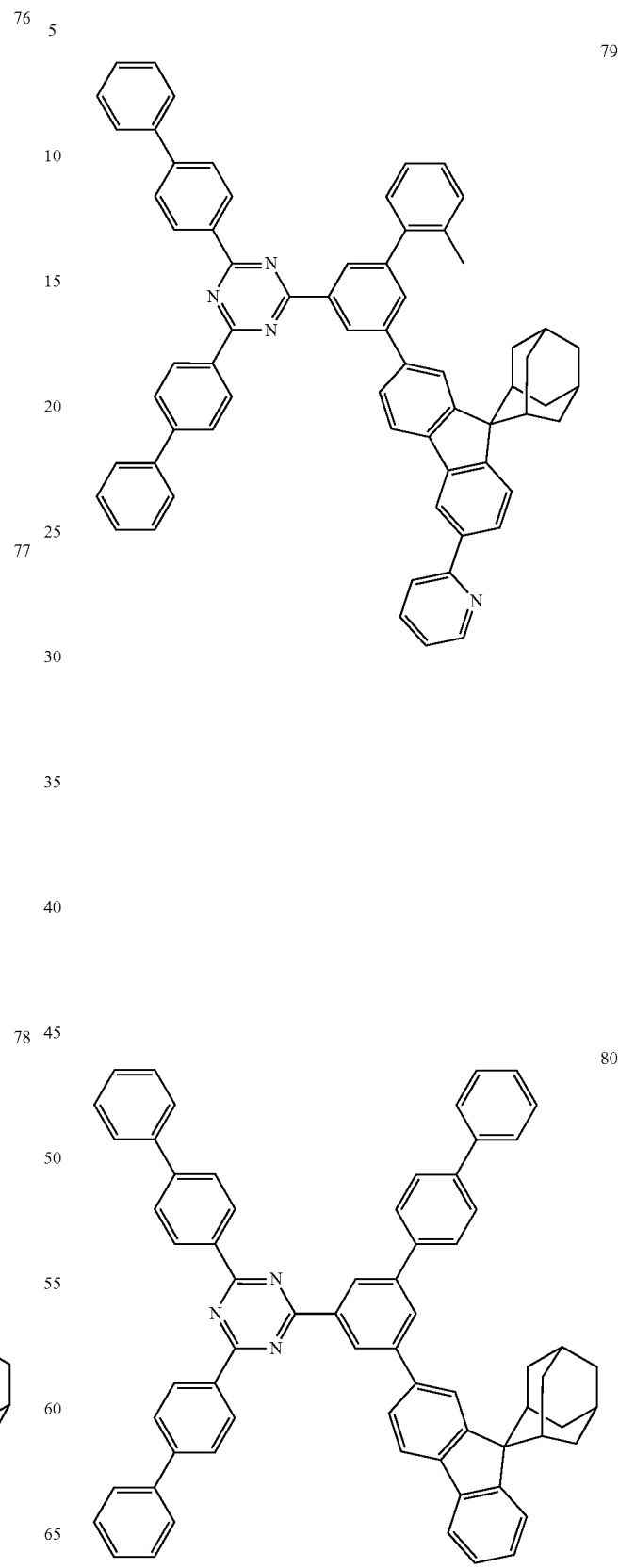

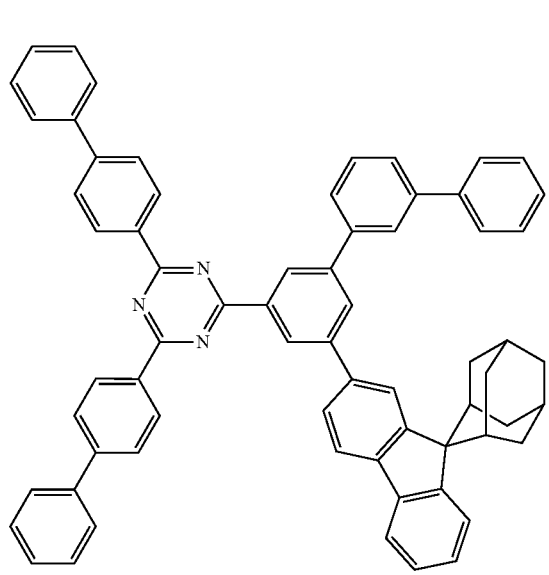
81
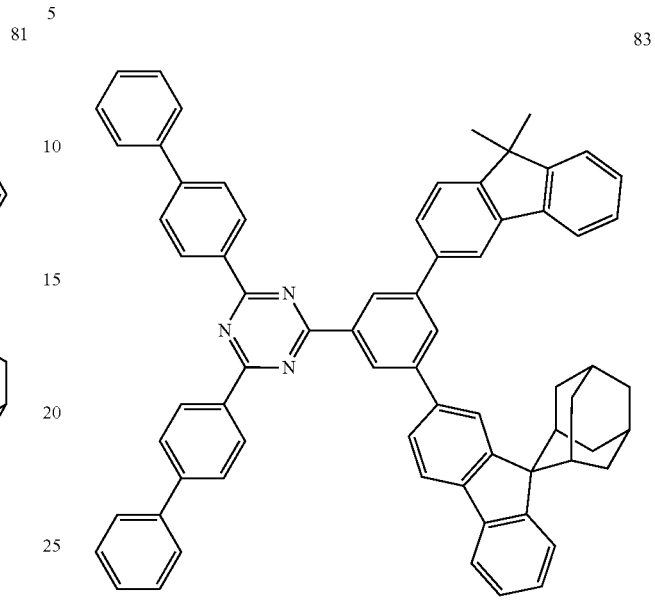
83
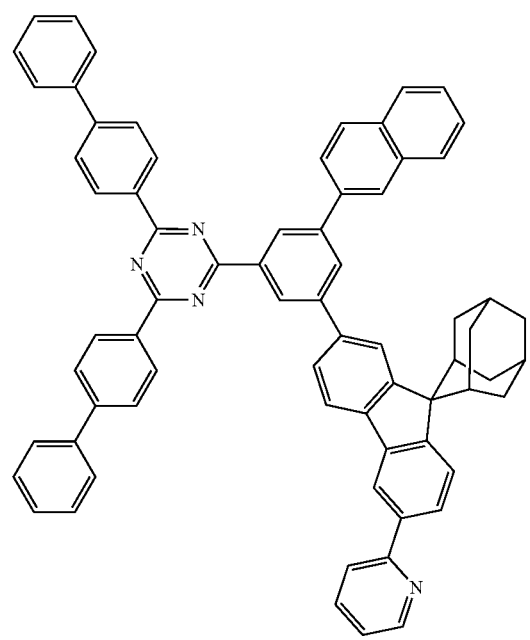
82
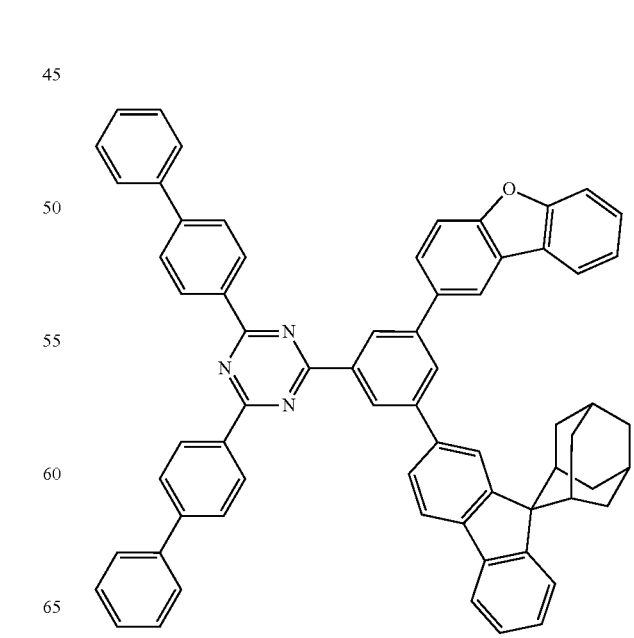
84

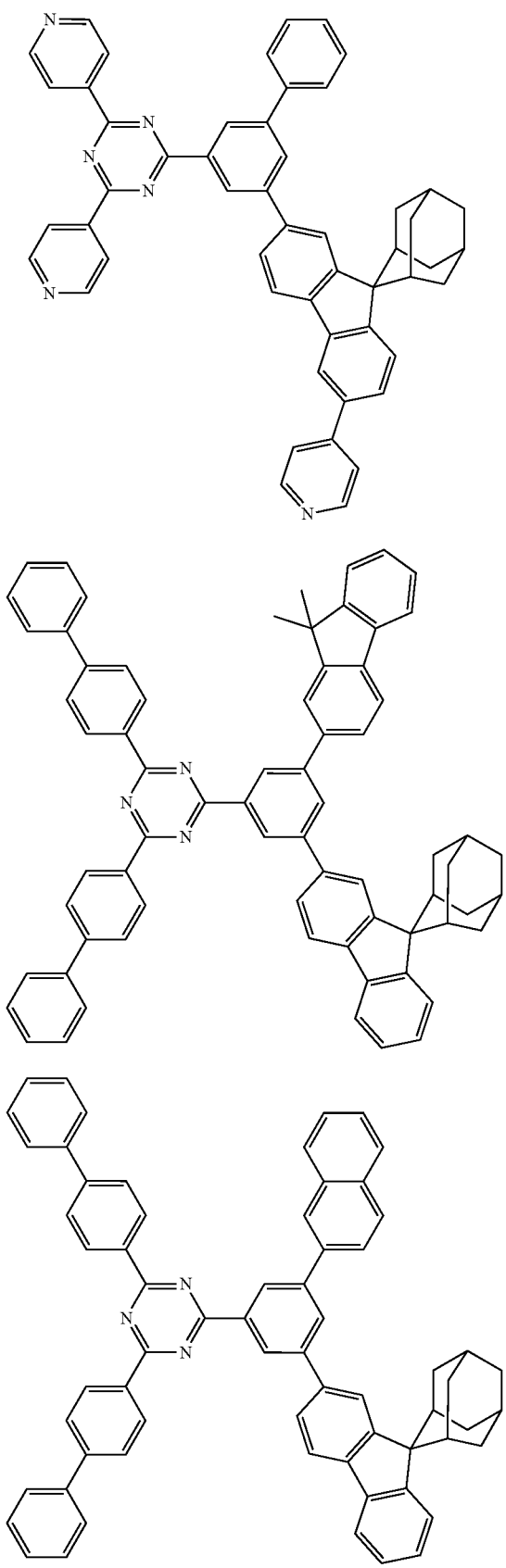
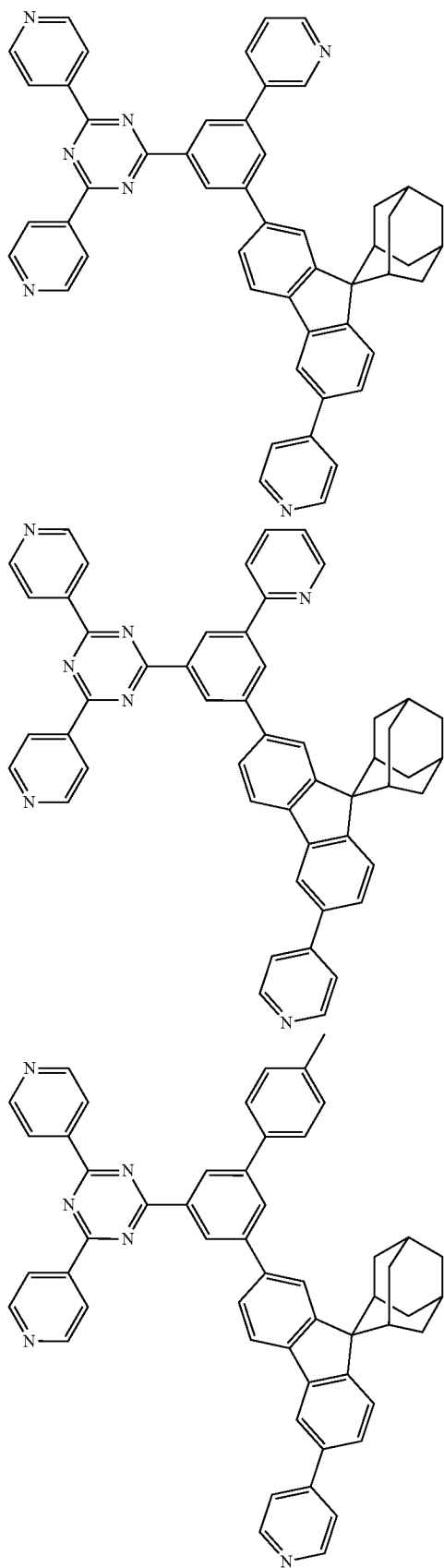

91
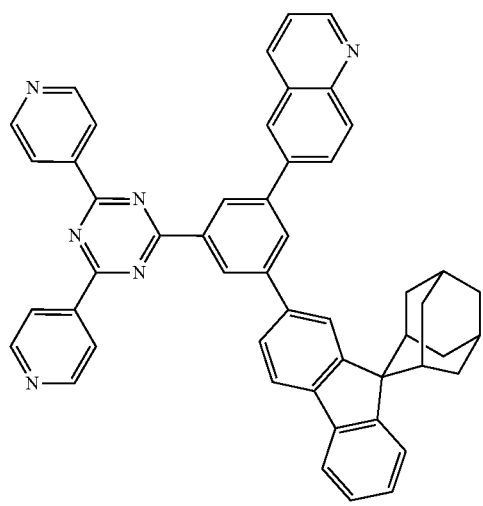
92
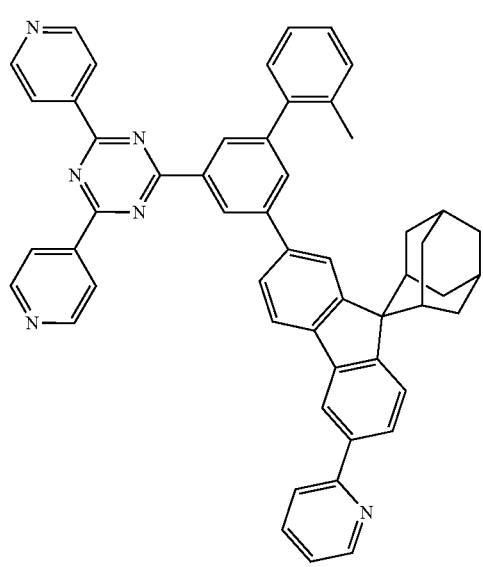
93
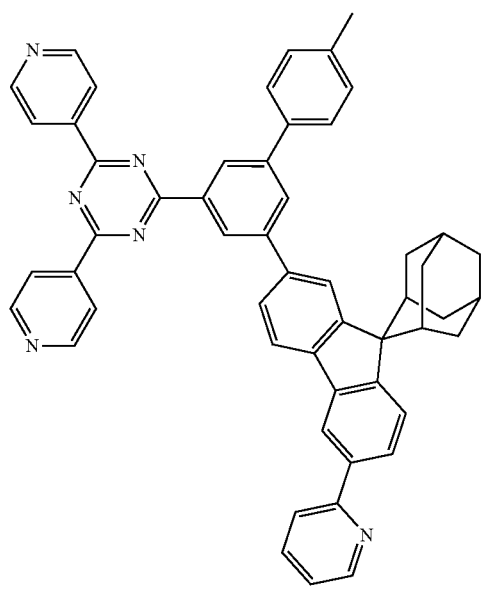
94
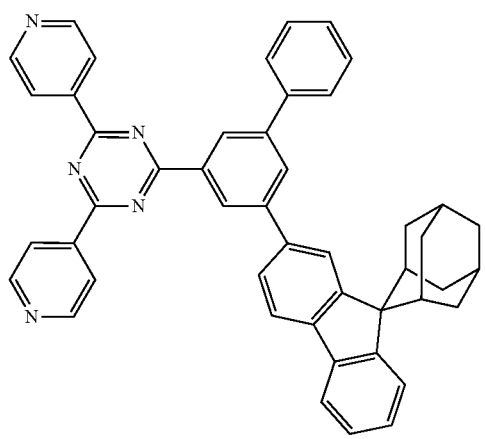
95
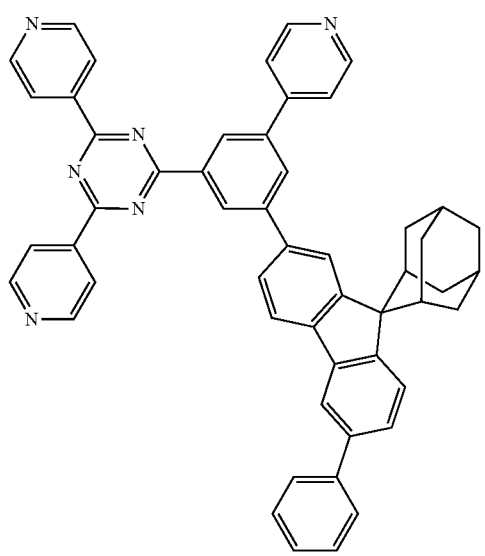
96
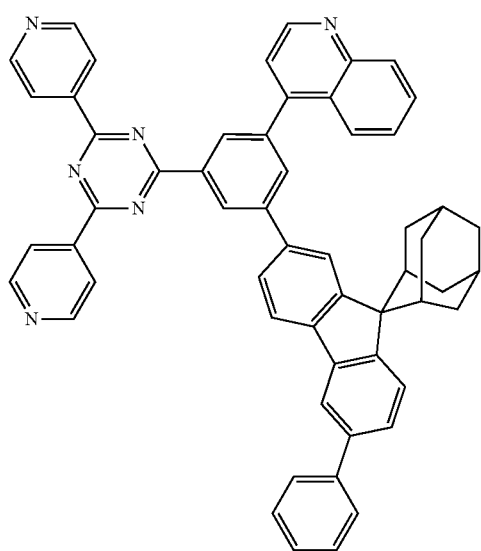

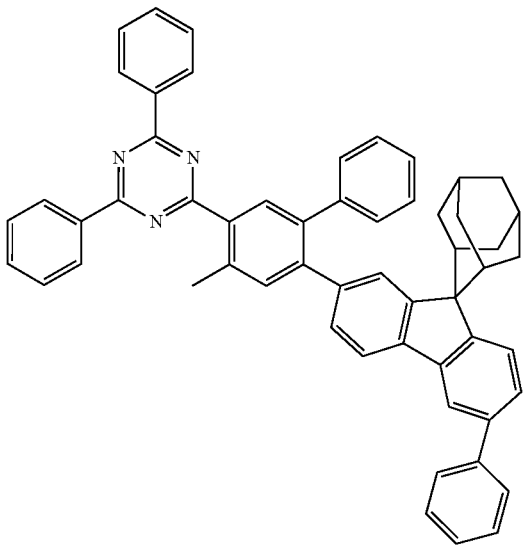
97

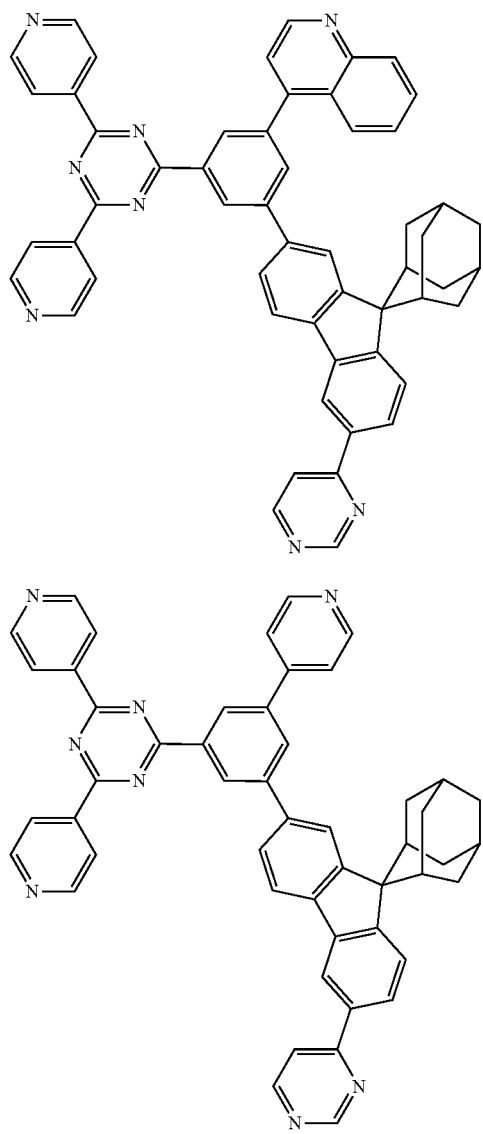
98

99

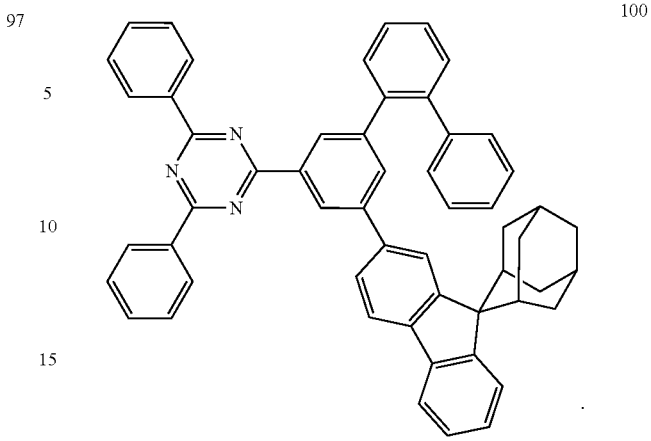
100

The present disclosure further provides an electronic device, comprising a cathode, an anode and a functional layer located between the cathode and the anode; and the functional layer contains the compound of the present disclosure.

Optionally, the functional layer comprises an electron transporting layer, and the compound is included in the electron transporting layer. That is, the electron transporting layer contains the compound of the present disclosure.

In one embodiment, the electronic device is an organic electroluminescent device. Where the anode material is preferably a material having a large work function that facilitates hole injection into the functional layer. Specific examples of the anode material include: metals such as nickel, platinum, vanadium, chromium, copper, zinc, gold or alloys thereof; metal oxides such as, zinc oxide, indium oxide, indium tin oxide (ITO) and indium zinc oxide (IZO); combination of metals and oxides such as ZnO:Al or $SnO_2$:Sb; or conductive polymers, such as poly(3-methylthiophene), poly[3,4-(ethylidene-1,2-dioxy)thiophene] (PEDT), polypyrrole and polyaniline. Preferably, a transparent electrode containing indium tin oxide (ITO) is included as the anode.

The cathode material is a material having a small work function that facilitates electron injection into the functional layer. The cathode materials may specifically include metals such as magnesium, calcium, sodium, potassium, titanium, indium, yttrium, lithium, gadolinium, aluminum, silver, tin and lead, or their alloys; or multilayer materials such as LiF/Al, Liq/Al, $LiO_2$/Al, LiF/Ca, LiF/Al and $BaF_2$/Ca, but not limited thereto. Preferably, a metal electrode containing aluminum serves as the cathode.

As shown in FIG. 1, the functional layer 20 of the organic electroluminescent device is a multilayer structure, and these multilayer structures may include a hole injecting layer 201, a hole transporting layer 202, a light-emitting layer 204, an electron transporting layer 206, an electron injecting layer 207, and the like. Of course, an electron blocking layer 203, a hole blocking layer 205, a capping layer 40, and the like. The compound of the present disclosure may be included in the electron transporting layer 206.

The above organic electroluminescent device may be applied in a plurality of electronic device. For example, the electronic device may be display device, illuminating device, optical communication device, or other types of electronic device, for example, may include, but not limited to, a computer screen, a mobile phone screen, a television, an electronic paper, an emergency lamp, an optical module, and the like.

Figure 2:
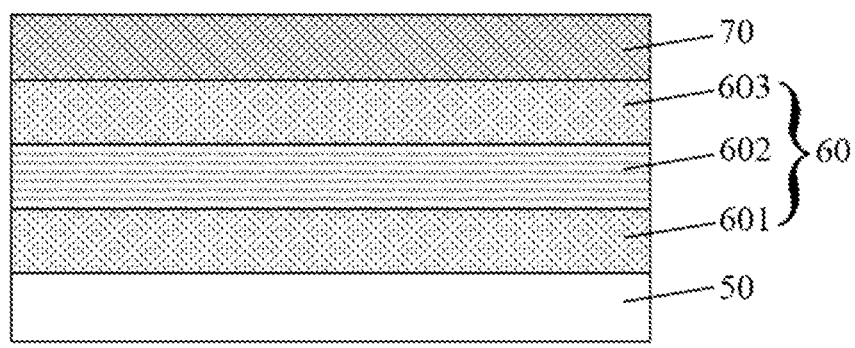
FIG. 2 is a structural schematic diagram of a solar cell in an embodiment of the present disclosure.

In another embodiment, the electronic device is a solar cell, and other photoelectric conversion device. With an organic matter having photosensitive properties as a semiconductor material, the solar cell produces voltage to form current via a photovoltaic effect, thus achieving the effect of solar power generation. As shown in FIG. 2, the solar cell also consists of a cathode 70, an anode 50 and a functional layer 60; the functional layer 60 of the solar cell usually includes a photosensitive active layer 602, a hole transporting layer 601 and an electron transporting layer 603, and the like. Where the photosensitive active layer 602 is used for absorbing photons to generate excitons and carriers; the hole transporting layer 601 and the electron transporting layer 603 are used for improving the collection efficiency of holes and electrons of electrodes. The compound of the present disclosure can be used for the electron transport layer 603 of the solar cell to enhance the transmission efficiency of electrons, thus promoting the photoelectric conversion efficiency of the solar cell, improving the lifetime characteristic, efficiency characteristic, electrochemical stability and thermal stability, and increasing open-circuit voltage of the solar cell.

The reparation method of the compounds in the embodiments of the present disclosure will be specified in detail hereafter.

Synthesis of Compound 1

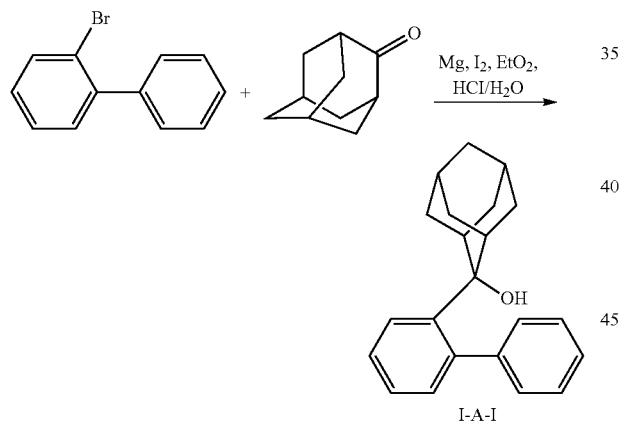

Magnesium strips (15.44 g, 643.5 mmol) and diethyl ether (100 mL) were placed in a dry round-bottom flask under nitrogen protection, and iodine (119 mg) was added. Afterwards, a diethyl ether solution (200 mL) dissolved with 2-bromobiphenyl (50.00 g, 214.49 mmol) was slowly dropped into the flask, at the end of dropping, the solution was warmed to 35° C. and stirred for 3 h; then the reaction solution was cooled to 0° C., and a diethyl ether solution (200 mL) dissolved with adamantanone (48.33 g, 321.7 mmol) was dropped slowly, at the end of dropping, the solution was warmed to 35° C. and stirred for 6 h; the reaction solution was cooled to room temperature, and 5% hydrochloric acid was added until pH<7, and stirred for 1 h, and diethyl ether (200 mL) was added for extraction; the obtained organic phases were combined, and dried by anhydrous magnesium sulfate, then filtered and treated under reduced pressure to remove solvent; the obtained crude product was purified by silica gel column chromatography with ethyl acetate/n-heptane (1:2) as a mobile phase to obtain a white solid intermediate I-A-1 (43 g, yield: 66.34%).

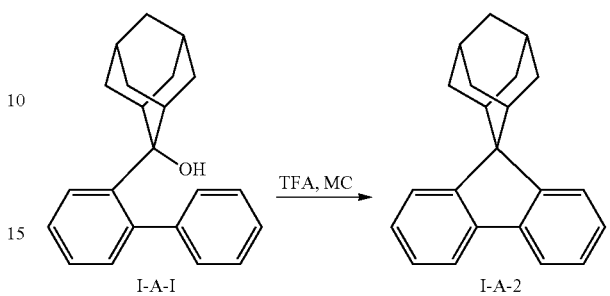

The intermediate I-A-1 (43 g, 141.2 mmol), trifluoroacetic acid (40.26 g, 353.1 mmol) and dichloromethane (300 mL) were added to a round-bottom flask, and stirred for 2 h under nitrogen protection; afterwards, aqueous solution of sodium hydroxide was added to the reaction solution until pH=8, and liquid separation was performed; the obtained organic phases were dried by anhydrous magnesium sulfate, filtered and treated under reduced pressure to remove the solvent; the obtained crude product was purified by silica gel column chromatography with dichloromethane/n-heptane (1:2) to obtain a white solid intermediate I-A-2 (36.5 g, yield: 90.24%).

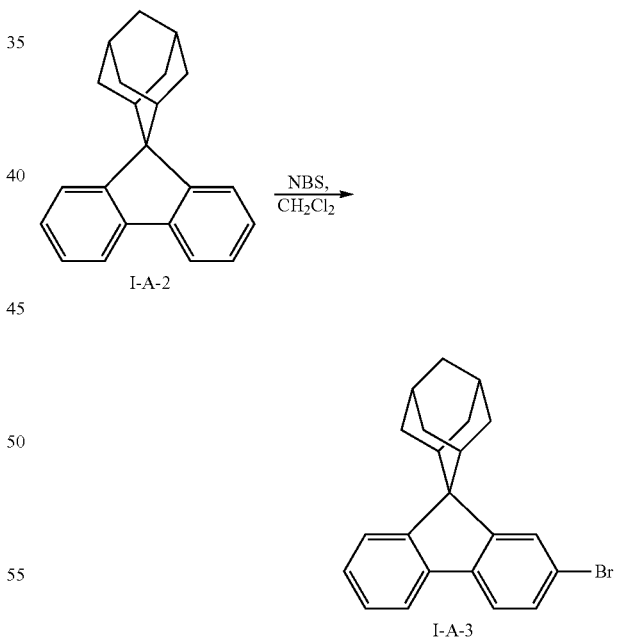

The intermediate I-A-2 (36 g, 125.6 mmol), N-bromosuccinimide (26.84 g, 150.82 mmol) and dichloromethane (800 mL) were added to a round-bottom flask, and stirred for 5 h under nitrogen protection; then liquid separation was performed, the obtained organic phases were dried by anhydrous magnesium sulfate, filtered and treated under reduced pressure to remove the solvent, thus obtaining a white solid intermediate I-A-3 (38.9 g, yield: 85.2%).

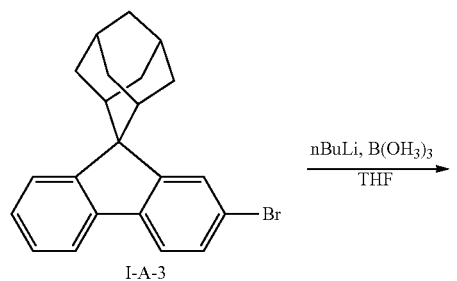

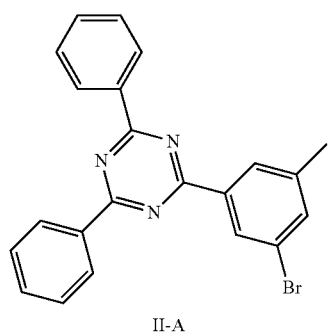

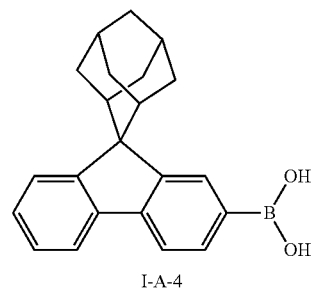

The intermediate I-A-3 (38 g, 104.0 mmol) was added to a round-bottom flask, and 600 mL tetrahydrofuran (THF) was added to the flask after the water removal; then the system was cooled within −80° C. to −90° C. with liquid nitrogen, dropwise addition of n-butyllithium (nBuLi, 6.66 g, 104.0 mmol) was started, and then, the obtained solution was thermally insulated for 1 h. Trimethyl borate (14.05 g, 135.2 mmol) was added dropwisely and thermally insulated within −80° C. to −90° C., after dropping, the solution was thermally insulated for 1 h, and naturally warmed to room temperature, and the reaction was ended, then HCl aqueous solution was added and stirred for 0.5 h. Dichloromethane and water were added for liquid separation and extraction; the obtained organic phases were washed until pH=7; then the organic phases were combined and dried for 10 min with anhydrous MgSO$_4$, and filtered, and filtrate was rotary dried and pulped with n-heptane for twice to obtain a white solid intermediate I-A-4 (22.32 g, yield: 65.21%).

2-chloro-4,6-diphenyl-1,3,5-triazine (6 g, 22.4 mmol), 3-bromo-5-methylphenyl boric acid (5.29 g, 24.6 mmol), tetra(triphenylphosphine) palladium (1.29 g, 1.12 mmol), potassium carbonate (6.19 g, 44.8 mmol), tetrabutylammonium chloride (0.30 g, 1.12 mmol), toluene (PhMe, 50 mL), ethanol (25 mL) and deionized water (12 mL) were added to a three-necked flask, and warmed to 76° C. under nitrogen protection, then heated for reflux and stirred for 6 h. At the end of the reaction, the solution was cooled to room temperature; toluene and water were added for extracting the reaction solution, then the organic phases obtained were combined, dried by anhydrous magnesium sulfate and filtered, and concentrated; the crude product was purified by silica gel column chromatography to obtain an intermediate II-A (7.07 g, 78.56%).

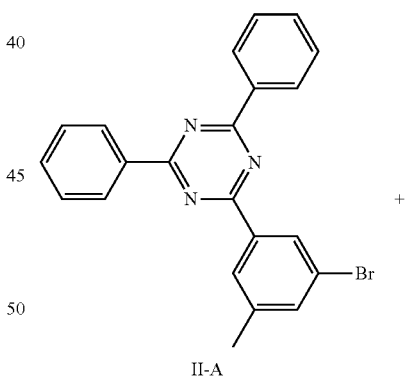

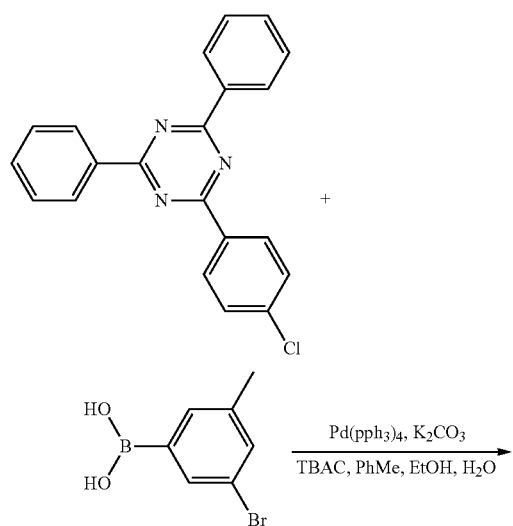

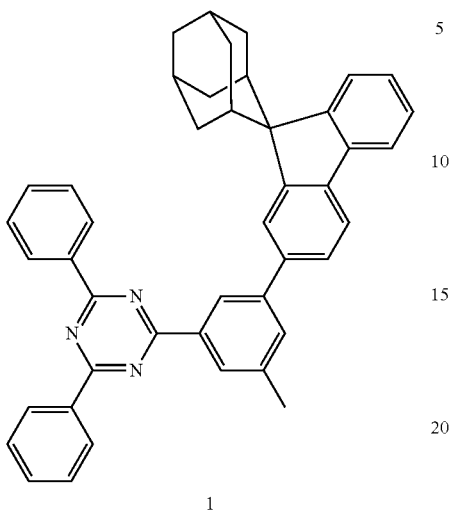

1

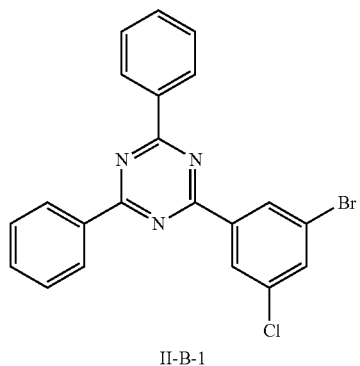

II-B-1

The intermediate II-A (2.5 g, 6.21 mmol), intermediate I-A-4 (2.25 g, 6.83 mmol), tetra(triphenylphosphine)palladium (0.36 g, 0.31 mmol), potassium carbonate (1.72 g, 12.42 mmol), tetrabutylammonium chloride (0.08 g, 0.31 mmol), toluene (24 mL), ethanol (12 mL) and deionized water (6 mL) were added to a three-necked flask, and warmed to 76° C. under nitrogen protection, then heated for reflux and stirred for 8 h. At the end of the reaction, the solution was cooled to room temperature to separate out the reaction solid, then filtered by suction, the remainder was rinsed with water, then ethanol was added to remove the water to obtain a yellow solid, which was recrystallized with toluene to obtain a solid compound 1 (3.16 g, yield: 84.52%). Mass spectrum: m/z=608.30 (M+H)$^+$.

2-chloro-4,6-diphenyl-1,3,5-triazine (20 g, 74.70 mmol), 3-bromo-5-chlorophenylboronic acid (21.09 g, 89.64 mmol), tetra(triphenylphosphine) palladium (4.32 g, 3.73 mmol), potassium carbonate (20.64 g, 149.41 mmol), tetrabutylammonium chloride (1.01 g, 3.73 mmol), toluene (24 mL), ethanol (12 mL) and deionized water (6 mL) were added to a three-necked flask, and warmed to 76° C. under nitrogen protection, then heated for reflux and stirred for 8 h. At the end of the reaction, the solution was cooled to room temperature to separate out the reaction solid, then filtered by suction, the remainder was rinsed with water, then ethanol was added to remove the water to obtain a gray solid, the crude product was purified by silica gel column chromatography to obtain an intermediate II-B-1 (25.88 g, yield: 82.10%).

Synthesis of Compound 2

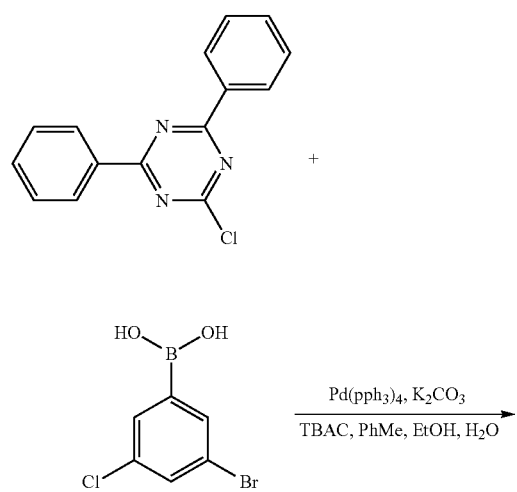

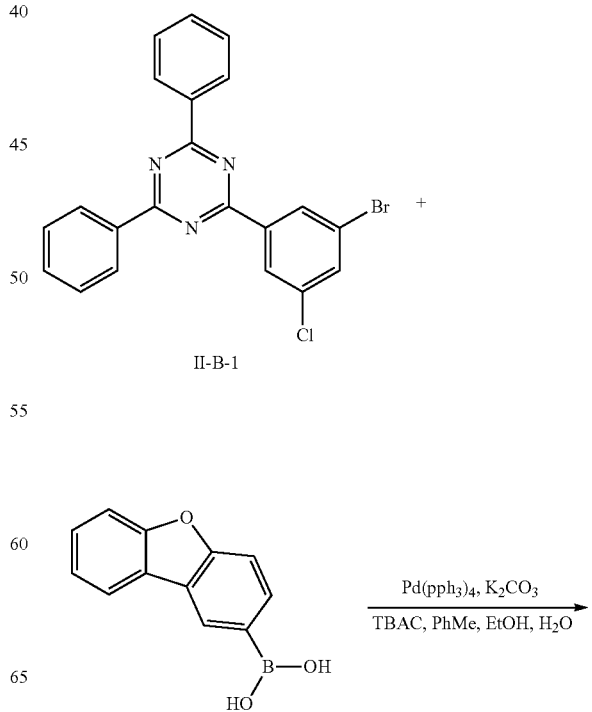

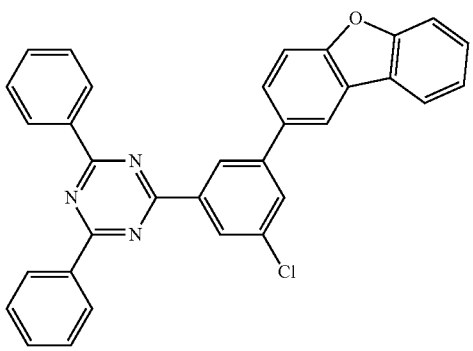

II-B

The intermediate II-B-1 (6 g, 14.19 mmol), dibenzofuran-2-boric acid (3.61 g, 17.03 mmol), tetra(triphenylphosphine)palladium (0.82 g, 0.71 mmol), potassium carbonate (3.92 g, 28.39 mmol), tetrabutylammonium chloride (0.19 g, 0.71 mmol), toluene (48 mL), ethanol (24 mL) and deionized water (12 mL) were added to a three-necked flask, and warmed to 76° C. under nitrogen protection, then heated for reflux and stirred for 7 h. At the end of the reaction, the solution was cooled to room temperature to separate out the reaction solid; then filtered by suction, the remainder was rinsed with water, then ethanol was added to remove the water to obtain a solid crude product, and the crude product was purified by silica gel column chromatography to obtain an intermediate II-B (6.23 g, yield: 86.21%).

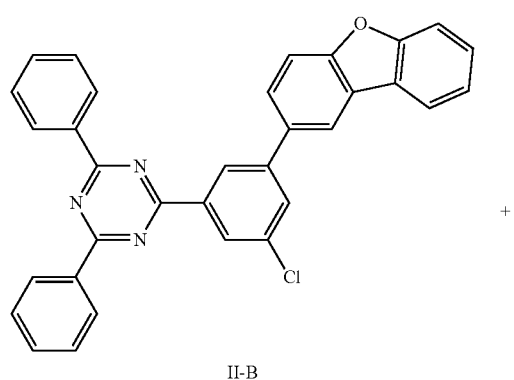

II-B

+

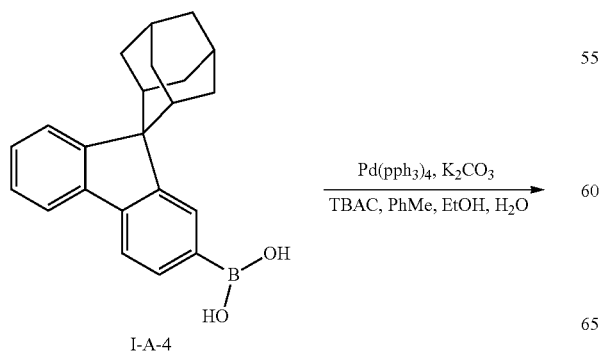

I-A-4

$\xrightarrow[\text{TBAC, PhMe, EtOH, H}_2\text{O}]{\text{Pd(pph}_3)_4, \text{K}_2\text{CO}_3}$

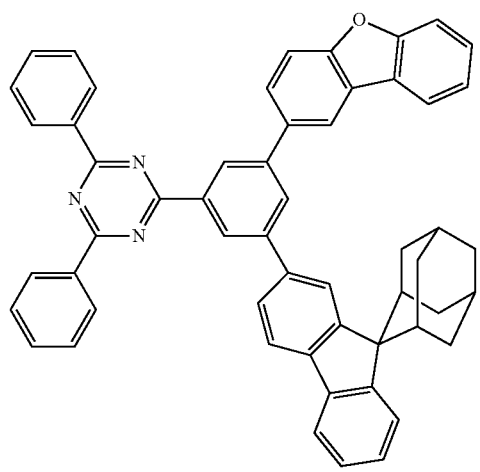

2

The intermediate II-B (6 g, 11.76 mmol), intermediate I-A-4 (4.27 g, 12.94 mmol), tetra(triphenylphosphine)palladium (0.68 g, 0.58 mmol), potassium carbonate (3.25 g, 23.53 mmol), tetrabutylammonium chloride (0.16 g, 0.58 mmol), toluene (48 mL), ethanol (24 mL) and deionized water (12 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a gray solid crude product, and the crude product was purified by silica gel column chromatography to obtain a compound 2 (7.11 g, yield: 79.56%). Mass spectrum: m/z=760.32 (M+H)⁺.

Synthesis of Compound 3

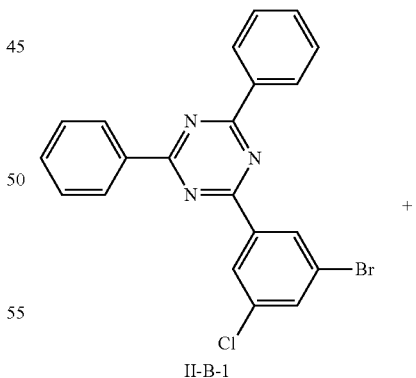

II-B-1

+

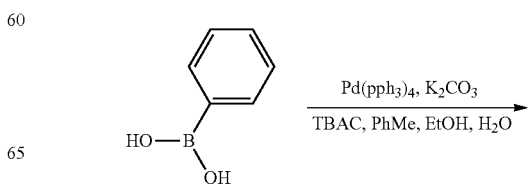

$\xrightarrow[\text{TBAC, PhMe, EtOH, H}_2\text{O}]{\text{Pd(pph}_3)_4, \text{K}_2\text{CO}_3}$

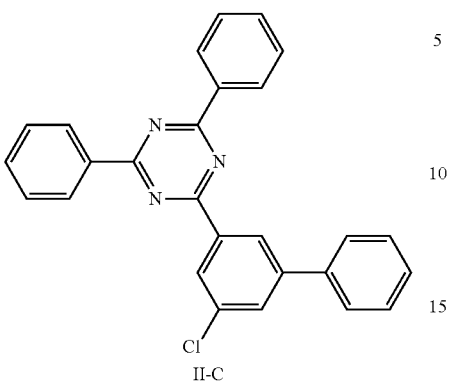

II-C

The intermediate II-B-1 (6 g, 14.19 mmol), phenylboronic acid (1.9 g, 15.61 mmol), tetra(triphenylphosphine)palladium (0.32 g, 0.28 mmol), potassium carbonate (3.92 g, 28.38 mmol), tetrabutylammonium chloride (0.19 g, 0.70 mmol), toluene (48 mL), ethanol (24 mL) and deionized water (12 mL) were added to a three-necked flask, and warmed to 76° C. under nitrogen protection, then heated for reflux and stirred for 7 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was purified by recrystallized with a dichloromethane/n-heptane system to obtain an intermediate II-C (4.82 g, yield: 81.10%).

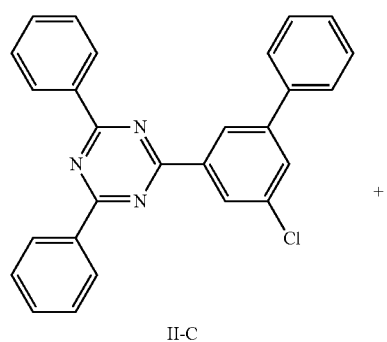

II-C

+

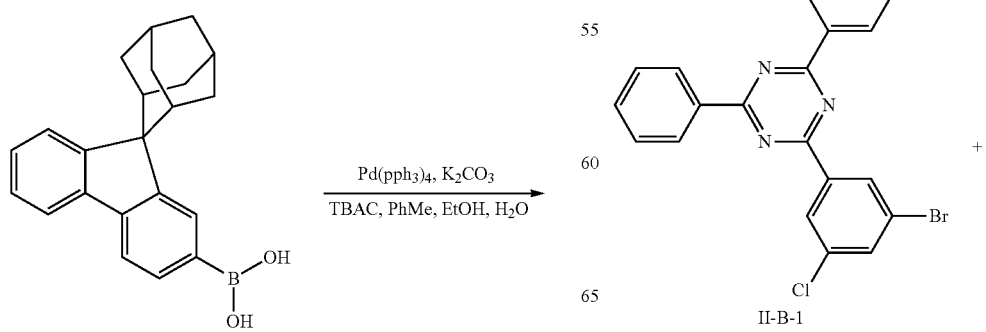

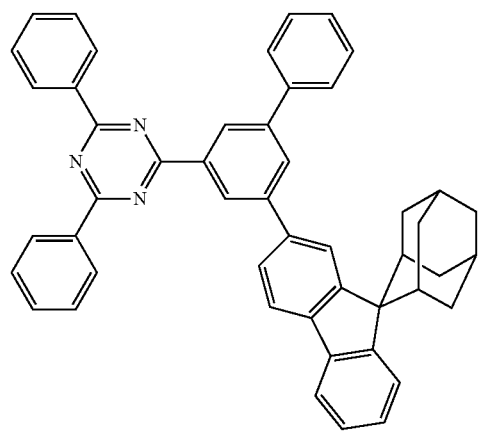

3

The intermediate II-C (4.5 g, 10.71 mmol), intermediate I-A-4 (3.89 g, 11.78 mmol), tetra(triphenylphosphine)palladium (0.24 g, 0.21 mmol), potassium carbonate (2.76 g, 21.43 mmol), tetrabutylammonium chloride (0.15 g, 0.53 mmol), toluene (24 mL), ethanol (12 mL) and deionized water (6 mL) were added to a three-necked flask, and warmed to 76° C. under nitrogen protection, then heated for reflux and stirred for 7 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was purified by silica gel column chromatography to obtain a compound 3 (5.17 g, yield: 72.00%). Mass spectrum: m/z=670.31 (M+H)$^+$. Hydrogen Nuclear Magnetic Resonance Spectrum ($^1$H HNMR) data, $^1$H NMR (CDCl$_3$, 400 MHz): 9.13 (s, 1H), 8.97 (s, 1H), 8.82 (d, 4H), 8.60 (s, 1H), 8.17 (d, 1H), 8.11 (s, 1H), 7.94 (d, 1H), 7.87 (d, 1H), 7.84-7.80 (m, 3H), 7.64 (t, 2H), 7.61-7.56 (m, 6H), 7.47 (t, 1H), 7.42 (t, 1H), 7.34 (t, 1H), 3.18 (d, 2H), 3.01 (d, 2H), 2.36 (s, 1H), 2.27 (s, 1H), 2.07 (s, 2H), 1.94 (d, 2H), 1.87 (d, 2H), and 1.76 (s, 2H).

Synthesis of Compound 4

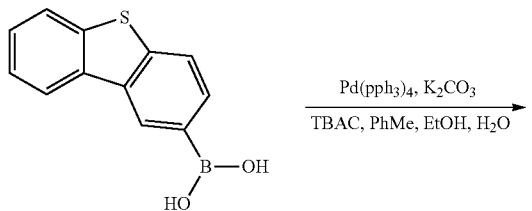

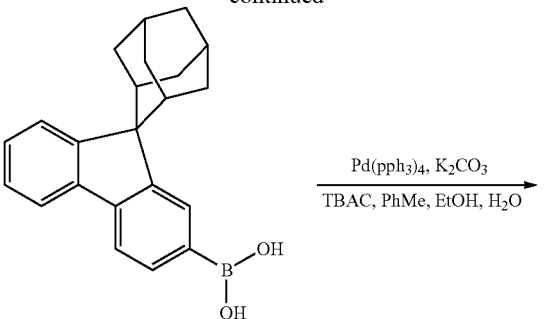

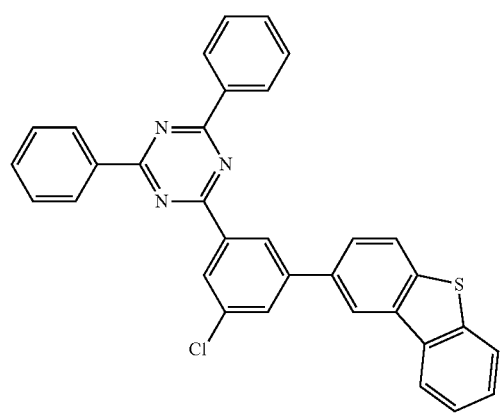

II-D

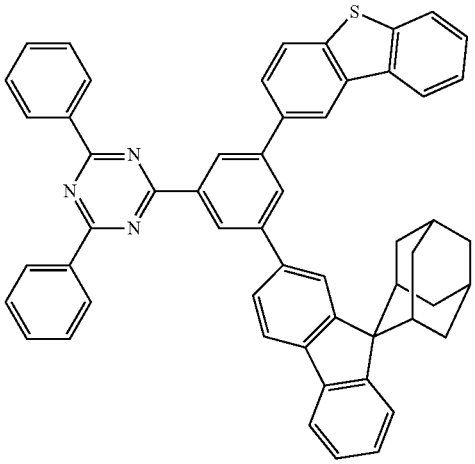

4

The intermediate II-B-1 (5 g, 11.83 mmol), dibenzofuran-2-boric acid (2.75 g, 12.06 mmol), tetra(triphenylphosphine) palladium (0.68 g, 0.59 mmol), potassium carbonate (3.19 g, 23.65 mmol), tetrabutylammonium chloride (0.16 g, 0.59 mmol), toluene (40 mL), ethanol (20 mL) and deionized water (10 mL) were added to a three-necked flask, and warmed to 76° C. under nitrogen protection, then heated for reflux and stirred for 7 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was purified by silica gel column chromatography to obtain a white solid intermediate II-D (4.61 g, yield: 74.12%).

The intermediate II-D (4.5 g, 8.55 mmol), intermediate I-A-4 (2.88 g, 8.72 mmol), tetra(triphenylphosphine) palladium(0.49 g, 0.42 mmol), potassium carbonate (2.36 g, 17.10 mmol), tetrabutylammonium chloride (0.11 g, 0.42 mmol), toluene (40 mL), ethanol (20 mL) and deionized water (10 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain a compound 4 (5.20 g, yield: 78.47%). Mass spectrum: m/z=776.30 (M+H)$^+$.

Synthesis of Compound 5

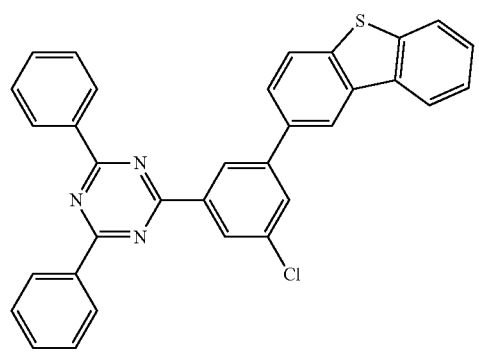

II-D

+

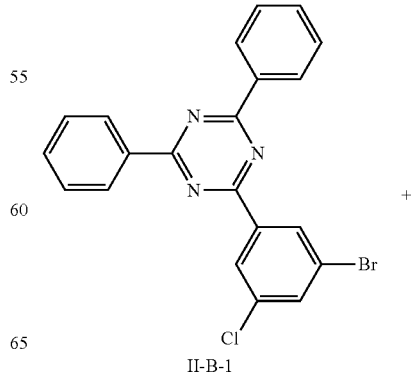

II-B-1

-continued

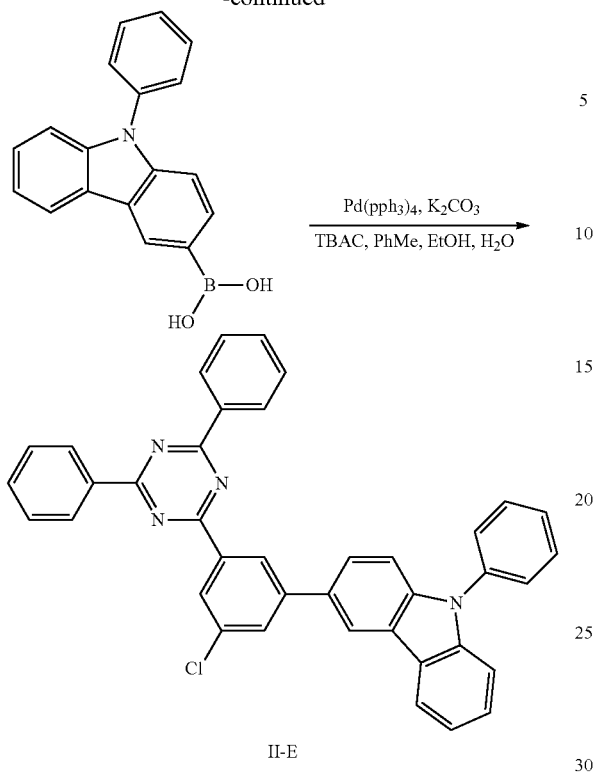

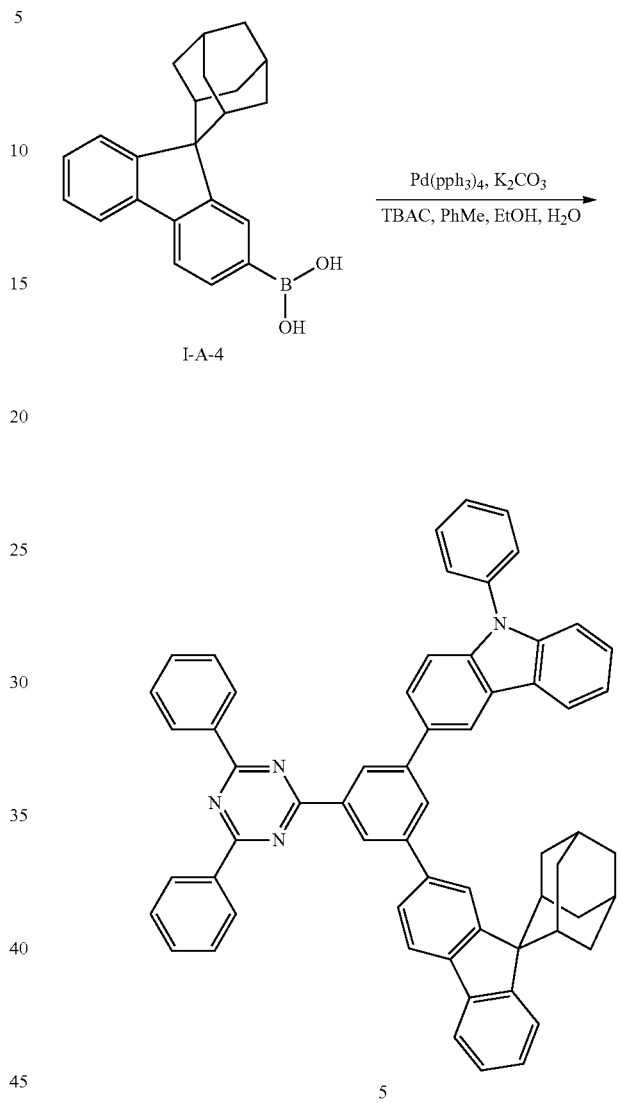

I-A-4

The intermediate II-B-1 (4 g, 9.46 mmol), N-phenyl-3-carbazole boric acid (2.77 g, 9.65 mmol), tetra(triphenylphosphine)palladium (0.55 g, 0.47 mmol), potassium carbonate (2.61 g, 18.92 mmol), tetrabutylammonium chloride (0.13 g, 0.47 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was purified by silica gel column chromatography to obtain an intermediate II-E (4.20 g, yield: 76.12%).

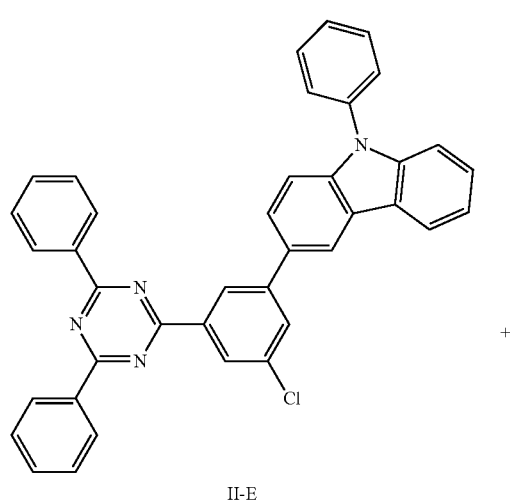

II-E

+

The intermediate II-E (4.0 g, 6.83 mmol), intermediate I-A-4 (2.00 g, 6.97 mmol), tetra(triphenylphosphine)palladium (0.39 g, 0.34 mmol), potassium carbonate (1.88 g, 13.67 mmol), tetrabutylammonium chloride (0.09 g, 0.34 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was purified by silica gel column chromatography to obtain a compound 5 (4.52 g, yield: 79.46%). Mass spectrum: m/z=835.37 (M+H)$^+$.

Synthesis of Compound 6

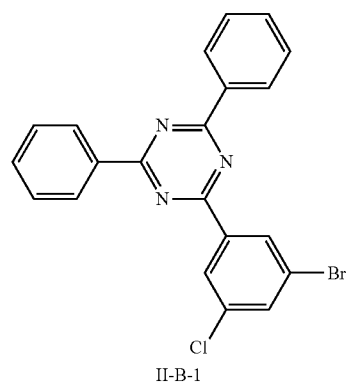
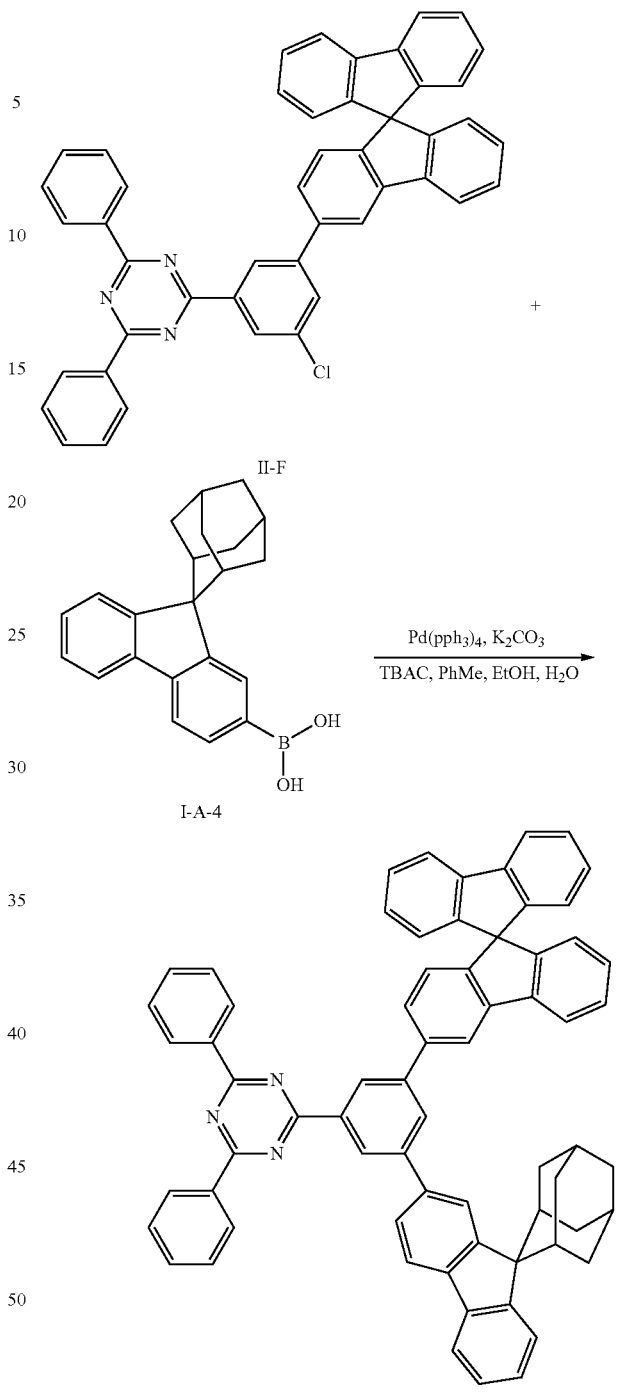

The intermediate II-B-1 (5.5 g, 13.01 mmol), 9,9'-spirobi[9H-fluorene]-2-boronic acid (4.80 g, 13.27 mmol), tetra(triphenylphosphine)palladium (0.75 g, 0.65 mmol), potassium carbonate (3.59 g, 26.02 mmol), tetrabutylammonium chloride (0.18 g, 0.65 mmol), toluene (44 mL), ethanol (22 mL) and deionized water (11 mL) were added to a three-necked flask, and warmed to 76° C. under nitrogen protection, then heated for reflux and stirred for 5 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was purified by silica gel column chromatography to obtain an intermediate II-F (6.99 g, yield: 81.46%).

The intermediate II-F (5.0 g, 7.57 mmol), intermediate I-A-4 (2.62 g, 7.95 mmol), tetra(triphenylphosphine) palladium(0.43 g, 0.37 mmol), potassium carbonate (2.09 g, 15.14 mmol), tetrabutylammonium chloride (0.10 g, 0.37 mmol), toluene (40 mL), ethanol (20 mL) and deionized water (10 mL) were added to a three-necked flask, and warmed to 76° C. under nitrogen protection, then heated for reflux and stirred for 4 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain a compound 6 (5.20 g, yield: 75.49%). Mass spectrum: m/z=908.39 (M+H)⁺.

Synthesis of Compound 7

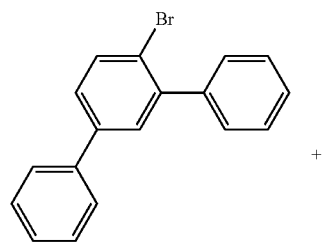

+

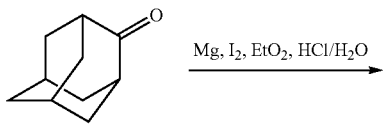

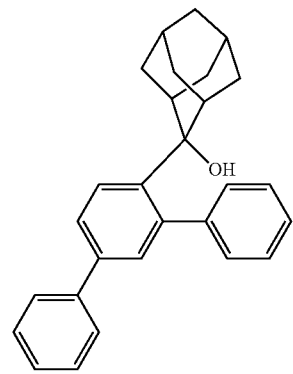

I-B-1

Magnesium strips (14.90 g, 620.93 mmol) and diethyl ether (120 mL) were placed in a round-bottom flask under nitrogen protection, and iodine (103.42 g, 407.49 mmol) was added. Afterwards, a diethyl ether solution (220 mL) dissolved with 1-bromo-2,4-bi(phenyl)benzene (60.00 g, 194.04 mmol) was slowly dropped in the flask, at the end of dropping, the solution was warmed to 35° C. and stirred for 3 h; then the reaction solution was cooled to 0° C., and a diethyl ether solution (220 mL) dissolved with adamantanone (46.63 g, 310.46 mmol) was dropped slowly, at the end of dropping, the solution was warmed to 35° C. and stirred for 6 h; the reaction solution was cooled to room temperature, and 5% hydrochloric acid was added until pH<7, and stirred for 1 h, then diethyl ether (200 mL) was added for extraction, the organic phases obtained were combined, and dried by anhydrous magnesium sulfate, then filtered and treated under reduced pressure to remove the solvent; the obtained crude product was purified by silica gel column chromatography with ethyl acetate/n-heptane (1:2) as a mobile phase to obtain a white solid intermediate I-B-1 (45.40 g, yield: 61.49%).

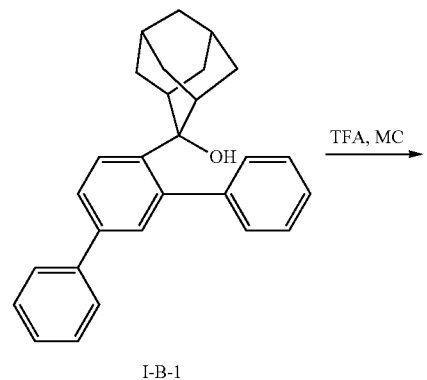

I-B-1

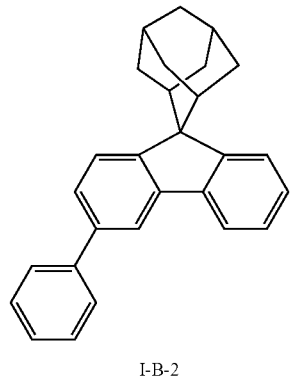

I-B-2

The intermediate I-B-1 (43 g, 113 mmol), trifluoroacetic acid (36.93 g, 348 mmol) and dichloromethane (300 mL) were added to a round-bottom flask, and stirred for 2 h under nitrogen protection; afterwards, aqueous solution of sodium hydroxide was added to the reaction solution until pH=8, and liquid separation was performed; the obtained organic phase was dried by anhydrous magnesium sulfate, filtered and treated under reduced pressure to remove the solvent; the obtained crude product was purified by silica gel column chromatography with dichloromethane/n-heptane (1:2) to obtain a white solid intermediate I-B-2 (39.2 g, yield: 96.3%).

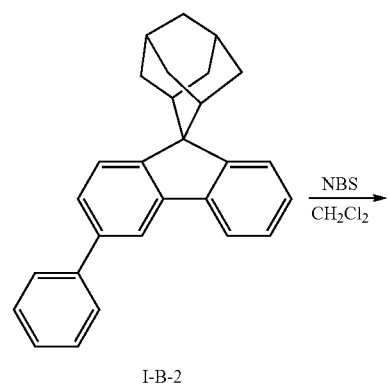

I-B-2

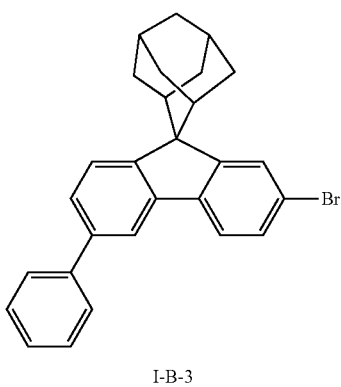

I-B-3

The intermediate I-B-2 (41.0 g, 113 mmol), N-bromosuccinimide (24.1 g, 135.7 mmol) and dichloromethane (800 mL) were added to a round-bottom flask, and stirred for 5 h under nitrogen protection; liquid separation was performed; the obtained organic phase was dried by anhydrous magnesium sulfate, filtered and treated under reduced pressure to remove the solvent, thus obtaining a white solid intermediate I-B-3 (42.5 g, yield: 85.2%).

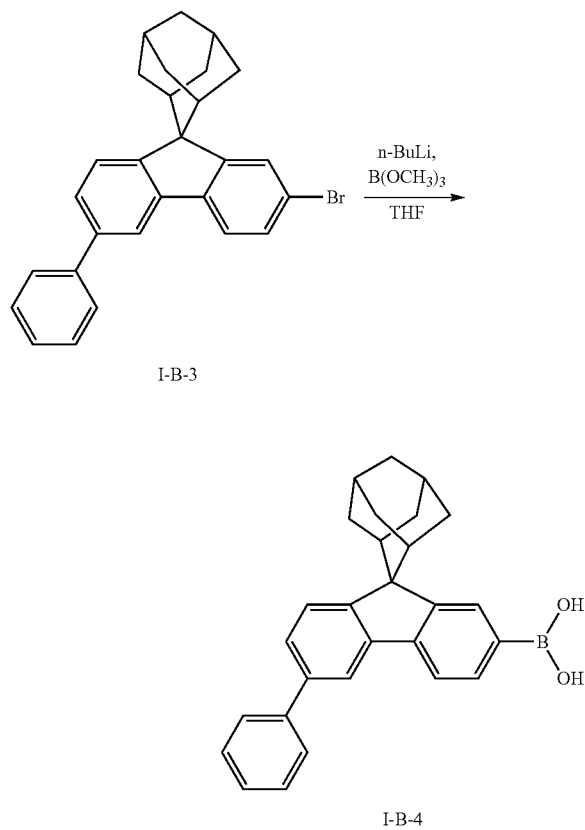

I-B-3

I-B-4

The intermediate I-B-3 (41.5 g, 94.01 mmol) was added to a round-bottom flask, and 630 mL THF was added to the flask after the water removal; then the system was cooled to −80° C. to −90° C. with liquid nitrogen, dropwise addition of n-butyllithium (6.02 g, 94.01 mmol) was started, and then, the obtained solution was thermally insulated for 1 h. Trimethyl borate (12.70 g, 122.22 mmol) was added dropwisely and thermally insulated within −80° C. to −90° C., after dropping, the solution was thermally insulated for 1 h, and naturally warmed to room temperature, and the reaction was ended, then HCl aqueous solution was added and stirred for 0.5 h. Dichloromethane and water were added for liquid separation and extraction; the obtained organic phases were washed until pH=7; then the organic phases were combined and dried for 10 min with anhydrous MgSO$_4$, and filtered, and the filtrate was rotary dried and pulped with n-heptane for twice to obtain a white solid intermediate I-B-4 (26.78 g, yield: 70.12%).

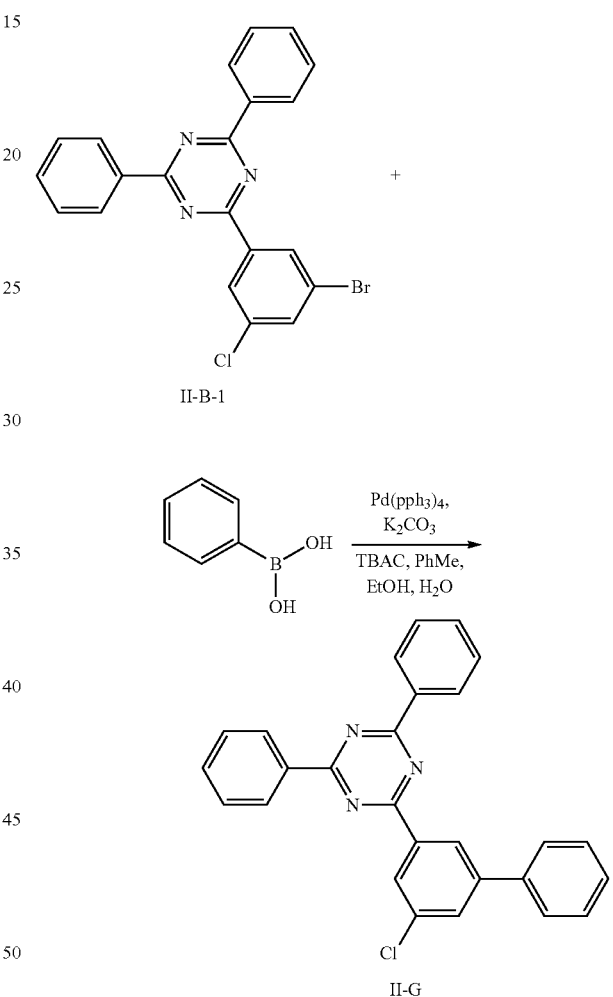

II-B-1

II-G

The intermediate II-B-1 (5.4 g, 12.81 mmol), phenylboronic acid (1.59 g, 13.06 mmol), tetra(triphenylphosphine) palladium (0.74 g, 0.64 mmol), potassium carbonate (3.54 g, 25.62 mmol), tetrabutylammonium chloride (0.17 g, 0.64 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-G (4.42 g, yield: 82.10%).

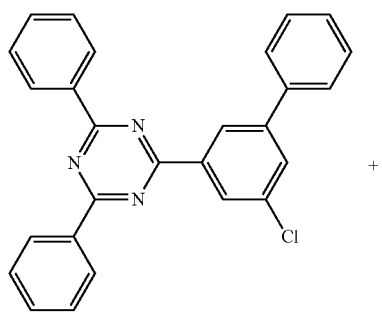

II-G

+

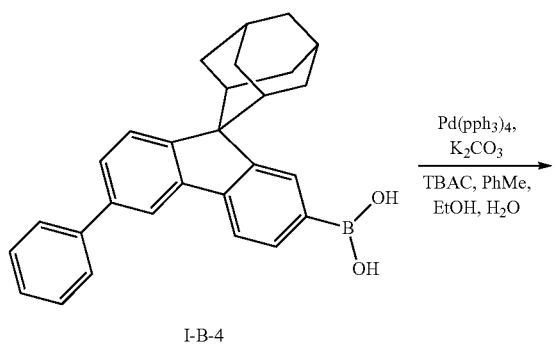

I-B-4

Pd(pph₃)₄,
K₂CO₃
───────────→
TBAC, PhMe,
EtOH, H₂O

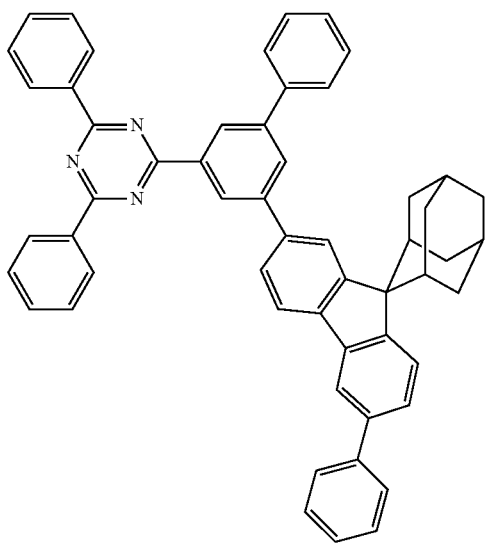

7

The intermediate II-G (4 g, 9.54 mmol), intermediate I-B-4 (3.95 g, 9.73 mmol), tetra(triphenylphosphine)palladium (0.55 g, 0.47 mmol), potassium carbonate (2.63 g, 19.09 mmol), tetrabutylammonium chloride (0.13 g, 0.47 mmol), toluene (32 mL), ethanol (16 mL) and deionized water (8 mL) were added to a three-necked flask, and warmed to 76° C. under nitrogen protection, then heated for reflux and stirred for 6 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was purified by silica gel column chromatography to obtain a compound 7 (5.31 g, yield: 74.63%). Mass spectrum: m/z=746.35 (M+H)⁺.

Synthesis of Compound 8

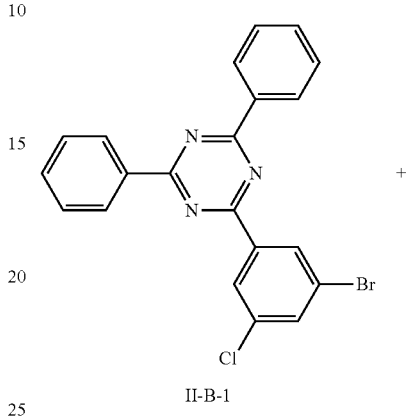

II-B-1

+

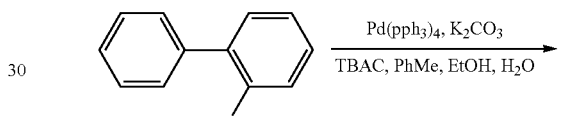

Pd(pph₃)₄, K₂CO₃
──────────────→
TBAC, PhMe, EtOH, H₂O

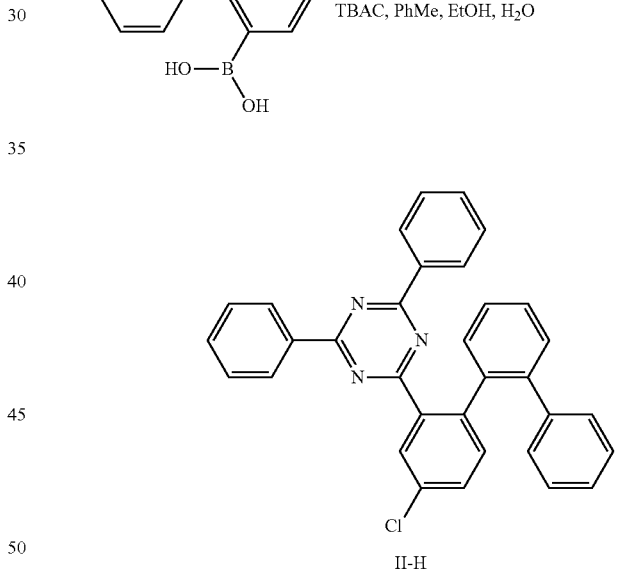

II-H

The intermediate II-B-1 (5.0 g, 11.82 mmol), 2-biphenyl boric acid (2.81 g, 14.19 mmol), tetra(triphenylphosphine) palladium (0.27 g, 0.23 mmol), potassium carbonate (3.27 g, 23.65 mmol), tetrabutylammonium chloride (0.16 g, 0.59 mmol), toluene (40 mL), ethanol (20 mL) and deionized water (10 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-H (4.16 g, yield: 71.89%).

Synthesis of Compound 9

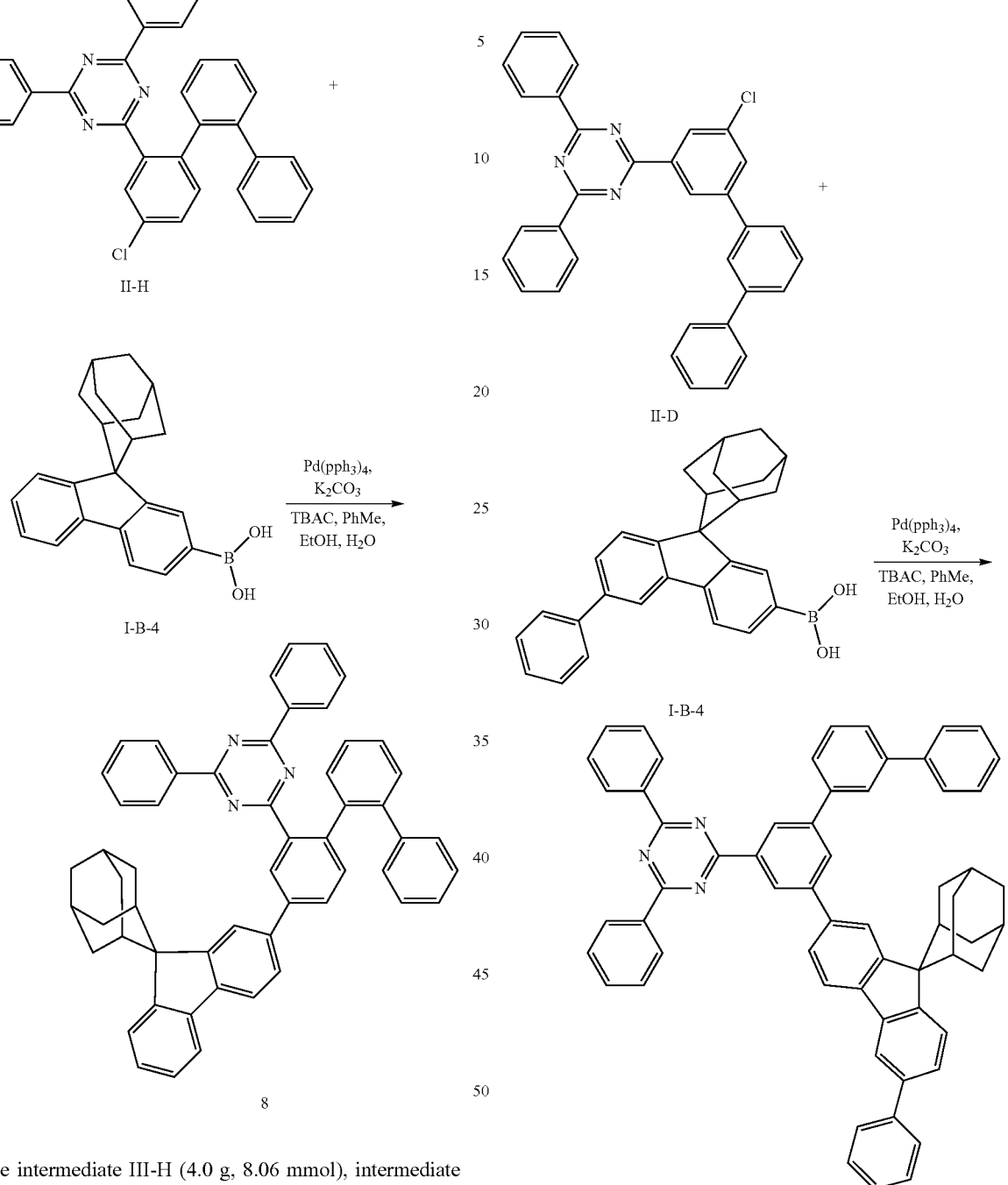

The intermediate III-H (4.0 g, 8.06 mmol), intermediate I-B-4 (3.19 g, 9.67 mmol), tetra(triphenylphosphine)palladium (0.16 g, 0.18 mmol), potassium carbonate (2.23 g, 16.12 mmol), tetrabutylammonium chloride (0.18 g, 0.16 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain a compound 8 (4.4 g, yield: 73.87%). Mass spectrum: m/z=746.35 (M+H)$^+$.

The intermediate II-D (3.5 g, 7.06 mmol), intermediate I-B-4 (2.78 g, 6.85 mmol), tetra(triphenylphosphine)palladium (0.37 g, 0.32 mmol), potassium carbonate (1.80 g, 13.05 mmol), tetrabutylammonium chloride (0.09 g, 0.33 mmol), toluene (28 mL), ethanol (14 mL) and deionized water (7 mL) were added to a three-necked flask, and warmed to 76° C. under nitrogen protection, then heated for reflux and stirred for 7 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was purified by silica gel column chromatography to obtain a compound 9 (4.36 g, yield: 75.86%). Mass spectrum: m/z=822.38 (M+H)$^+$.

Synthesis of Compound 10

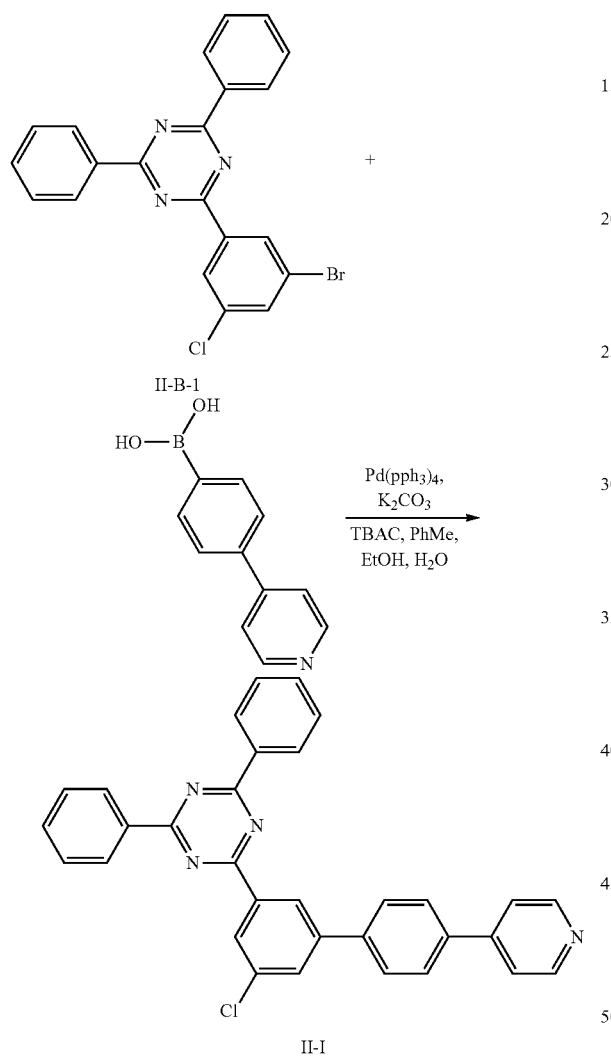

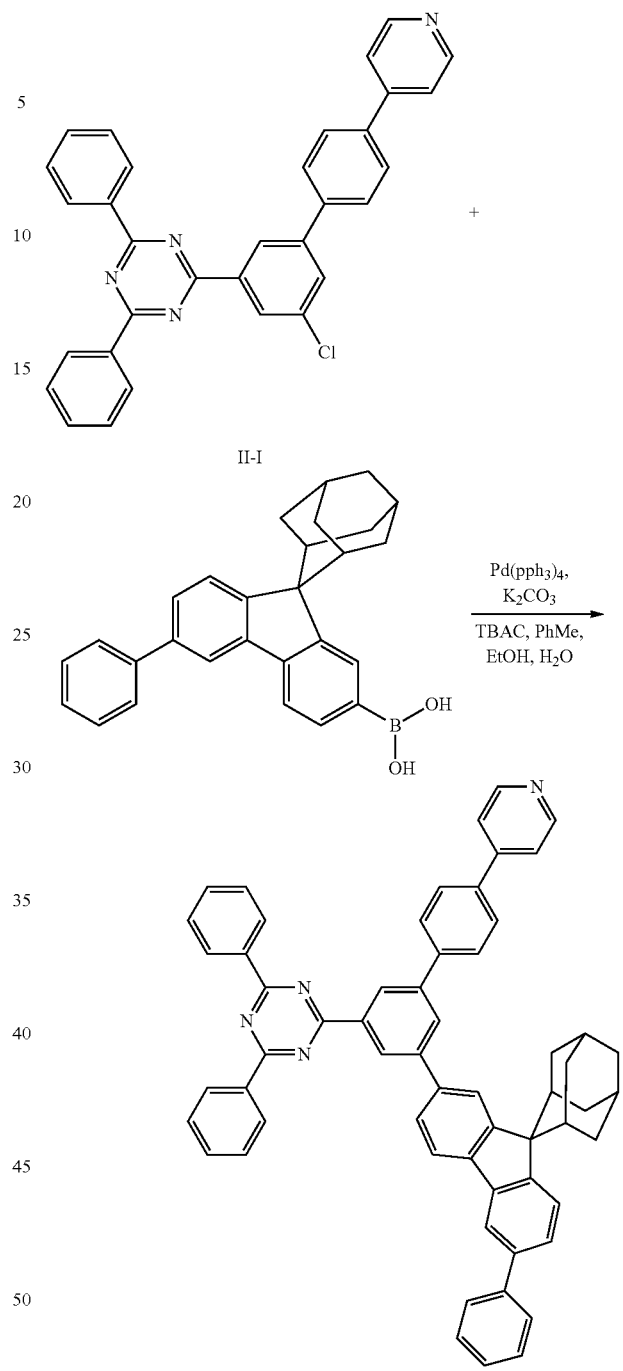

The intermediate II-B-1 (4.00 g, 9.47 mmol), 4-(4-pyridyl)phenylboronic acid (1.92 g, 9.66 mmol), tetra(triphenylphosphine)palladium (0.54 g, 0.47 mmol), potassium carbonate (2.62 g, 18.94 mmol), tetrabutylammonium chloride (0.13 g, 0.47 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-I (3.61 g, yield: 76.84%).

The intermediate II-I (3.50 g, 7.04 mmol), intermediate I-B-4 (2.91 g, 7.18 mmol), tetra(triphenylphosphine)palladium (0.40 g, 0.35 mmol), potassium carbonate (1.94 g, 14.08 mmol), tetrabutylammonium chloride (0.09 g, 0.35 mmol), toluene (28 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain a compound 10 (4.32 g, yield: 74.75%). Mass spectrum: m/z=823.37 (M+H)⁺.

Synthesis of Compound 11

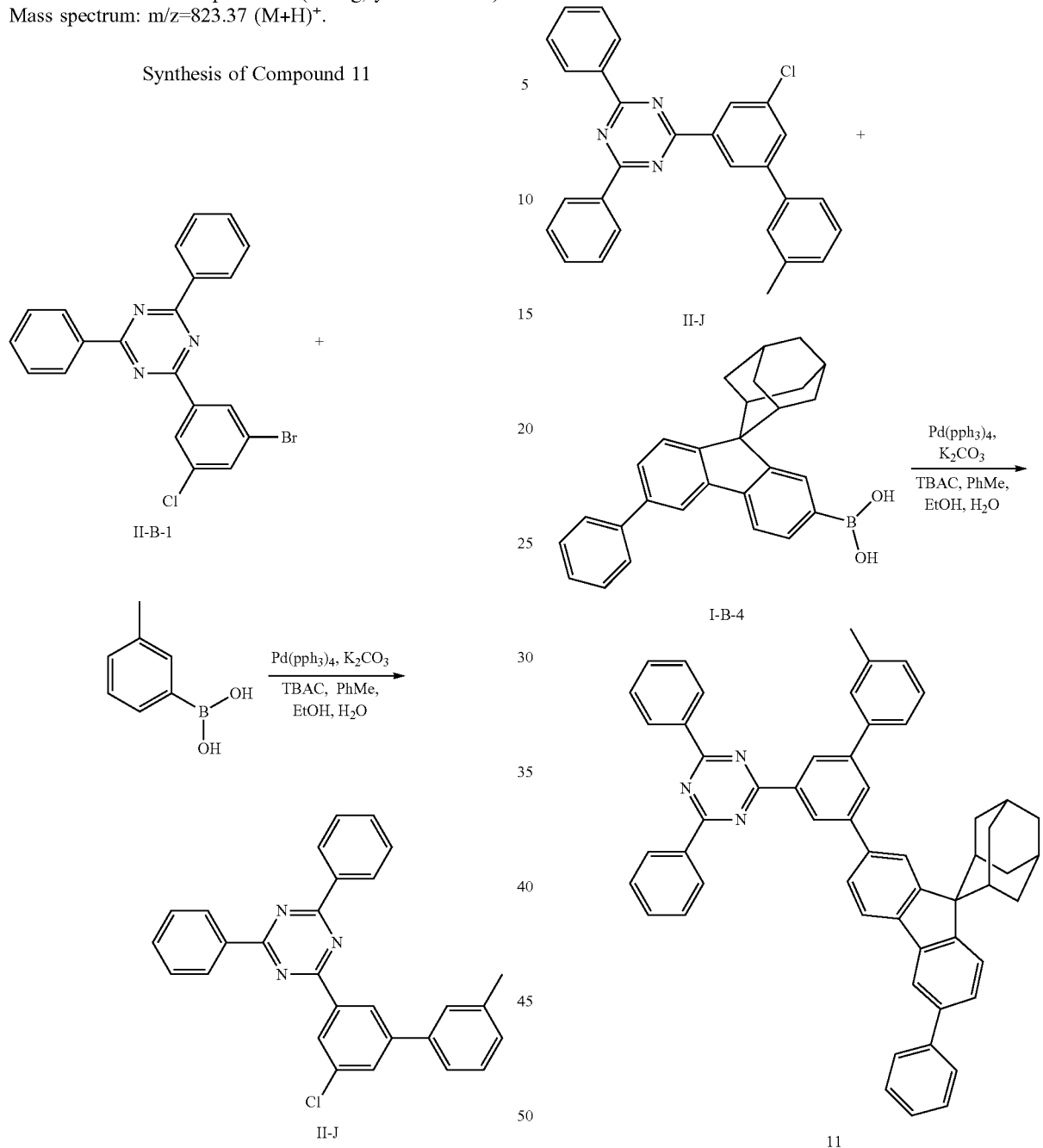

The intermediate II-B-1 (4.00 g, 9.46 mmol), 3-methylphenylboronic acid (1.35 g, 9.93 mmol), tetra(triphenylphosphine)palladium (0.54 g, 0.47 mmol), potassium carbonate (2.61 g, 18.92 mmol), tetrabutylammonium chloride (0.13 g, 0.47 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-J (3.21 g, yield: 76.85%).

The intermediate II-J (3.00 g, 6.91 mmol), intermediate I-B-4 (3.09 g, 7.60 mmol), tetra(triphenylphosphine)palladium (0.39 g, 0.34 mmol), potassium carbonate (1.91 g, 13.82 mmol), tetrabutylammonium chloride (0.09 g, 0.34 mmol), toluene (24 mL), ethanol (12 mL) and deionized water (6 mL) were added to a three-necked flask, and warmed to 76° C. under nitrogen protection, then heated for reflux and stirred for 7 h. At the end of the reaction, the solution was cooled to room temperature to separate out the reaction solid; then filtered by suction, the remainder was rinsed with water, then ethanol was added to remove the water to obtain a white solid, which was recrystallized with toluene to obtain a compound 11 (4.21 g, yield: 80.23%). Mass spectrum: m/z=760.36 (M+H)⁺.

Synthesis of Compound 12

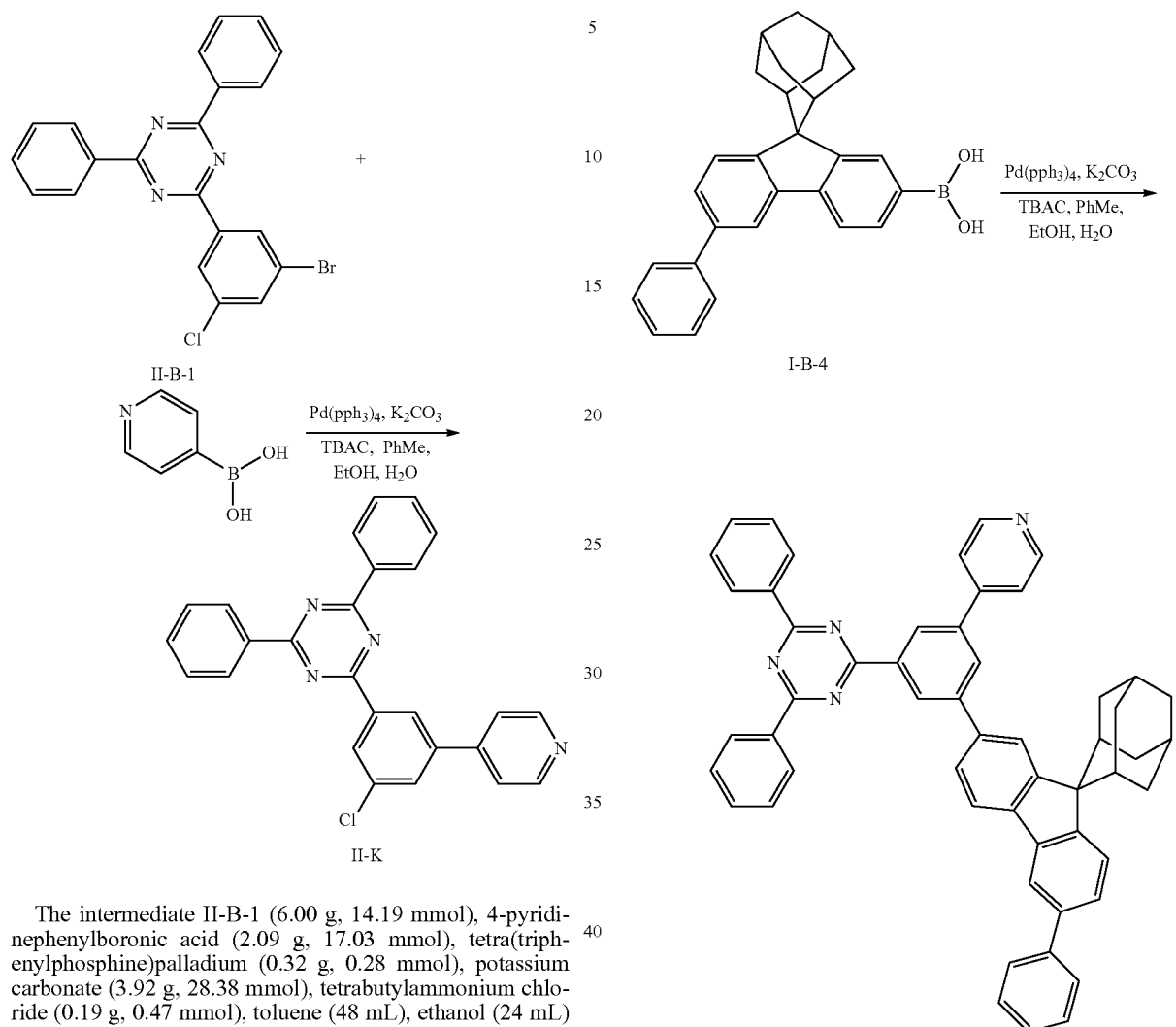

The intermediate II-B-1 (6.00 g, 14.19 mmol), 4-pyridinephenylboronic acid (2.09 g, 17.03 mmol), tetra(triphenylphosphine)palladium (0.32 g, 0.28 mmol), potassium carbonate (3.92 g, 28.38 mmol), tetrabutylammonium chloride (0.19 g, 0.47 mmol), toluene (48 mL), ethanol (24 mL) and deionized water (12 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-K (4.39 g, yield: 73.65%).

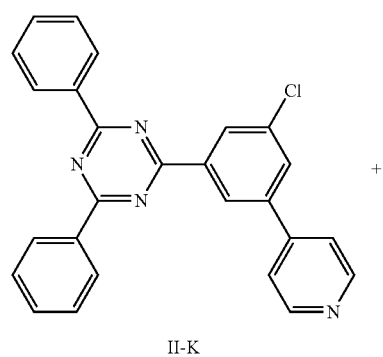

The intermediate II-K (4.00 g, 9.50 mmol), intermediate I-B-4 (4.24 g, 10.45 mmol), tetra(triphenylphosphine) palladium (0.21 g, 0.19 mmol), potassium carbonate (2.62 g, 19.00 mmol), tetrabutylammonium chloride (0.12 g, 0.44 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was recrystallized with toluene to obtain a compound 12 (5.84 g, yield: 82.46%). Mass spectrum: m/z=747.34 (M+H)$^+$.

Synthesis of Compound 13

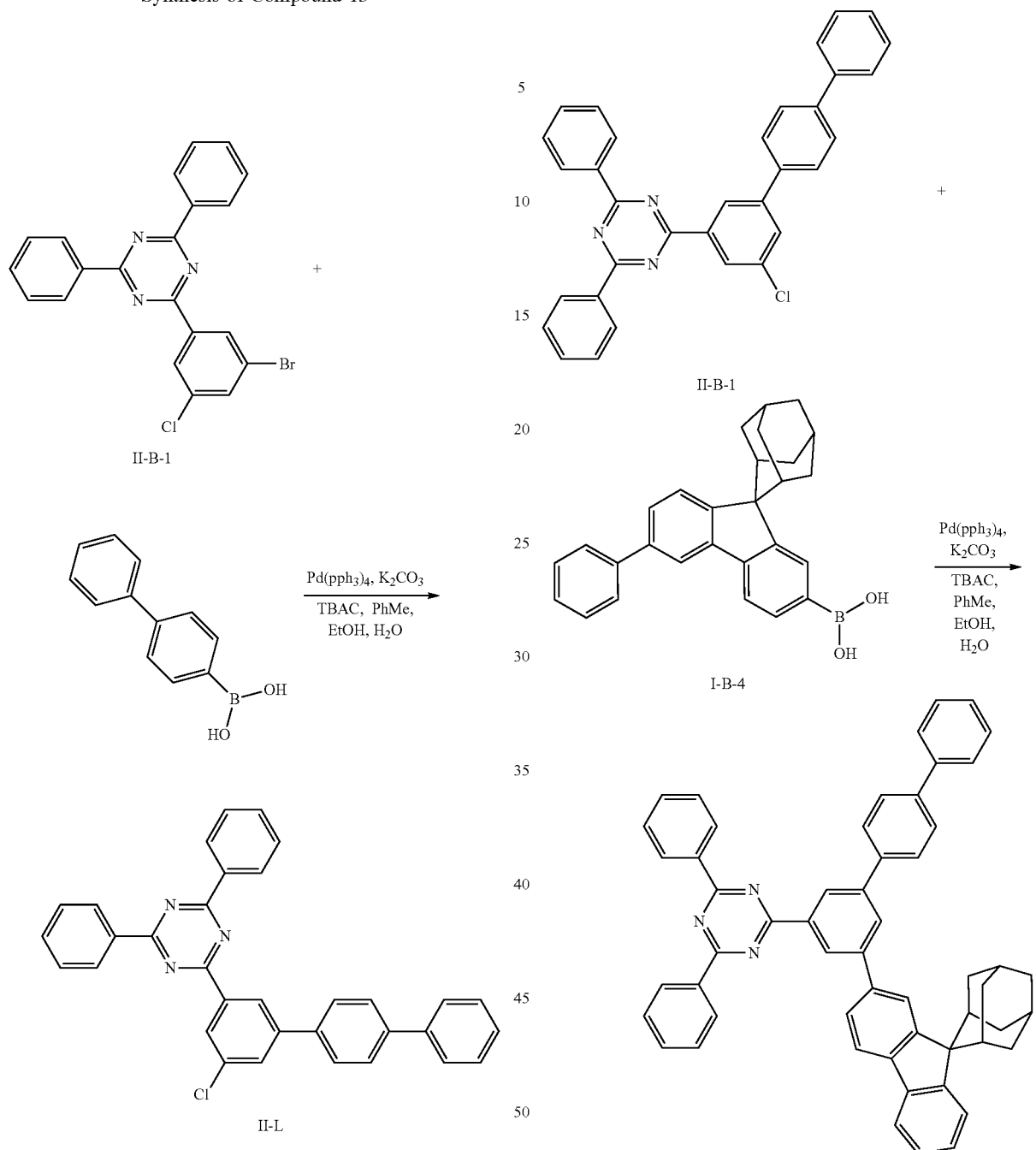

The intermediate II-B-1 (7.00 g, 16.55 mmol), 4-biphenyl boric acid (3.60 g, 18.21 mmol), tetra(triphenylphosphine) palladium (0.38 g, 0.33 mmol), potassium carbonate (4.57 g, 33.11 mmol), tetrabutylammonium chloride (0.22 g, 0.82 mmol), toluene (56 mL), ethanol (28 mL) and deionized water (14 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-L (6.52 g, yield: 79.48%).

The intermediate II-L (6.00 g, 12.09 mmol), intermediate I-B-4 (5.40 g, 13.30 mmol), tetra(triphenylphosphine)palladium (0.27 g, 0.24 mmol), potassium carbonate (3.34 g, 24.19 mmol), tetrabutylammonium chloride (0.16 g, 0.60 mmol), toluene (48 mL), ethanol (24 mL) and deionized water (12 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain a compound 13 (7.49 g, yield: 75.34%). Mass spectrum: m/z=822.38 (M+H)$^+$.

Synthesis of Compound 14

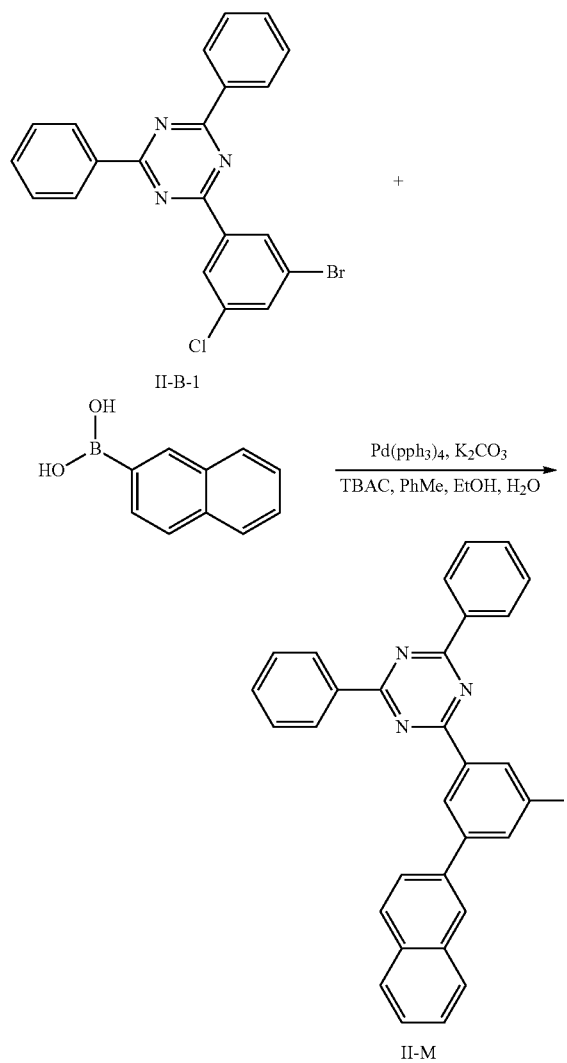

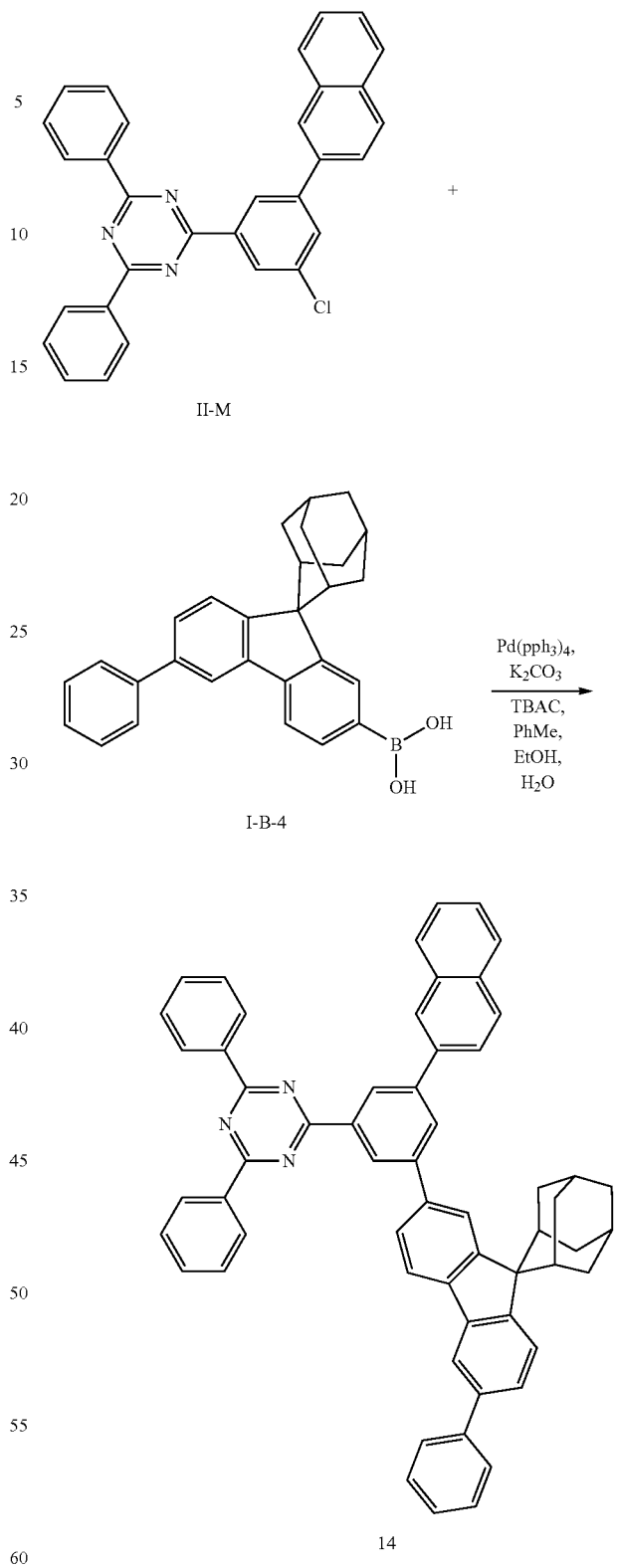

The intermediate II-B-1 (6.0 g, 14.19 mmol), 2-naphthylboronic acid (2.68 g, 15.61 mmol), tetra(triphenylphosphine)palladium (0.32 g, 0.28 mmol), potassium carbonate (3.92 g, 28.38 mmol), tetrabutylammonium chloride (0.19 g, 0.71 mmol), toluene (48 mL), ethanol (24 mL) and deionized water (12 mL) were added to a three-necked flask, and warmed to 76° C. under nitrogen protection, then heated for reflux and stirred for 5 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was purified by silica gel column chromatography to obtain an intermediate II-M (5.43 g, yield: 81.46%).

The intermediate II-M (5.0 g, 10.63 mmol), intermediate I-B-4 (4.75 g, 11.70 mmol), tetra(triphenylphosphine)palladium (0.24 g, 0.21 mmol), potassium carbonate (2.94 g, 21.27 mmol), tetrabutylammonium chloride (0.14 g, 0.53 mmol), toluene (40 mL), ethanol (20 mL) and deionized water (10 mL) were added to a three-necked flask, and warmed to 76° C. under nitrogen protection, then heated for reflux and stirred for 6 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain a compound 14 (6.10 g, yield: 72.22%). Mass spectrum: m/z=796.36 (M+H)$^+$.

Synthesis of Compound 15

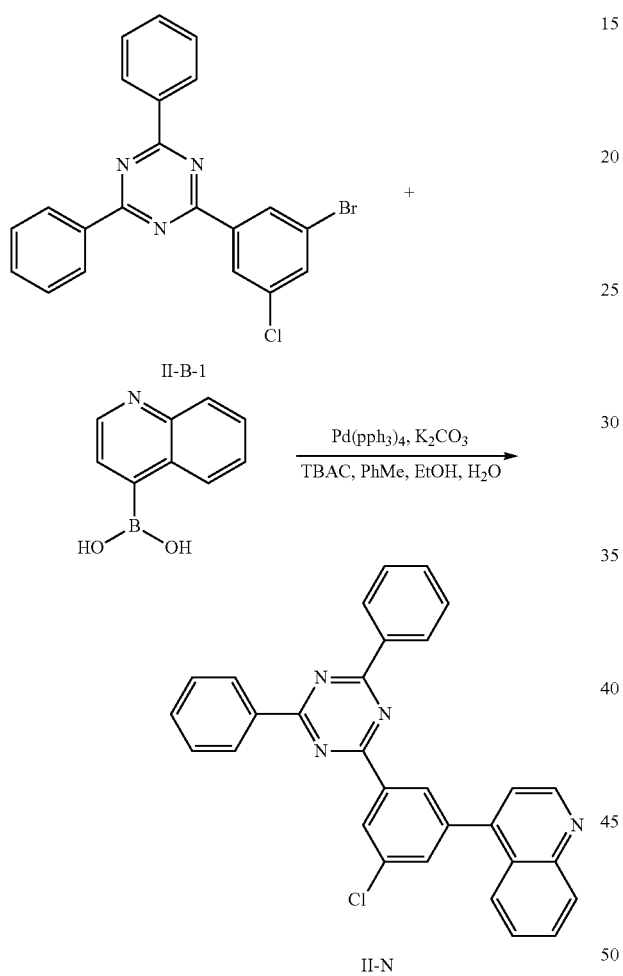

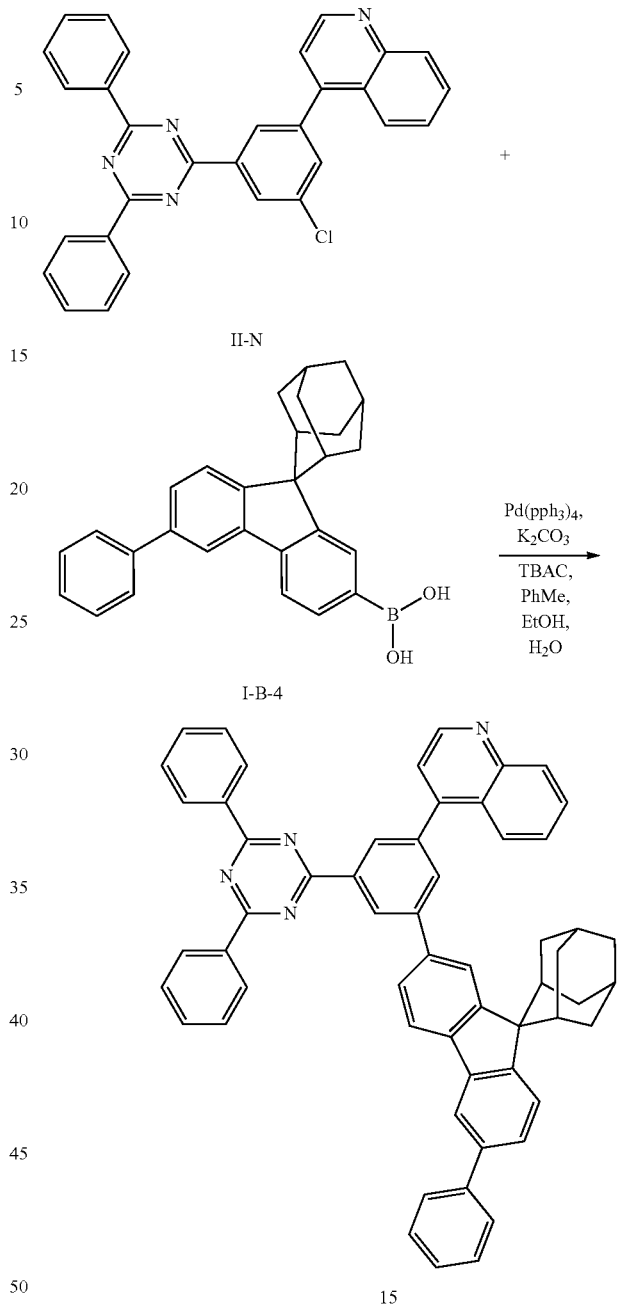

The intermediate II-B-1 (4.00 g, 9.46 mmol), quinoline-4-boronic acid (1.96 g, 11.35 mmol), tetra(triphenylphosphine)palladium (0.22 g, 1.89 mmol), potassium carbonate (2.62 g, 18.92 mmol), tetrabutylammonium chloride (0.13 g, 0.47 mmol), toluene (32 mL), ethanol (16 mL) and deionized water (8 mL) were added to a three-necked flask, and warmed to 76° C. under nitrogen protection, then heated for reflux and stirred for 5 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-N (3.24 g, 72.84%).

The intermediate II-N (3.20 g, 6.79 mmol), intermediate I-B-4 (3.31 g, 8.15 mmol), tetra(triphenylphosphine) palladium (0.15 g, 0.13 mmol), potassium carbonate (1.87 g, 13.58 mmol), tetrabutylammonium chloride (0.09 g, 0.34 mmol), toluene (28 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain a compound 15 (4.00 g, 74.75%). Mass spectrum: m/z=797.36 (M+H)$^+$.

Synthesis of Compound 16

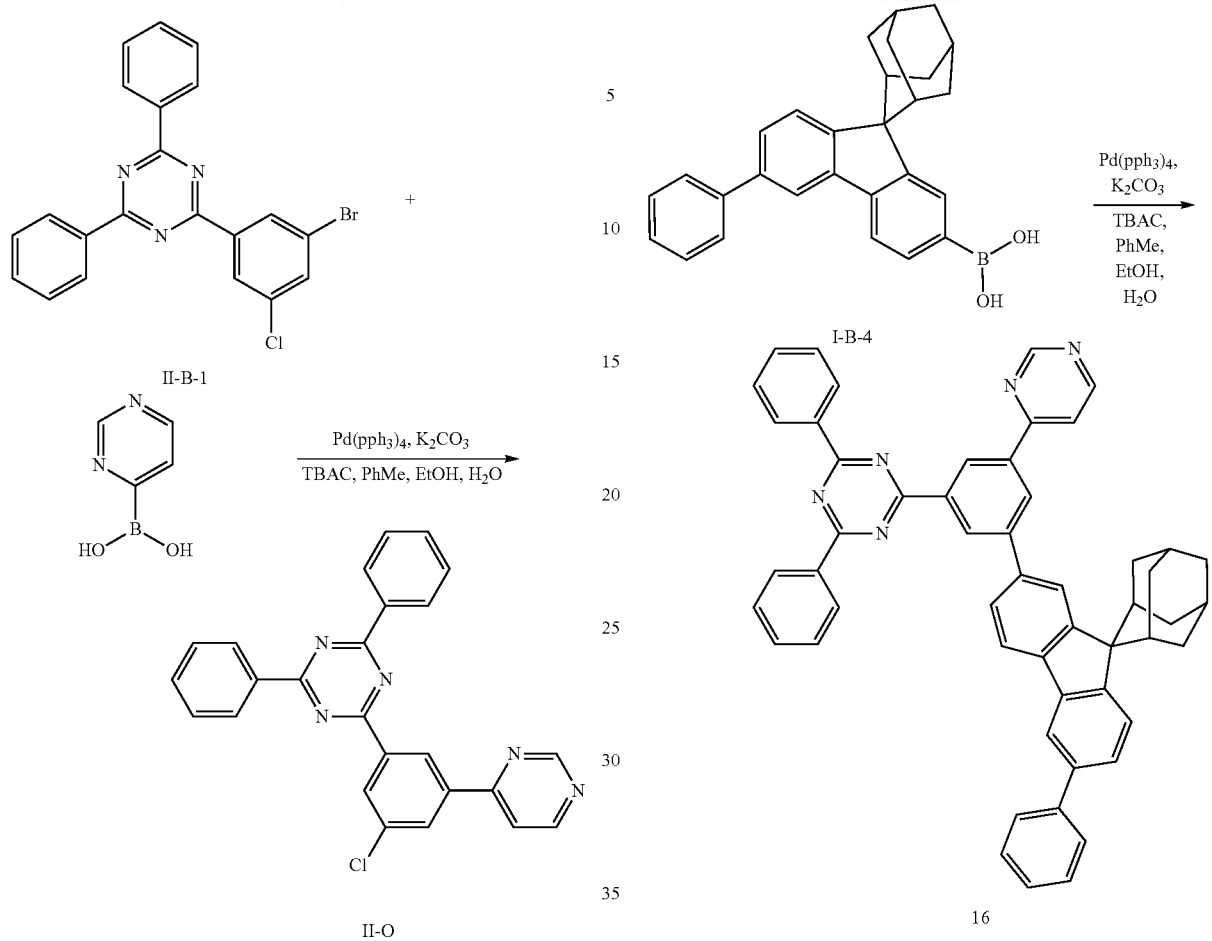

The intermediate II-B-1 (4.20 g, 9.93 mmol), pyrimidine-4-boronic acid (1.47 g, 11.92 mmol), tetra(triphenylphosphine)palladium (0.23 g, 1.19 mmol), potassium carbonate (2.74 g, 19.87 mmol), tetrabutylammonium chloride (0.14 g, 0.49 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-O (3.13 g, 74.85%).

The intermediate II-O (3.20 g, 7.34 mmol), the intermediate I-B-4 (3.58 g, 8.82 mmol), tetra(triphenylphosphine)palladium (0.17 g, 0.15 mmol), potassium carbonate (2.03 g, 14.69 mmol), tetrabutylammonium chloride (0.10 g, 0.36 mmol), toluene (28 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain a compound 16 (4.47 g, 81.46%). Mass spectrum: m/z=748.34 (M+H)⁺.

Synthesis of Compound 17

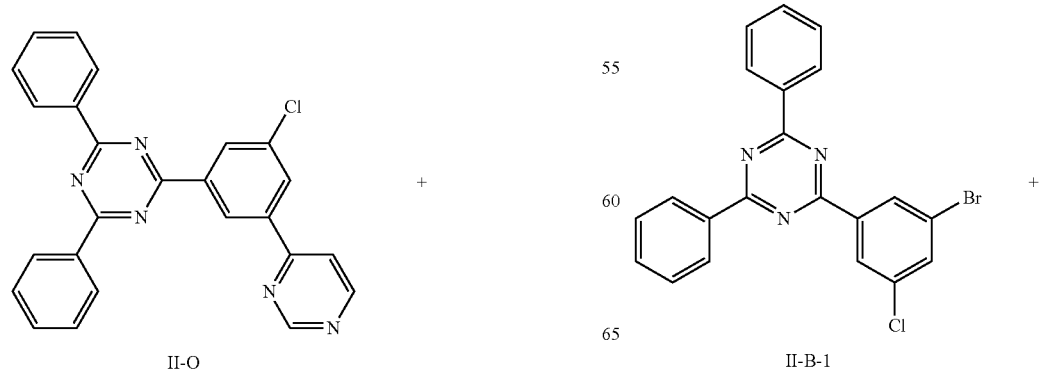

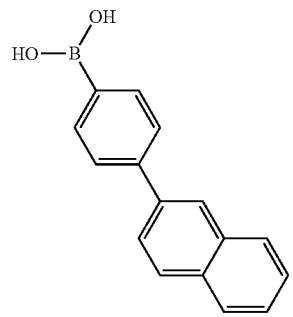

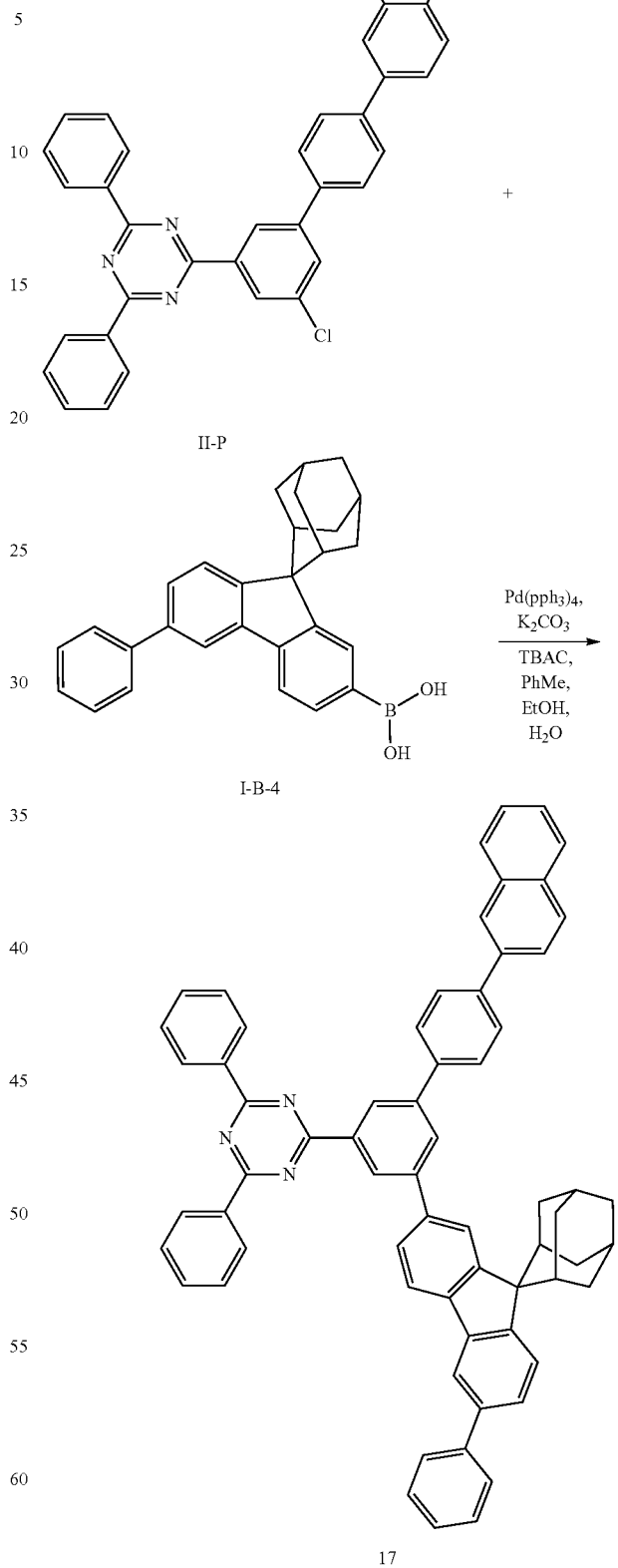

The intermediate II-B-1 (6.00 g, 14.19 mmol), 4-(naphthalene-2-)phenylboronic acid (3.87 g, 11.92 mmol), tetra(triphenylphosphine)palladium (0.32 g, 0.28 mmol), potassium carbonate (3.92 g, 28.38 mmol), tetrabutylammonium chloride (0.19 g, 0.71 mmol), toluene (48 mL), ethanol (24 mL) and deionized water (12 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-P (5.80 g, 74.85%).

The intermediate II-P (5.50 g, 10.07 mmol), intermediate I-B-4 (4.50 g, 11.07 mmol), tetra(triphenylphosphine) palladium (0.23 g, 0.20 mmol), potassium carbonate (2.78 g, 20.14 mmol), tetrabutylammonium chloride (0.14 g, 0.50 mmol), toluene (48 mL), ethanol (24 mL) and deionized water (12 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain a compound 17 (6.17 g, 70.32%). Mass spectrum: m/z=872.39 (M+H)+.

Synthesis of Compound 18

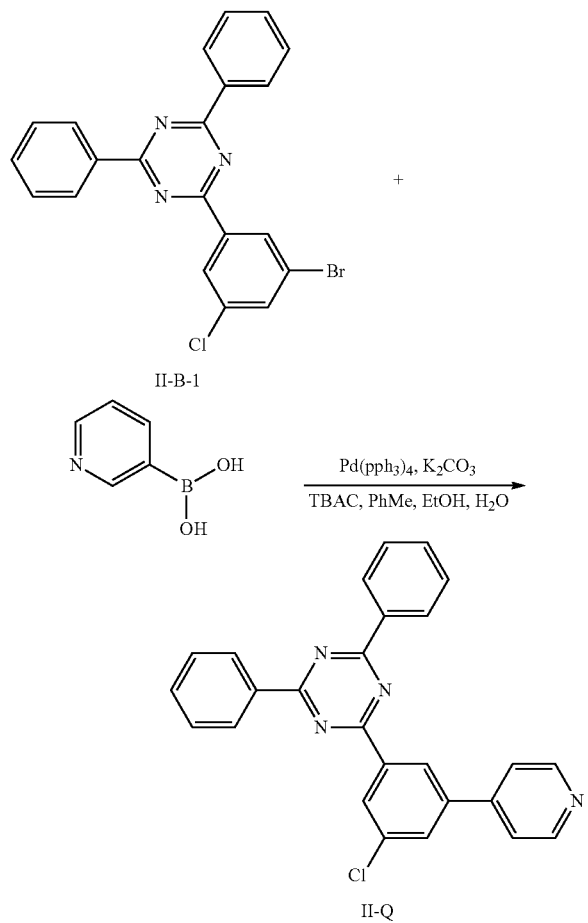

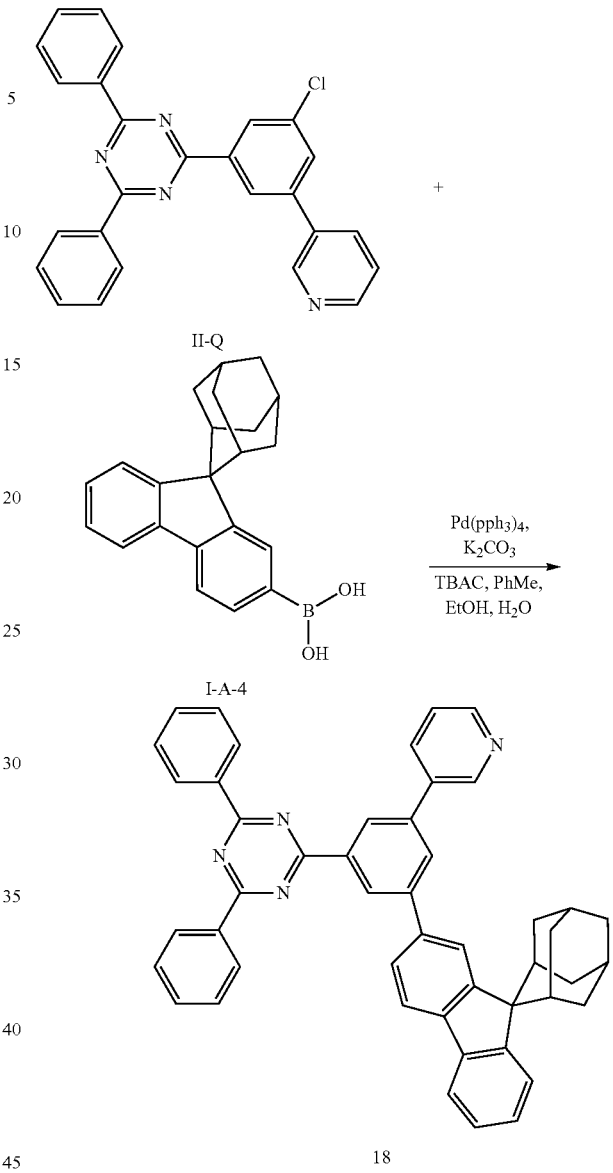

The intermediate II-B-1 (6.00 g, 14.19 mmol), 3-pyridine phenylboric acid (2.09 g, 17.03 mmol), tetra(triphenylphosphine) palladium (0.32 g, 0.28 mmol), potassium carbonate (3.92 g, 28.38 mmol), tetrabutylammonium chloride (0.19 g, 0.47 mmol), toluene (48 mL), ethanol (24 mL) and deionized water (12 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-Q (4.39 g, yield: 73.65%).

The intermediate II-Q (4.00 g, 9.50 mmol), the intermediate I-A-4 (4.24 g, 10.45 mmol), tetra(triphenylphosphine) palladium (0.21 g, 0.19 mmol), potassium carbonate (2.62 g, 19.00 mmol), tetrabutylammonium chloride (0.12 g, 0.44 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was recrystallized with methylbenzene to obtain a compound 18 (5.26 g, yield: 81.46%). Mass spectrum: m/z=671.31 (M+H)+. Hydrogen Nuclear Magnetic Resonance Spectrum (1H NMR) data: 1H NMR (CDCl3, 400 MHz): 9.18 (s, 1H), 9.11 (s, 1H), 8.96 (s, 1H), 8.82 (d, 4H), 8.71 (d, 1H), 8.59 (s, 1H), 8.17 (d, 1H), 8.12-8.09 (m, 3H), 7.95 (d, 1H), 7.87 (d, 1H), 7.80 (d, 1H), 7.64 (t, 2H), 7.60

(t, 3H), 7.51-7.49 (m, 1H), 7.43 (t, 1H), 7.34 (t, 1H), 3.17 (d, 2H), 3.00 (d, 2H), 2.36 (s, 1H), 2.27 (s, 1H), 2.07 (s, 2H), 1.94 (d, 2H), 1.87 (d, 2H), and 1.75 (s, 2H).

Synthesis of Compound 19

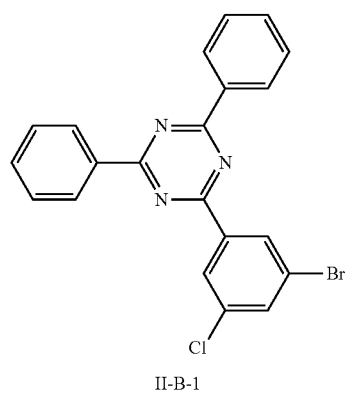

II-B-1

+

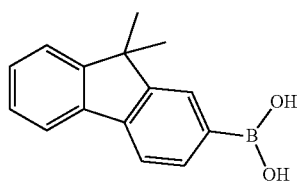

Pd(pph₃)₄, K₂CO₃
TBAC, PhMe, EtOH, H₂O
→

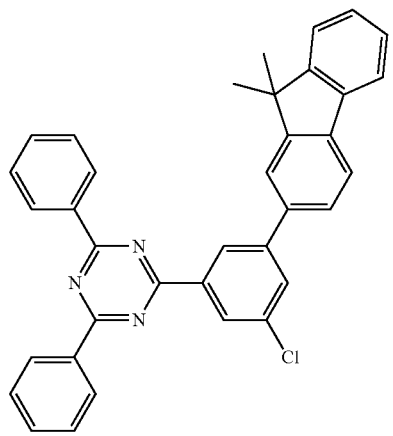

II-R

+

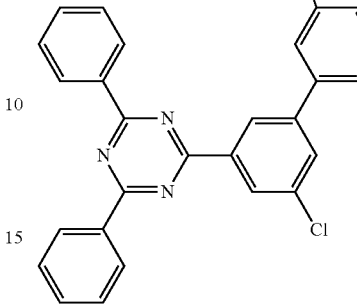

II-R

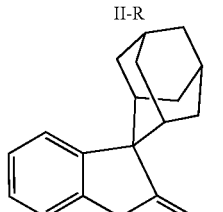

I-A-4

Pd(pph₃)₄, K₂CO₃
TBAC, PhMe, EtOH, H₂O
→

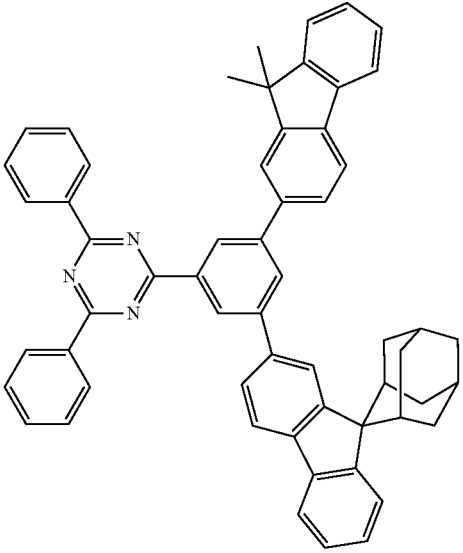

19

The intermediate II-B-1 (6.00 g, 14.19 mmol), 9,9-dimethylfluorene-2-boronic acid (4.05 g, 17.03 mmol), tetra(triphenylphosphine)palladium (0.32 g, 0.28 mmol), potassium carbonate (3.92 g, 28.38 mmol), tetrabutylammonium chloride (0.19 g, 0.47 mmol), toluene (48 mL), ethanol (24 mL) and deionized water (12 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a white solid, which was recrystallized with toluene to obtain an intermediate II-R (4.19 g, yield: 72.65%).

The intermediate II-R (4.8 g, 9.05 mmol), intermediate I-A-4 (3.44 g, 10.45 mmol), tetra(triphenylphosphine)palladium (0.21 g, 0.19 mmol), potassium carbonate (2.62 g, 19.00 mmol), tetrabutylammonium chloride (0.12 g, 0.44 mmol), toluene (32 mL), ethanol (16 mL) and deionized water (8 mL) were added to a three-necked flask, and warmed to 76° C. under nitrogen protection, then heated for reflux and stirred for 7 h. At the end of the reaction, the solution was cooled to room temperature; the reaction solution was washed with water and dried with the addition of magnesium sulfate, and then filtered, the filtrate was subjected to passing through a short silicagel column and treated under reduced pressure to remove the solvent; and the crude product was recrystallized with toluene to obtain a compound 19 (5.27 g, yield: 72.46%). Mass spectrum: m/z=786.38 (M+H)+.

Synthesis of Compound 77

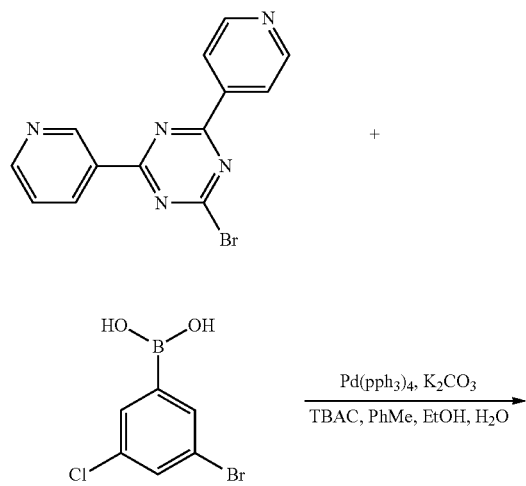

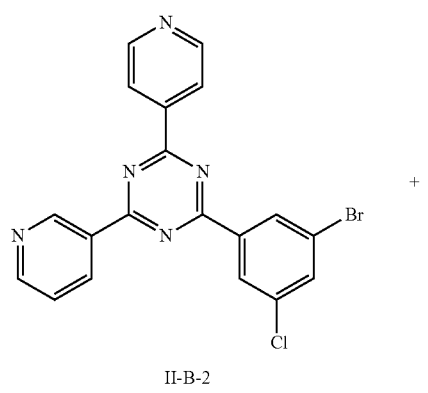

II-B-2

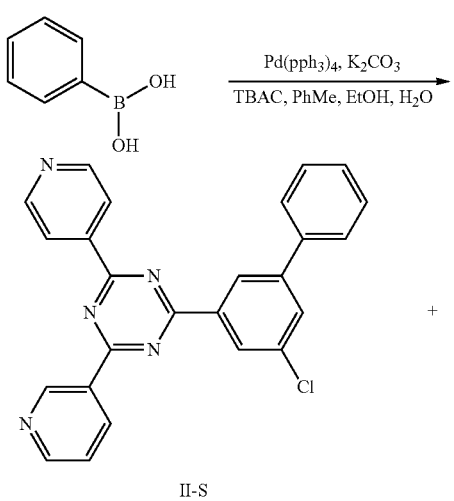

II-S

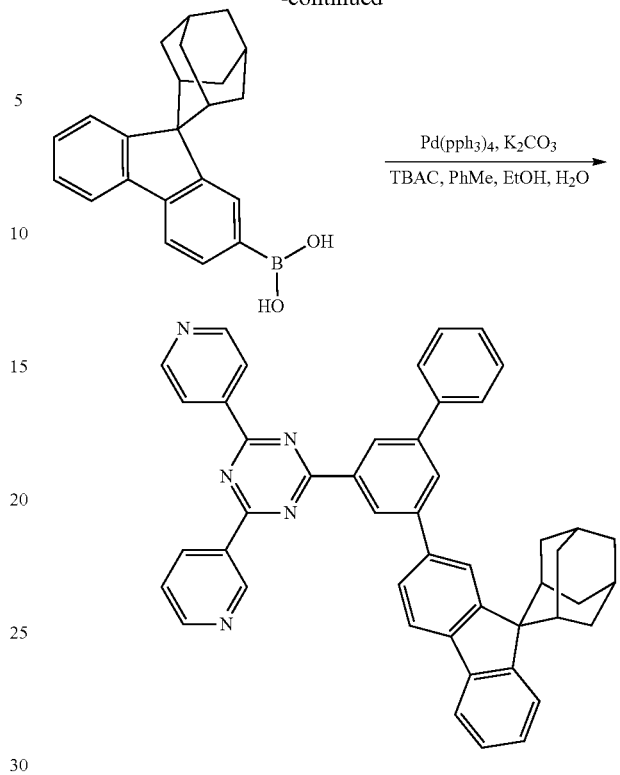

2-bromo-4-(pyridine-3-yl)-6-(pyridine-4-yl)-1,3,5-triazine (35.0 g, 111.4 mmol), 3-bromo-5-chlorophenylboronic acid (26.7 g, 113.6 mmol), tetra(triphenylphosphine)palladium (2.5 g, 2.2 mmol), potassium carbonate (30.7 g, 222.4 mmol), tetrabutylammonium chloride (0.6 g, 2.2 mmol), toluene (240 mL), ethanol (120 mL) and deionized water (60 mL) were added to a three-necked flask, and warmed to 76° C. under nitrogen protection, then heated for reflux and stirred for 8 h. At the end of the reaction, the solution was cooled to room temperature to separate out the reaction solid, then filtered by suction, the remainder was rinsed with water, then ethanol was added to remove the water to obtain a gray solid, the crude product was purified by silica gel column chromatography to obtain an intermediate II-B-2 (35.9 g, yield: 76%).

The intermediate II-B-2 (25.0 g, 58.8 mmol), phenylboronic acid (7.3 g, 60.0 mmol), tetra(triphenylphosphine) palladium (1.3 g, 1.1 mmol), potassium carbonate (16.2 g, 117.7 mmol), tetrabutylammonium chloride (0.3 g, 1.1 mmol), toluene (200 mL), ethanol (100 mL) and deionized water (50 mL) were added to a three-necked flask, and warmed to 76° C. under nitrogen protection, then heated for reflux and stirred for 15 h. At the end of the reaction, the solution was cooled to room temperature to separate out the reaction solid, then filtered by suction, the remainder was rinsed with water, then ethanol was added to remove the water to obtain a solid crude product, and the crude product was purified by silica gel column chromatography to obtain an intermediate II-S (16.8 g, yield: 68%).

The intermediate II-S (15.0 g, 35.5 mmol), intermediate I-A-4 (11.9 g, 36.2 mmol), tetra(triphenylphosphine) palladium (0.8 g, 0.7 mmol), potassium carbonate (9.8 g, 71.1 mmol), tetrabutylammonium chloride (0.2 g, 0.7 mmol), toluene (120 mL), ethanol (60 mL) and deionized water (30 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a gray solid crude product, and the crude product was purified by silica gel column chromatography to obtain a compound 77 (14.5 g, yield: 61%). Mass spectrum: m/z=672.30 (M+H)⁺.

Synthesis of Compound 78

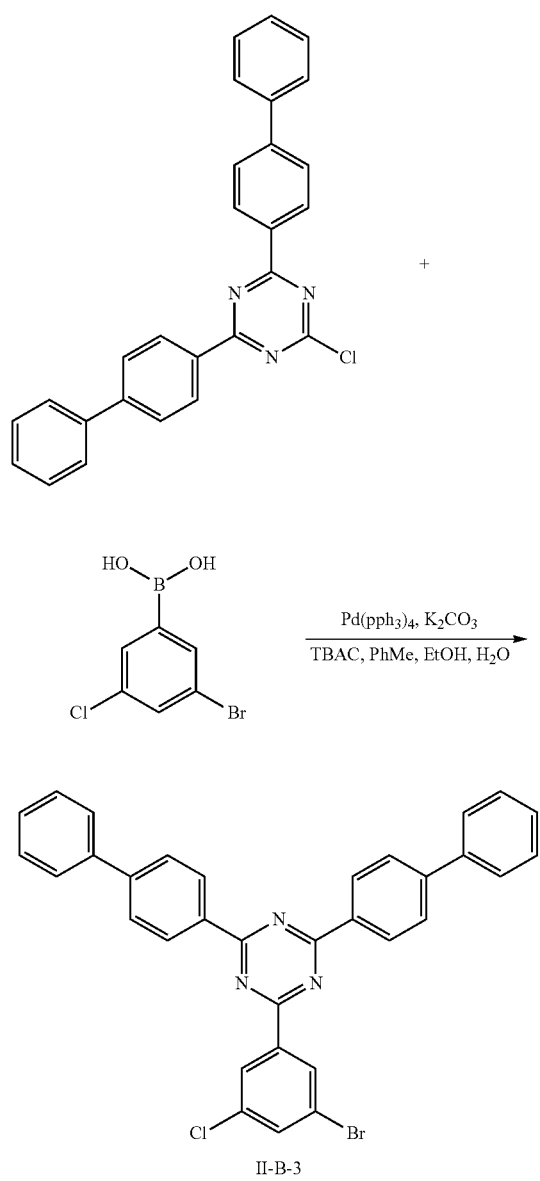

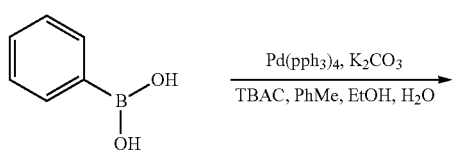

II-B-3

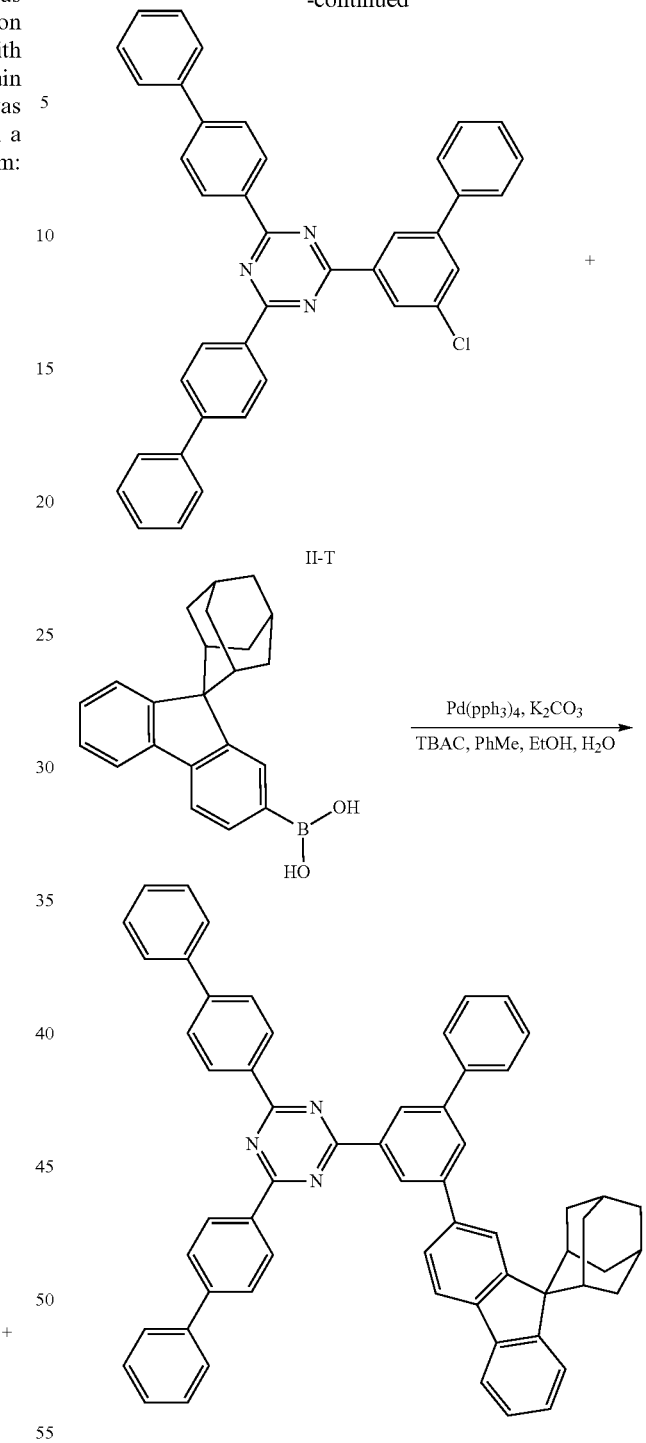

II-T 2,4-di([1,1'-biphenyl]4-yl)-6-chloro-1,3,5-triazine (30.0 g, 71.4 mmol), 3-bromo-5-chlorophenylboronic acid (17.1 g, 72.8 mmol), tetra(triphenylphosphine) palladium (1.6 g, 1.4 mmol), potassium carbonate (19.7 g, 142.8 mmol), tetrabutylammonium chloride (0.4 g, 1.4 mmol), toluene (240 mL), ethanol (120 mL) and deionized water (60 mL) were added to a three-necked flask, and warmed to 76° C. under nitrogen protection, then heated for reflux and stirred for 12 h. At the end of the reaction, the solution was cooled to room temperature to separate out the reaction solid, then filtered by suction, the remainder was rinsed with water, then ethanol was added to remove the water to obtain a gray solid, the crude product was purified by silica gel column chromatography to obtain an intermediate II-B-3 (29.5 g, yield: 72%).

The intermediate II-B-3 (25.0 g, 43.4 mmol), phenylboronic acid (10.4 g, 44.3 mmol), tetra(triphenylphosphine) palladium (1.0 g, 0.8 mmol), potassium carbonate (12.0 g, 86.9 mmol), tetrabutylammonium chloride (0.2 g, 0.8 mmol), toluene (200 mL), ethanol (100 mL) and deionized water (50 mL) were added to a three-necked flask, and warmed to 76° C. under nitrogen protection, then heated for reflux and stirred for 10 h. At the end of the reaction, the solution was cooled to room temperature to separate out the reaction solid, then filtered by suction, the remainder was rinsed with water, then ethanol was added to remove the water to obtain a solid crude product, and the crude product was purified by silica gel column chromatography to obtain an intermediate II-T (16.4 g, yield: 66%).

The intermediate II-T (15.0 g, 26.2 mmol), intermediate I-A-4 (8.8 g, 26.7 mmol), tetra(triphenylphosphine)palladium (0.6 g, 0.5 mmol), potassium carbonate (7.2 g, 52.4 mmol), tetrabutylammonium chloride (0.1 g, 0.5 mmol), toluene (120 mL), ethanol (60 mL) and deionized water (30 mL) were added to a three-necked flask, and warmed to 76° C. under nitrogen protection, then heated for reflux and stirred for 7 h. At the end of the reaction, the solution was cooled to room temperature to separate out the reaction solid, then filtered by suction, the remainder was rinsed with water, then ethanol was added to remove the water to obtain a gray solid crude product, and the crude product was purified by silica gel column chromatography to obtain a compound 78 (13.5 g, yield: 63%). Mass spectrum: m/z=822.38 (M+H)+

The organic electroluminescent device and manufacture method thereof of the present disclosure will be specified with reference to the accompanying drawings below.

Manufacture of a Blue Organic Electroluminescent Device

Example 1

Preparation of an anode 10 by the following process: a substrate having a thickness of 1500 Å was cut into a size of 40 mm×40 mm×0.7 mm, and prepared into a top-emitting experimental substrate with a cathode overlapping region, an anode and insulating layer pattern by a photoetching process; then a top-emitting experimental substrate was subjected to surface treatment by means of UV, ozone and $O_2$:$N_2$ plasma to enhance a work function of the anode (experimental substrate) and clean the experimental substrate.

HAT-CN was vacuum evaporated on the experimental substrate (anode 10) to form a hole injecting layer (HIL) 201 having a thickness of 100 Å.

NPB was vacuum evaporated on the hole injecting layer 201 to form a hole transporting layer (HTL) 202 having a thickness of 800 Å.

TCTA was evaporated on the hole transport layer 202 to form an electron blocking layer (EBL) 203 having a thickness of 300 Å.

α,β-ADN served as a host, and BD-1 was doped by a film thickness percentage of 3% and evaporated on the electron blocking layer 203 to form a light-emitting layer (EML) 204 having a thickness of 220 Å.

Compound 1 was evaporated on the light-emitting layer 204 to form an electron transporting layer (ETL) 206 having a thickness of 300 Å.

Yb was evaporated on the electron transport layer 206 to form an electron injecting layer (EIL) 207 having a thickness of 15 Å.

Mg and Ag were mixed according to an evaporation rate of 1:9, and vacuum evaporated on the electron injecting layer 207, thus forming a cathode 30 having a thickness of 120 Å.

In addition, CP-1 having a thickness of 650 Å was evaporated on the above cathode 30 to form a capping layer (CPL) 40, thus completing the manufacture of the organic luminescent device.

The structural formulas of HAT-CN, NPB, TCTA, α,β-ADN, BD-1 and CP-1 are as shown below:

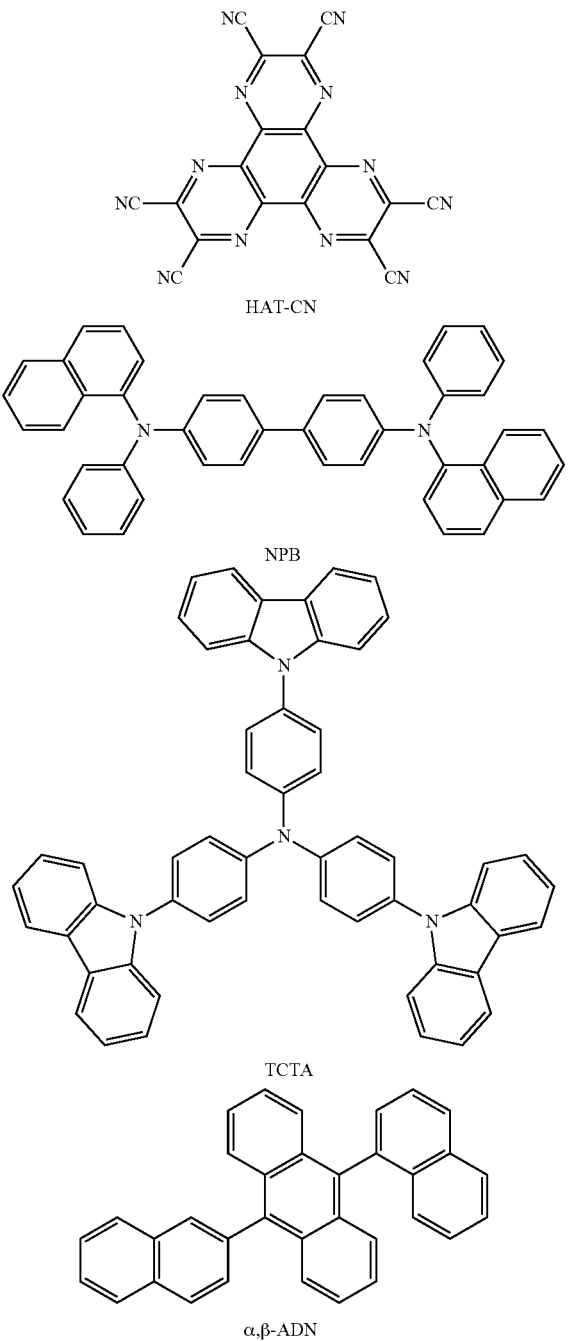

-continued

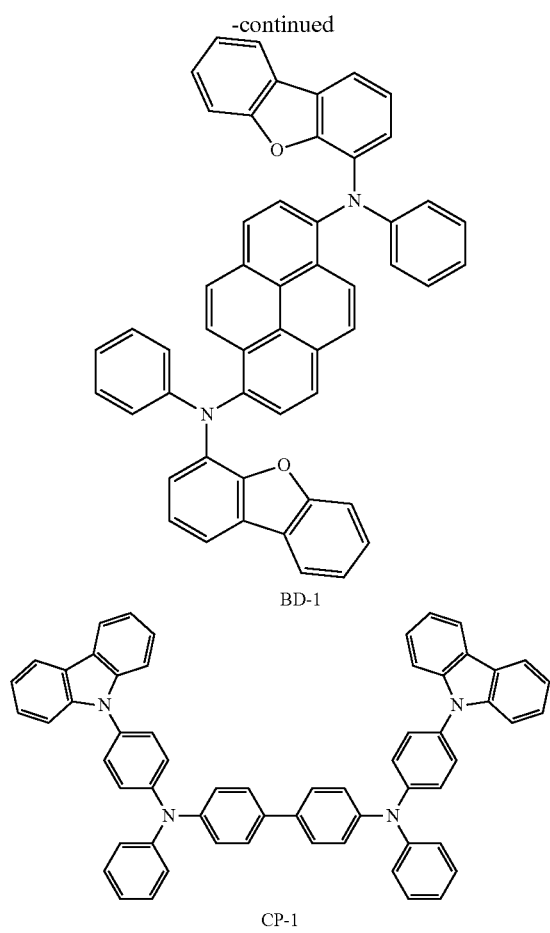

BD-1

CP-1

Examples 2 to 21

The organic electroluminescent devices were manufactured by the same method as in Example 1 except that Compound 1 is replaced with the compounds as shown in Table 1 in the formation of the electron transporting layer 206.

Comparative Examples 1 to 3

The organic electroluminescent devices in Comparative Examples 1 to 3 were manufactured by the same method as in Example 1 except that Compound 1 is replaced with $Alq_3$, TmPyPB and Bphen as an electron transporting layer material, respectively, in the formation of the electron transporting layer 206. The structural formulas of $Alq_3$, TmPyPB and Bphen are as shown below:

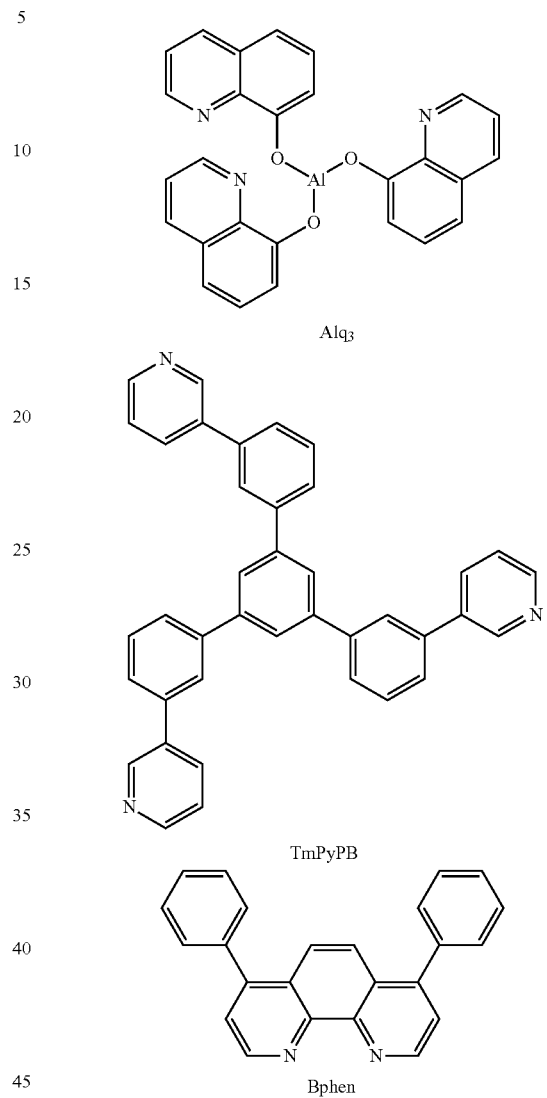

$Alq_3$

TmPyPB

Bphen

Performance test was performed on the organic electroluminescent devices prepared in Examples 1 to 21 and Comparative Example 1 to 3, where the comparison of IVL data shows a test result at 10 mA/cm² and lifetime shows a test result at a current density of 15 mA/cm², as shown in Table 1.

TABLE 1

| Example | Compound | Working voltage Volt(V) | Luminous efficiency Cd(A) | External quantum efficiency EQE(%) | T95 (h) Lifetime | Chromaticity coordinate CIEy |
|---|---|---|---|---|---|---|
| Example 1 | Compound 1 | 3.92 | 6.5 | 12.4 | 219 | 0.048 |
| Example 2 | Compound 2 | 3.94 | 6.5 | 12.4 | 212 | 0.048 |
| Example 3 | Compound 3 | 3.96 | 6.5 | 12.3 | 214 | 0.049 |
| Example 4 | Compound 4 | 3.90 | 6.4 | 12.5 | 212 | 0.049 |
| Example 5 | Compound 5 | 3.97 | 6.4 | 12.1 | 210 | 0.048 |
| Example 6 | Compound 6 | 3.90 | 6.4 | 12.4 | 218 | 0.048 |
| Example 7 | Compound 7 | 3.91 | 6.5 | 12.3 | 211 | 0.049 |
| Example 8 | Compound 8 | 3.91 | 6.5 | 12.7 | 215 | 0.049 |
| Example 9 | Compound 9 | 3.95 | 6.5 | 12.6 | 214 | 0.049 |

TABLE 1-continued

| Example | Compound | Working voltage Volt(V) | Luminous efficiency Cd(A) | External quantum efficiency EQE(%) | T95 (h) Lifetime | Chromaticity coordinate CIEy |
|---|---|---|---|---|---|---|
| Example 10 | Compound 10 | 3.97 | 6.4 | 12.4 | 211 | 0.049 |
| Example 11 | Compound 11 | 3.93 | 6.4 | 12.5 | 216 | 0.049 |
| Example 12 | Compound 12 | 3.98 | 6.4 | 12.3 | 215 | 0.049 |
| Example 13 | Compound 13 | 3.96 | 6.4 | 12.2 | 211 | 0.049 |
| Example 14 | Compound 14 | 3.92 | 6.4 | 12.7 | 212 | 0.049 |
| Example 15 | Compound 15 | 3.95 | 6.4 | 12.4 | 212 | 0.049 |
| Example 16 | Compound 16 | 3.94 | 6.4 | 12.3 | 211 | 0.048 |
| Example 17 | Compound 17 | 3.92 | 6.5 | 12.6 | 215 | 0.049 |
| Example 18 | Compound 18 | 3.96 | 6.4 | 12.7 | 215 | 0.049 |
| Example 19 | Compound 19 | 3.98 | 6.4 | 12.6 | 218 | 0.048 |
| Example 20 | Compound 77 | 3.94 | 6.4 | 12.2 | 211 | 0.048 |
| Example 21 | Compound 78 | 3.98 | 6.4 | 12.7 | 218 | 0.049 |
| Comparative Example 1 | Alq$_3$ | 4.4 | 5.5 | 10.7 | 185 | 0.049 |
| Comparative Example 2 | TmPyPB | 4.7 | 5.0 | 10.5 | 160 | 0.049 |
| Comparative Example 3 | Bphen | 4.3 | 5.6 | 10.2 | 163 | 0.049 |

According to the result of Table 1, examples 1 to 21 are compared with Comparative Examples 1 to 3 using Alq$_3$, TmPyPB and BphenZ which are ETL materials well known in the art, and the result shows that the above organic electroluminescent devices prepared with the compounds of the present disclosure as an electron transporting layer have reduced working voltage by at least 0.41 V, and enhanced luminous efficiency (Cd/A) by at least 16.1% and prolonged lifetime by at least 13.5%. The reason is that at an electric field intensity of 400 (V/cm)$^{1/2}$, the compounds used in the examples have an electronic mobility up to $4 \times 10^{-3}$ cm$^2$/V·s above. Therefore, the prepared organic electroluminescent devices have higher current efficiency. Because such kind of compounds have a LUMO energy level matched to adjacent layers better as well, the driving voltage of the prepared organic electroluminescent devices drop to some extent compared with those of Comparative Examples. Finally, adamantane introduced in such kind of compound promotes the molecular weight of materials and reduces molecular symmetry, increases the glass-transition temperature and evaporation temperature of the material, controls the material crystallinity. Therefore, the material has better physical and thermodynamic stability in mass production, and has improved durability and heat resistance, thereby greatly promoting the lifetime of the device. To sum up, the compound of the present disclosure is used in an electron transporting layer; and the organic electroluminescent device prepared in such a way can achieve low driving voltage, high luminous efficiency and long lifetime.

The above examples are merely used to provide a preparation method of a blue light-emitting device. A person skilled in the art should understand that the organic compound of the present disclosure may be further used in the preparation of other colors of light-emitting devices, which will be not repeatedly described any more. Similarly, the above examples are merely used to provide a specific preparation method of a blue light-emitting device. A person skilled in the art should understand that in the light-emitting device, other layers may use other materials with similar functions; and the electron transporting layer may be further doped with other materials according to other doping ratios. Moreover, the electron transporting layer may be further prepared into other thickness. These changes will not affect the performance of the compound of the present disclosure on the device.

A person skilled in the art will easily envisage other embodiments of the present disclosure after considering the description and practicing the present disclosure disclosed herein. The present disclosure aims at covering any transformations, uses or adaptive changes of the present disclosure. These transformations, uses or adaptive changes shall follow the general principle of the present disclosure and include common general knowledge or conventional technical means not disclosed herein. The description and examples are merely regarded as exemplary; the real scope and spirit of the present disclosure are indicated by the appendix claims.

The invention claimed is:

1. An organic compound, having a structure of:

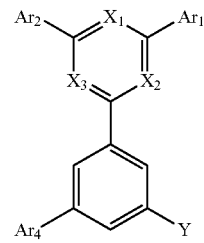

wherein $X_1$, $X_2$ and $X_3$ are the same, and all are N;

Y is
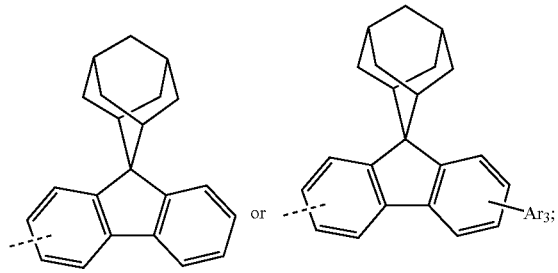
and
Ar₁, Ar₂ are each independently selected from the following groups:
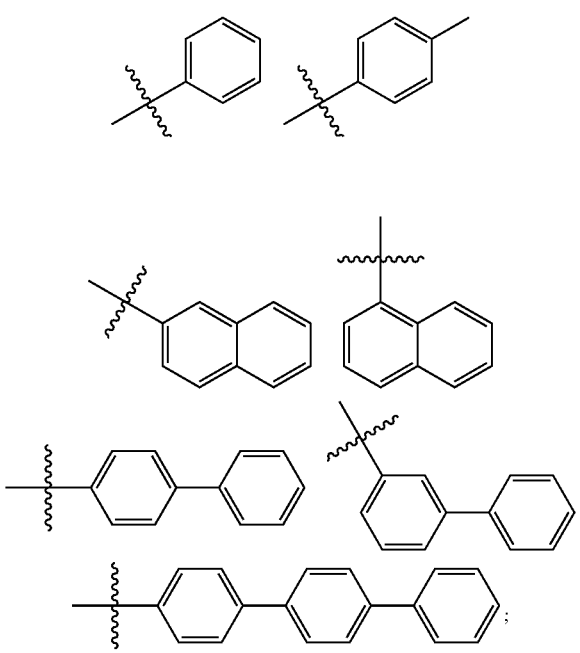
Ar₃ is the following group:
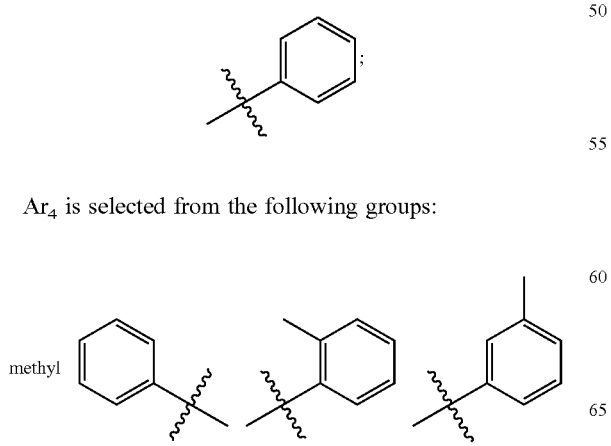
Ar₄ is selected from the following groups:
methyl
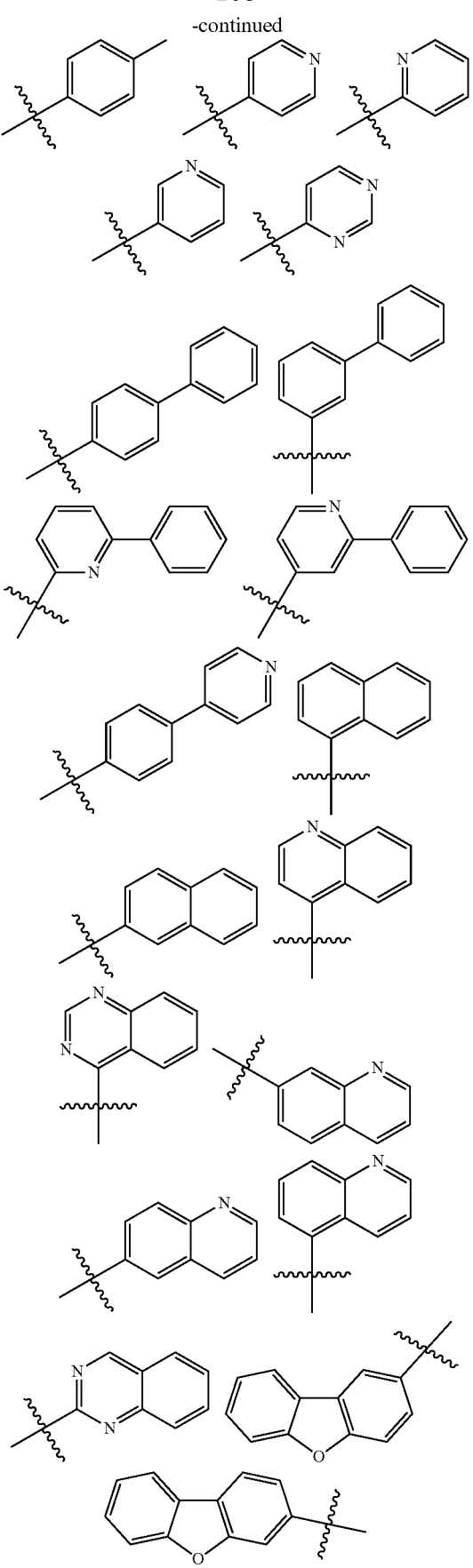

-continued
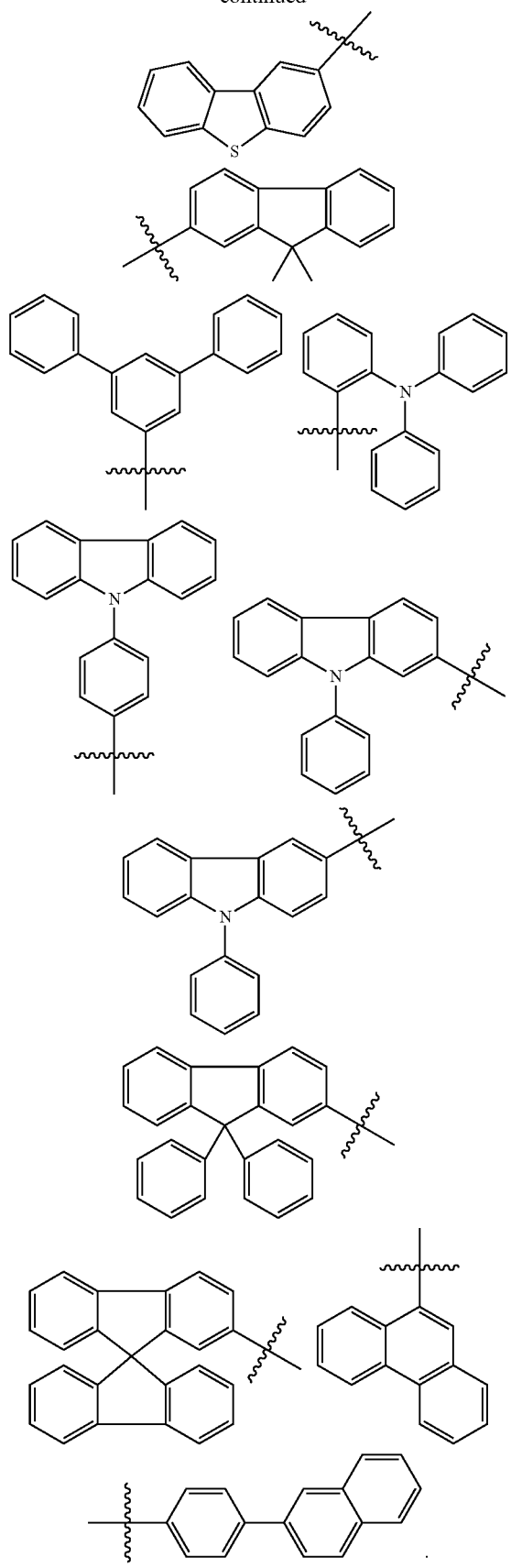
2. An organic compound, wherein the organic compound is selected from the following compounds:
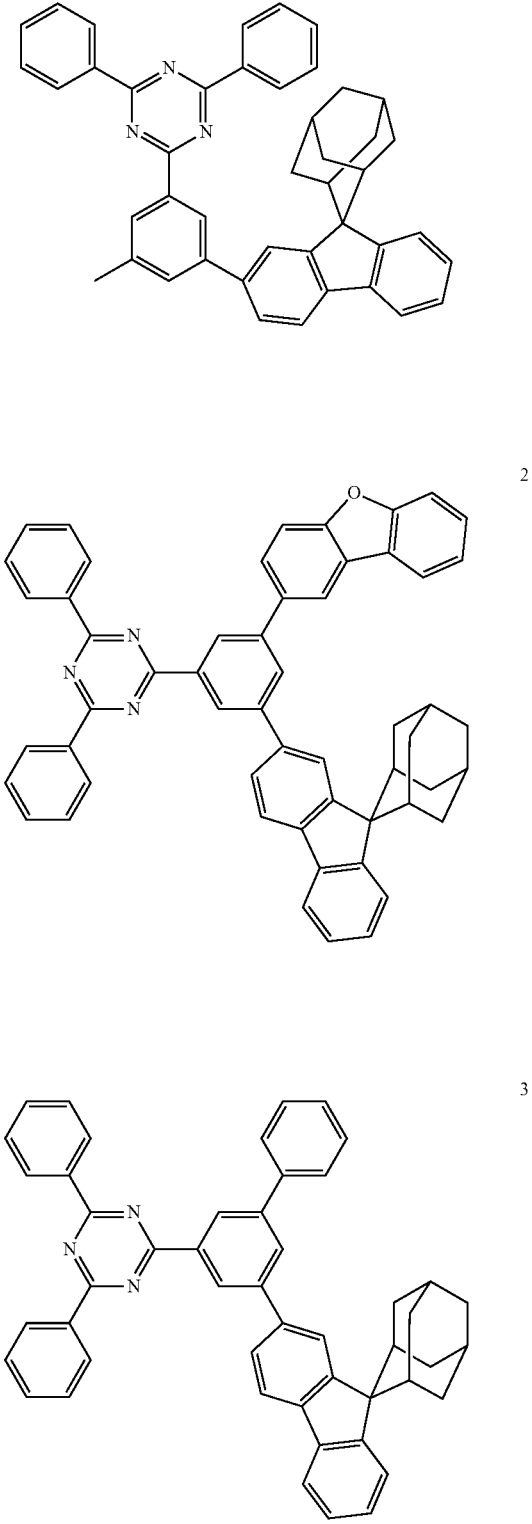

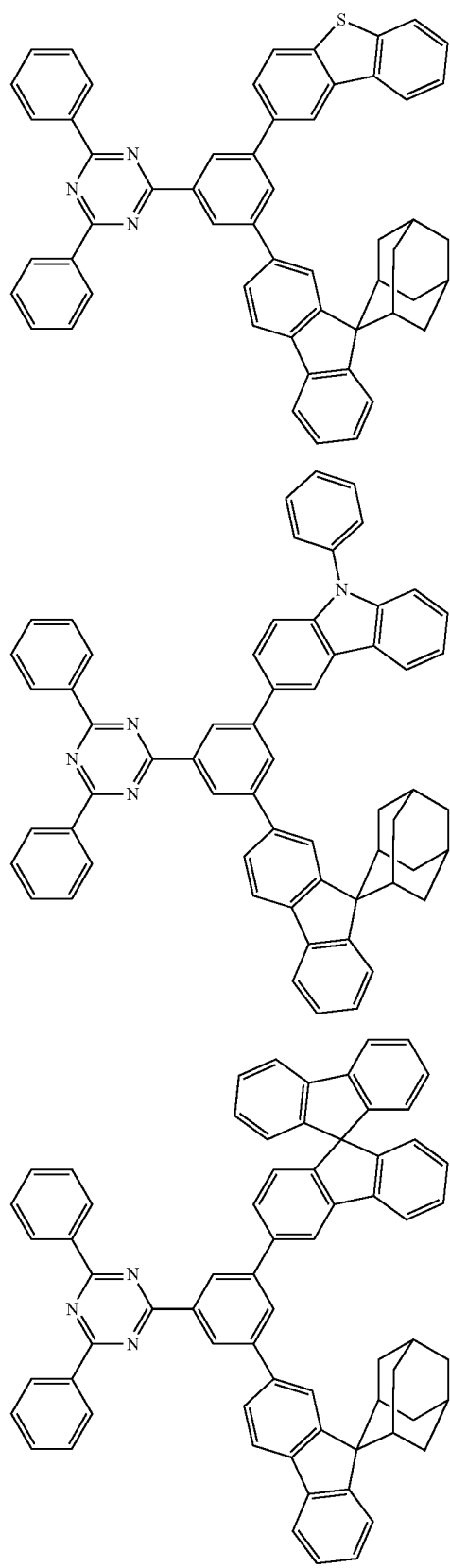
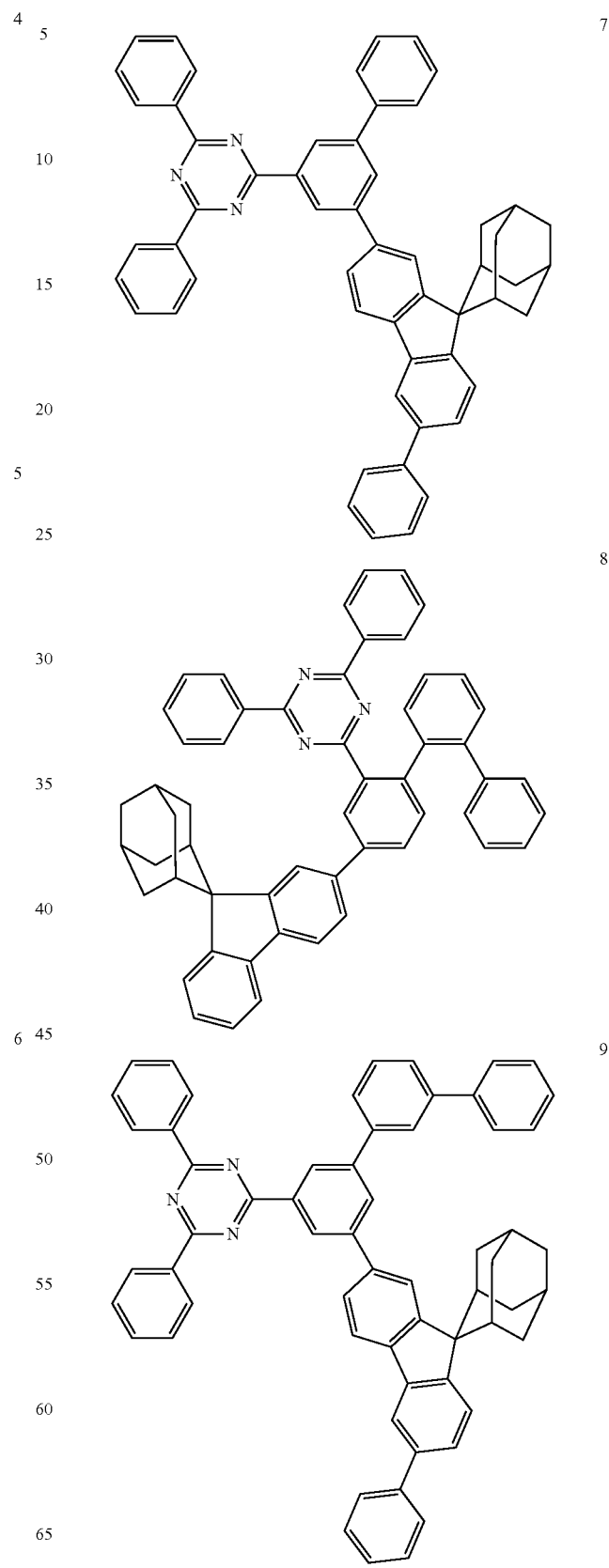

113
-continued
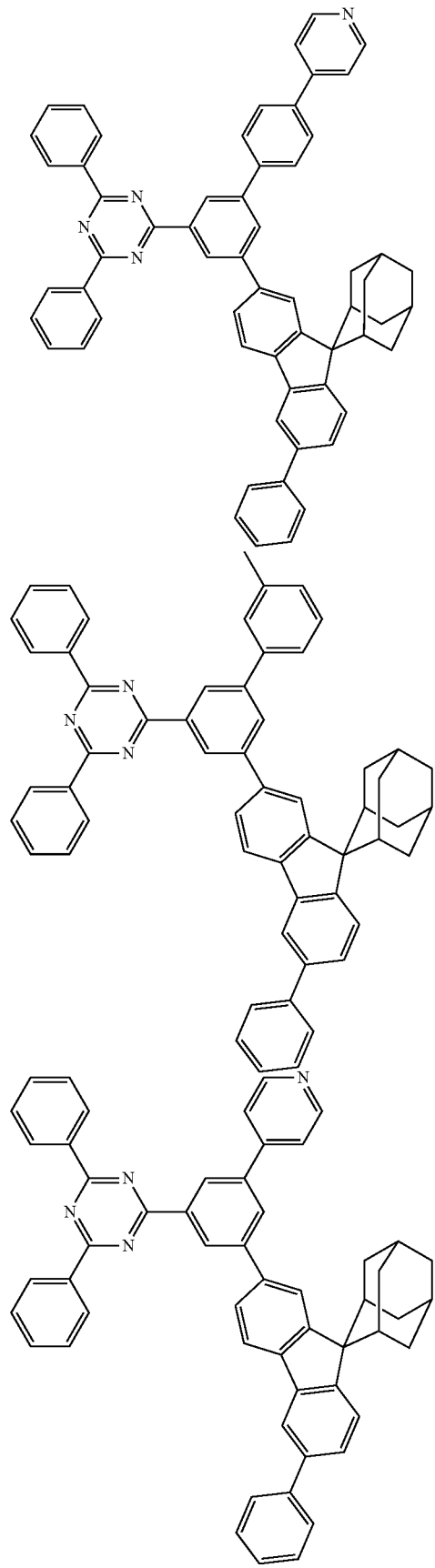
114
-continued
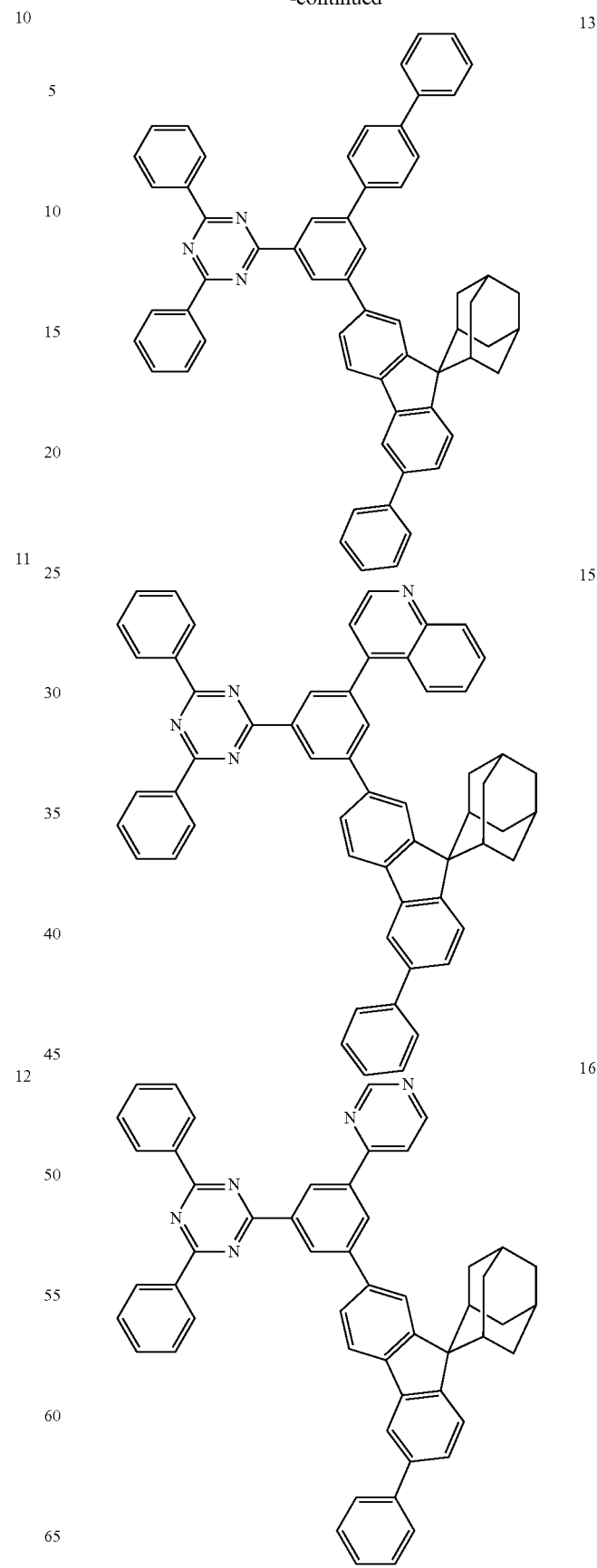

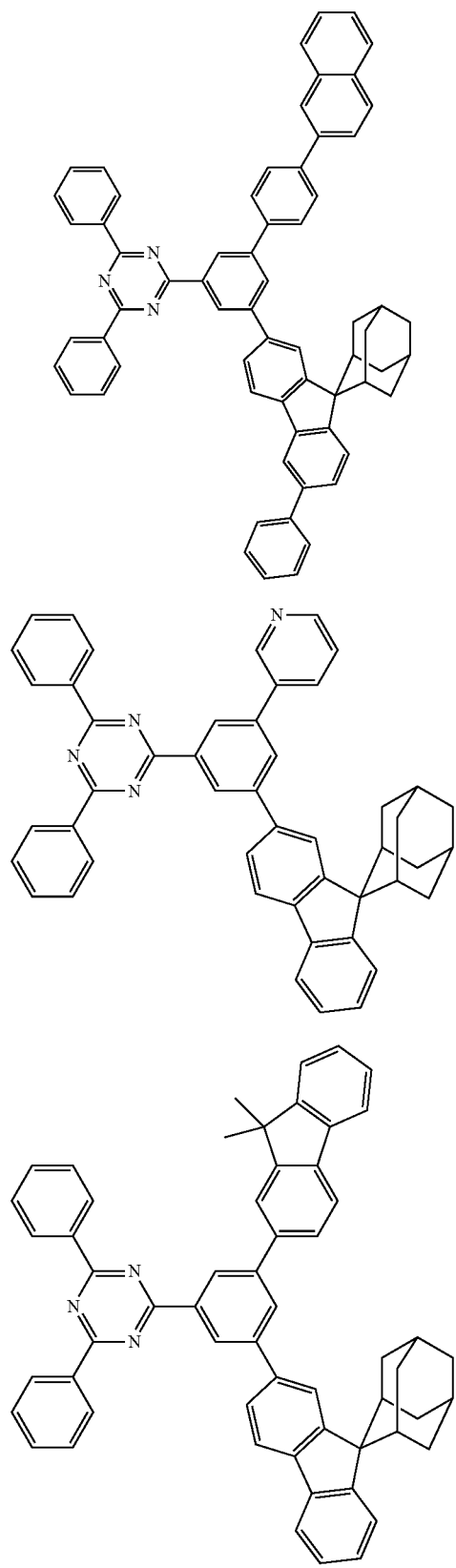
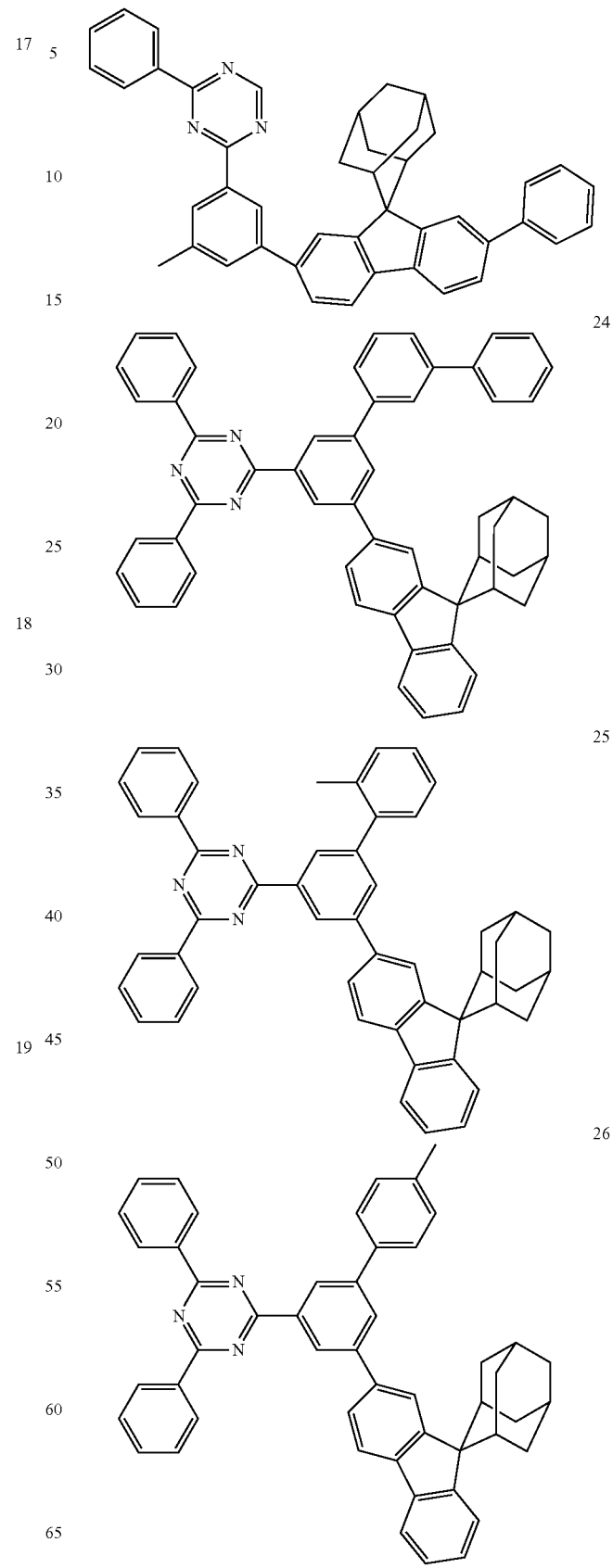

27
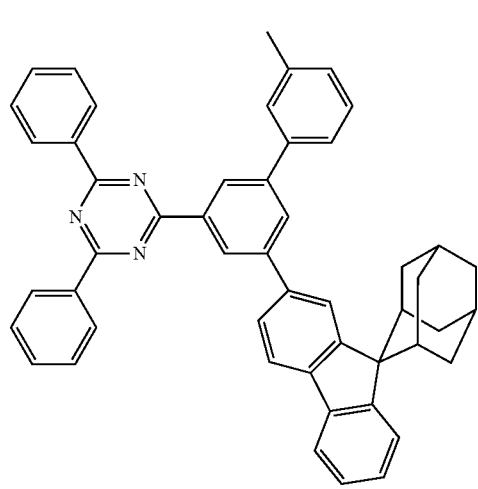
28
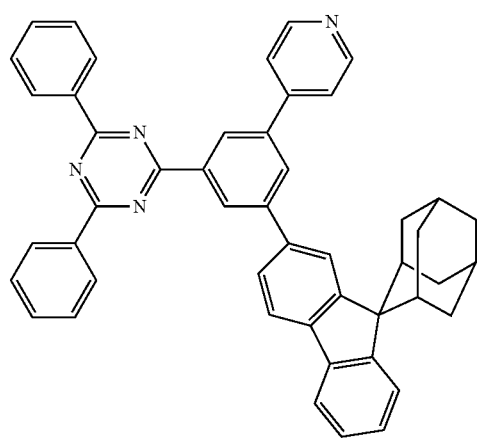
29
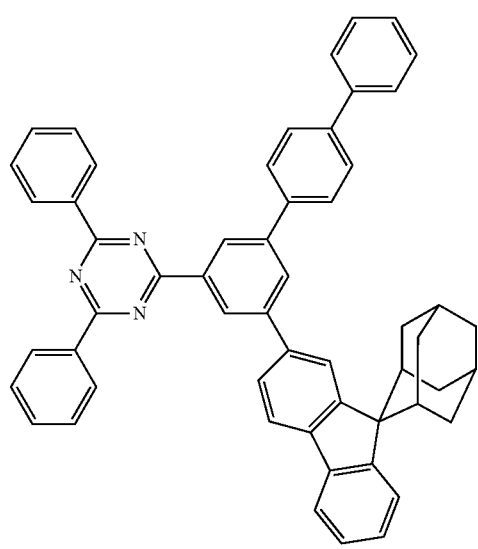
30
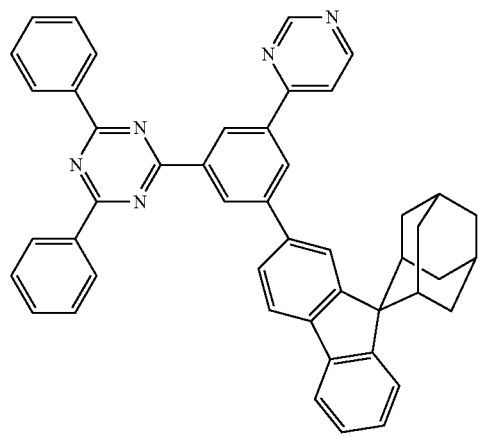
31
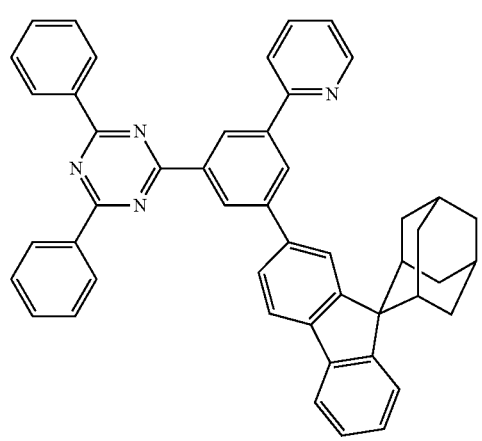
32
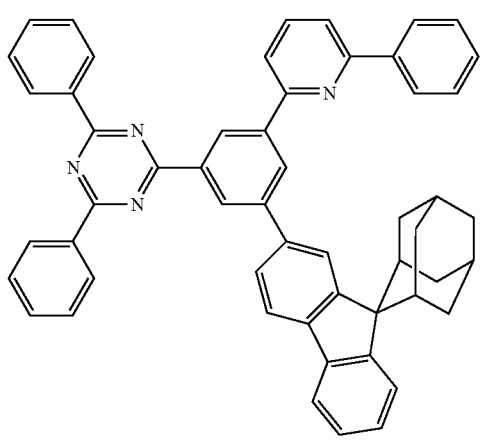

33
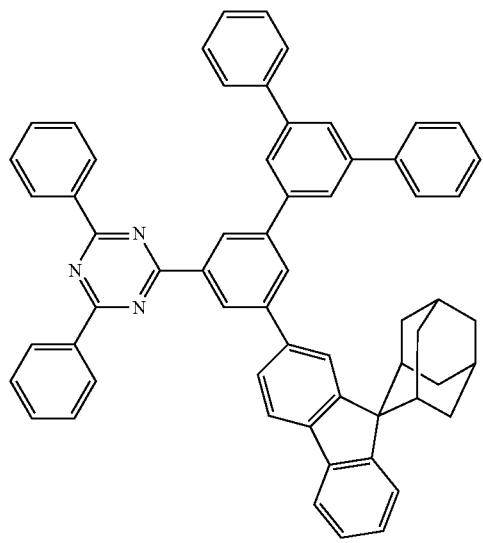
34
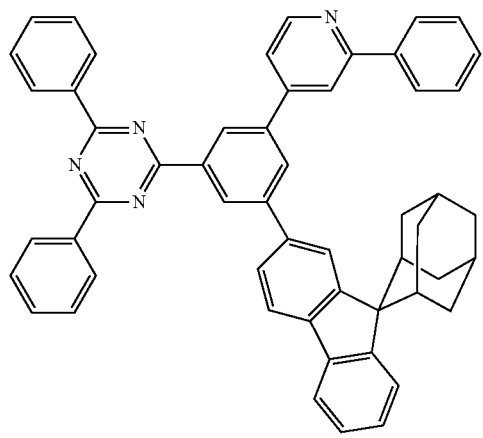
35
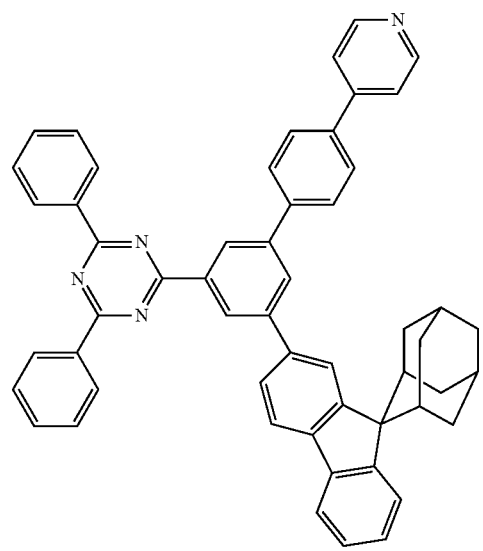
36
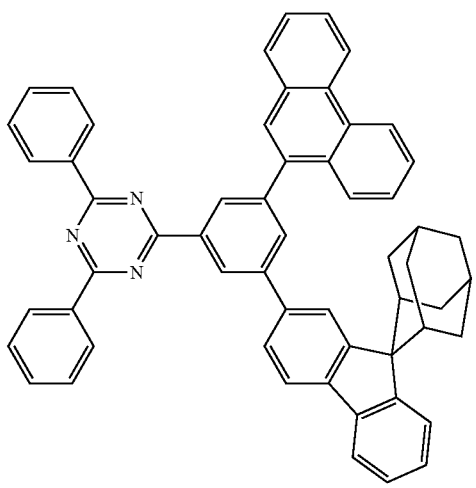
37
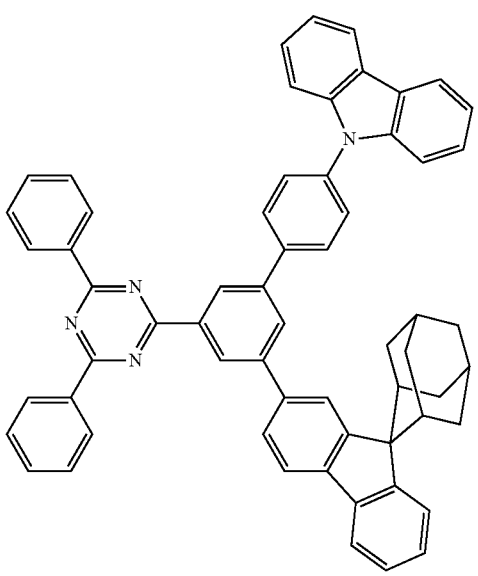
38
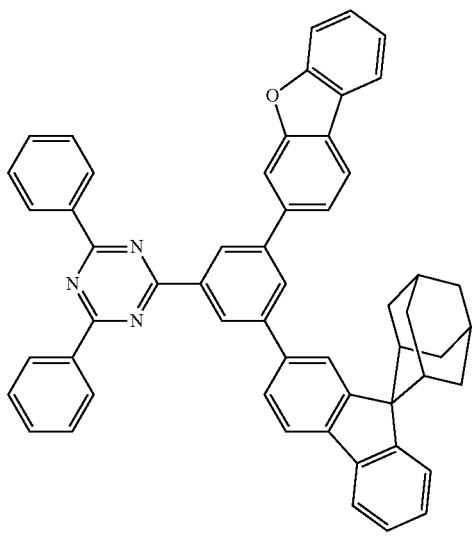

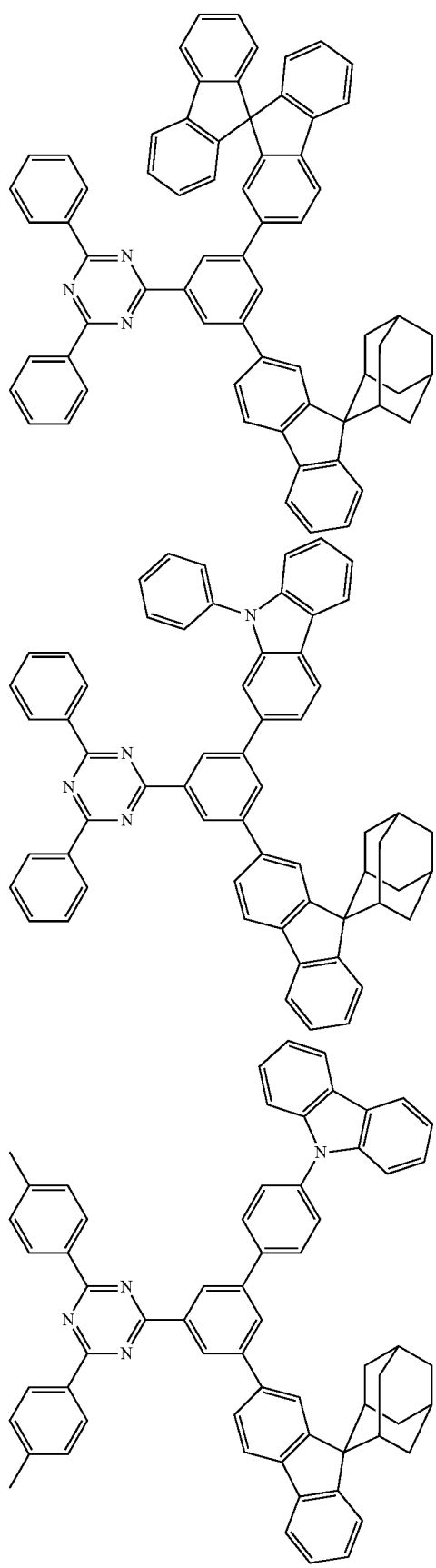
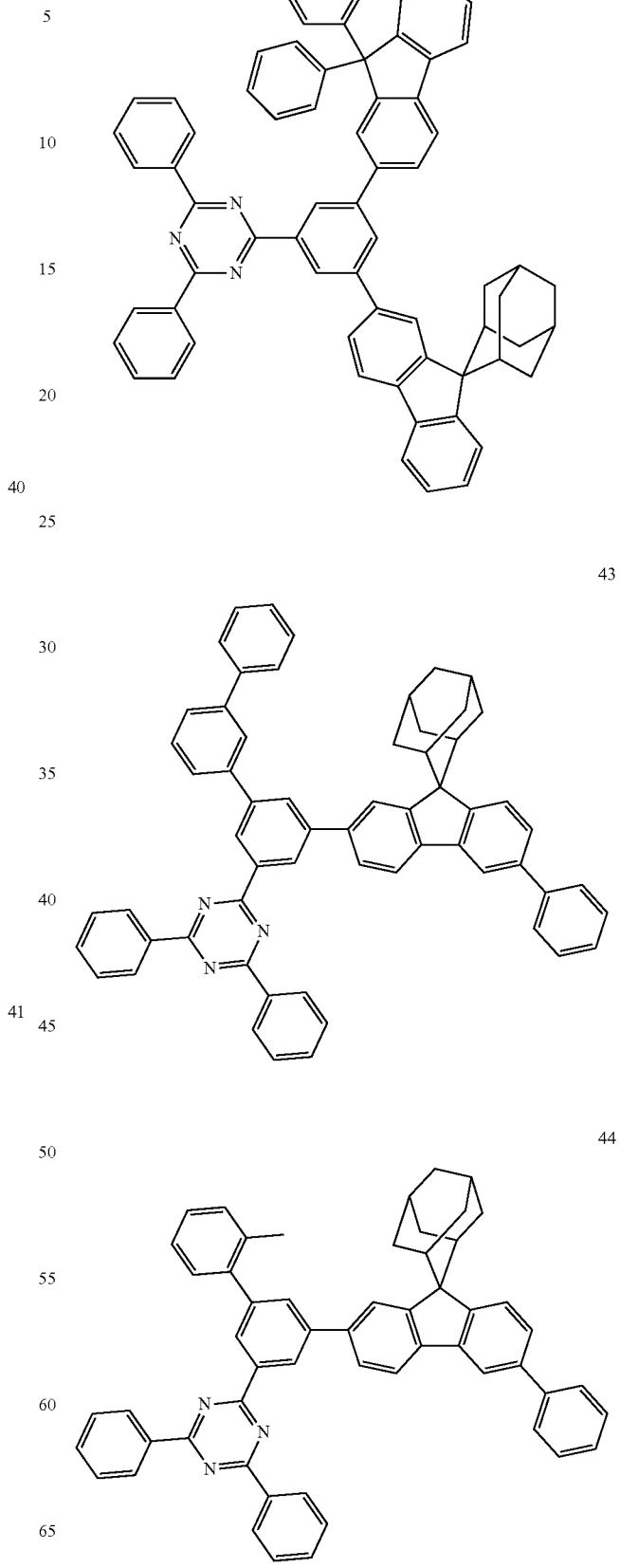

123
-continued
45
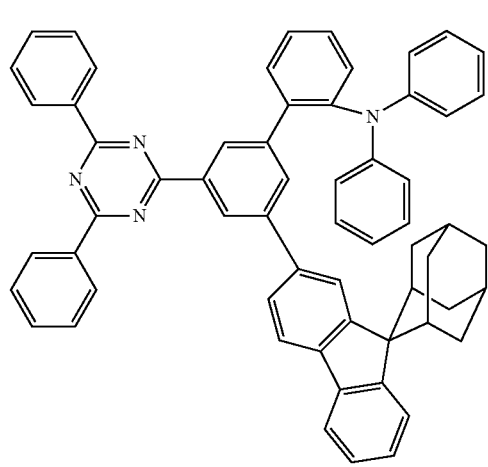
46
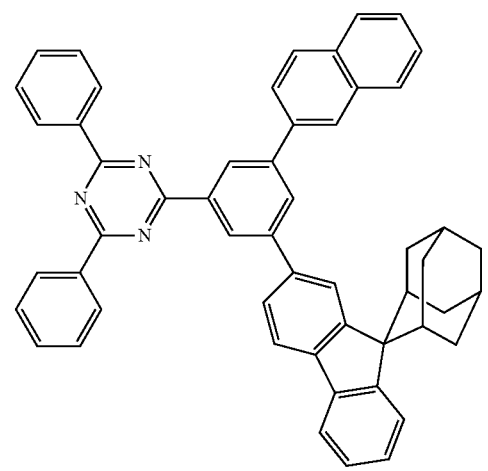
47
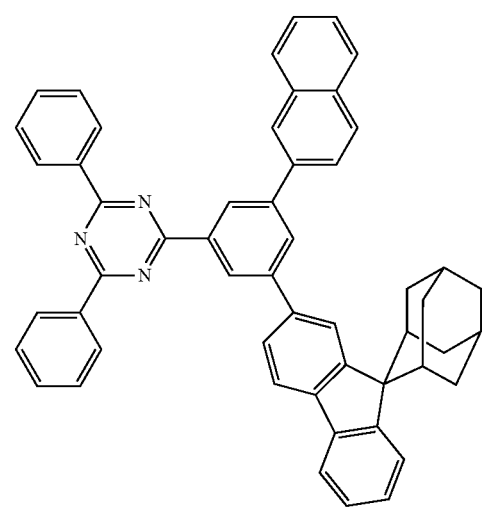
124
-continued
48
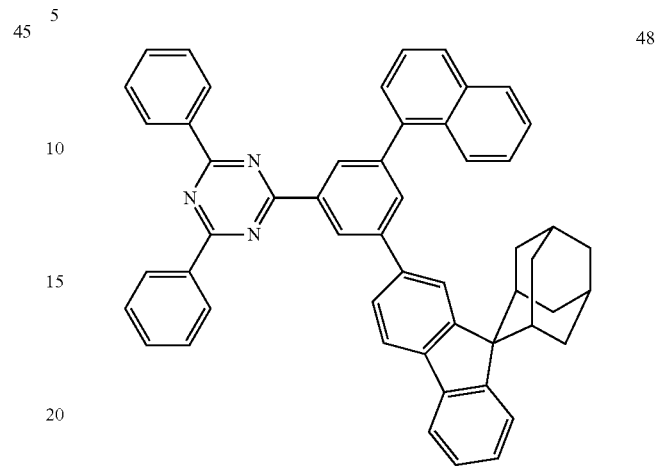
49
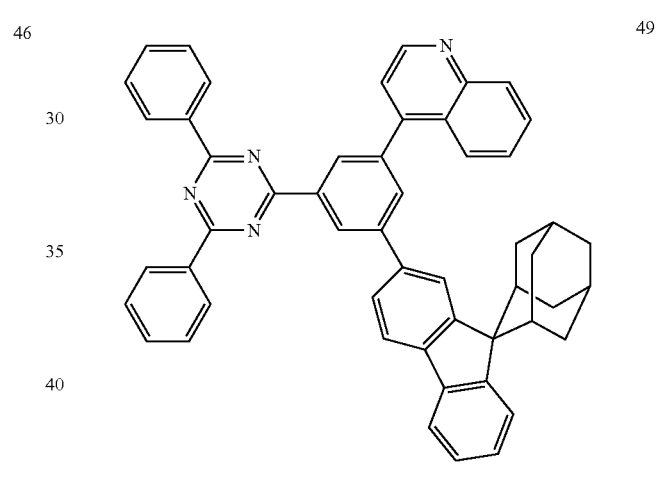
50
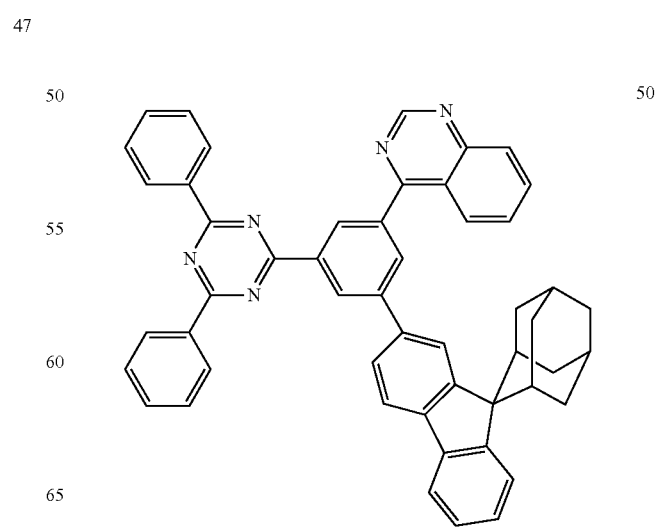

-continued
51
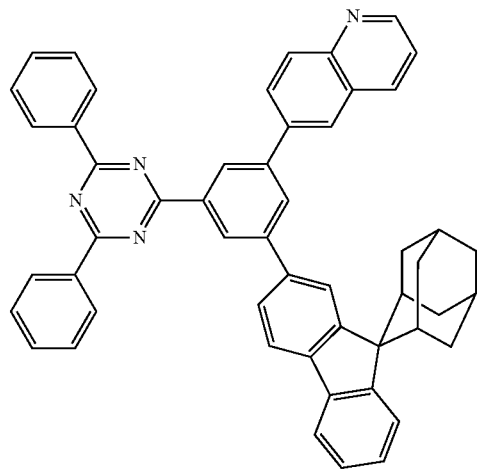
52
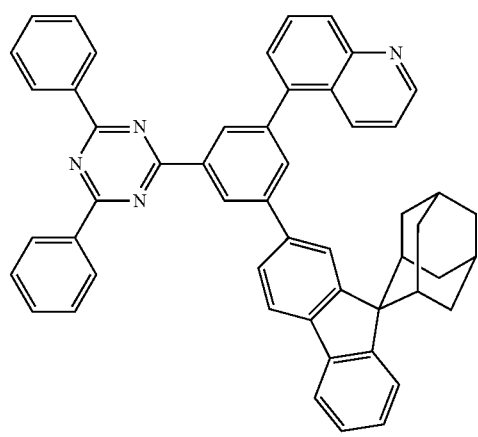
53
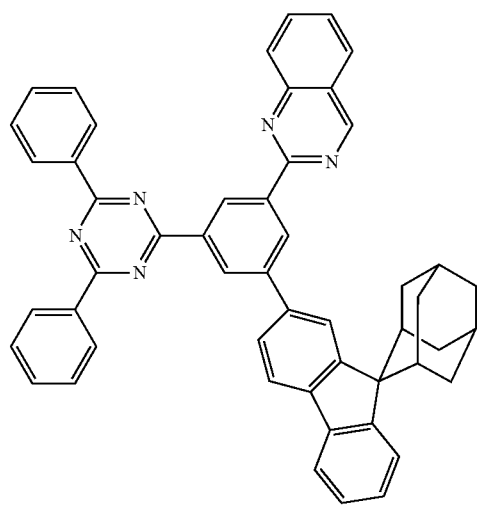
-continued
54
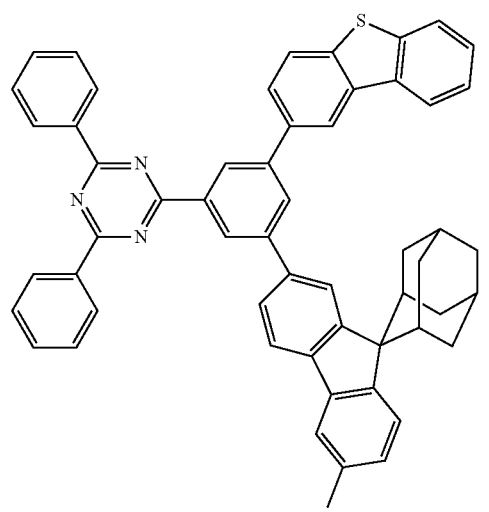
55
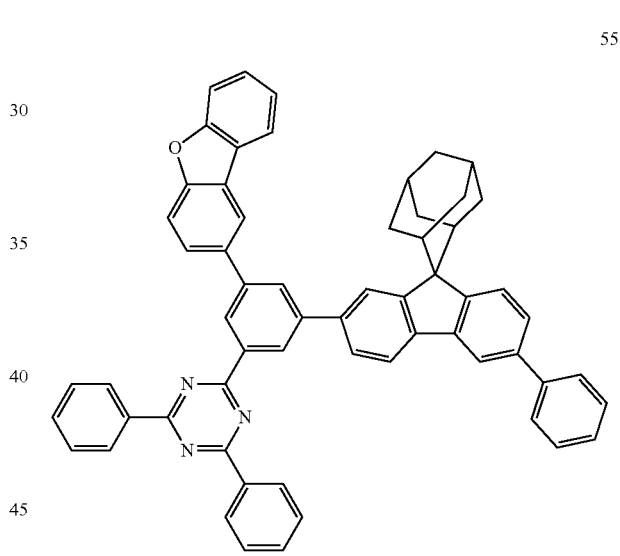
56
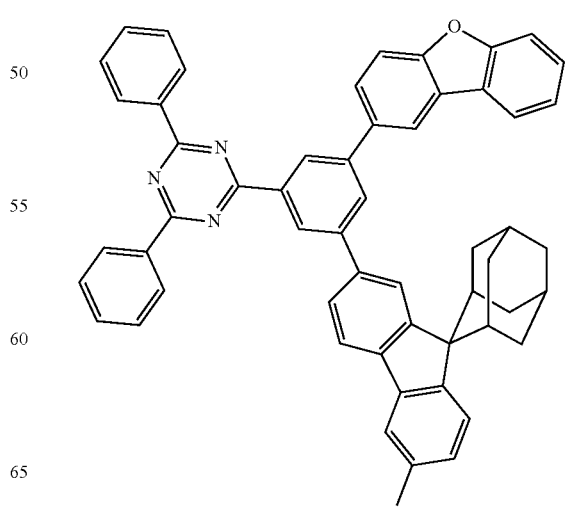

127
-continued
57
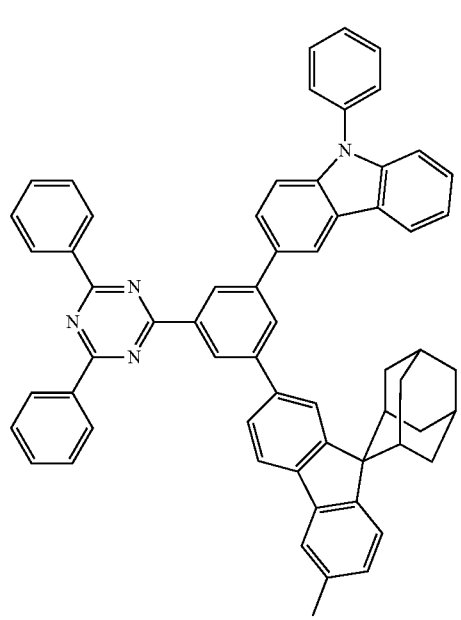
128
-continued
59
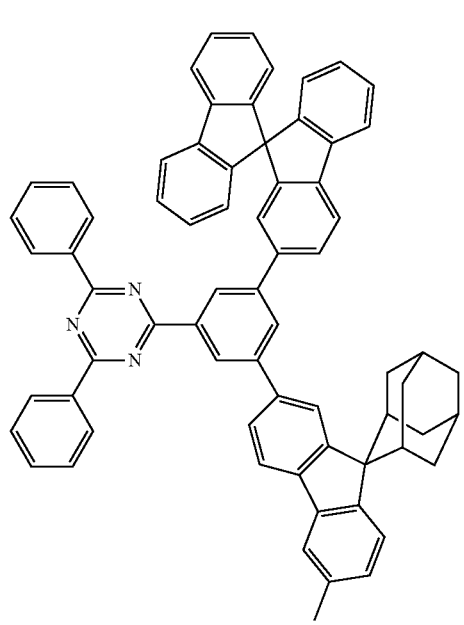
58
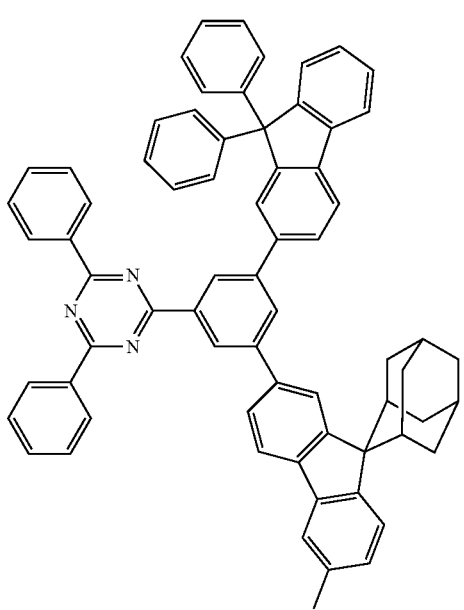
60
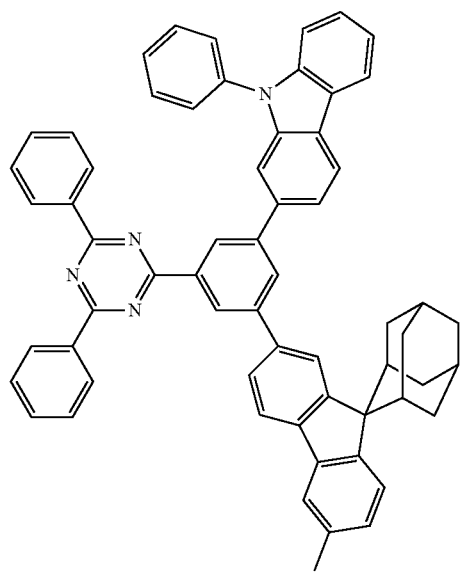

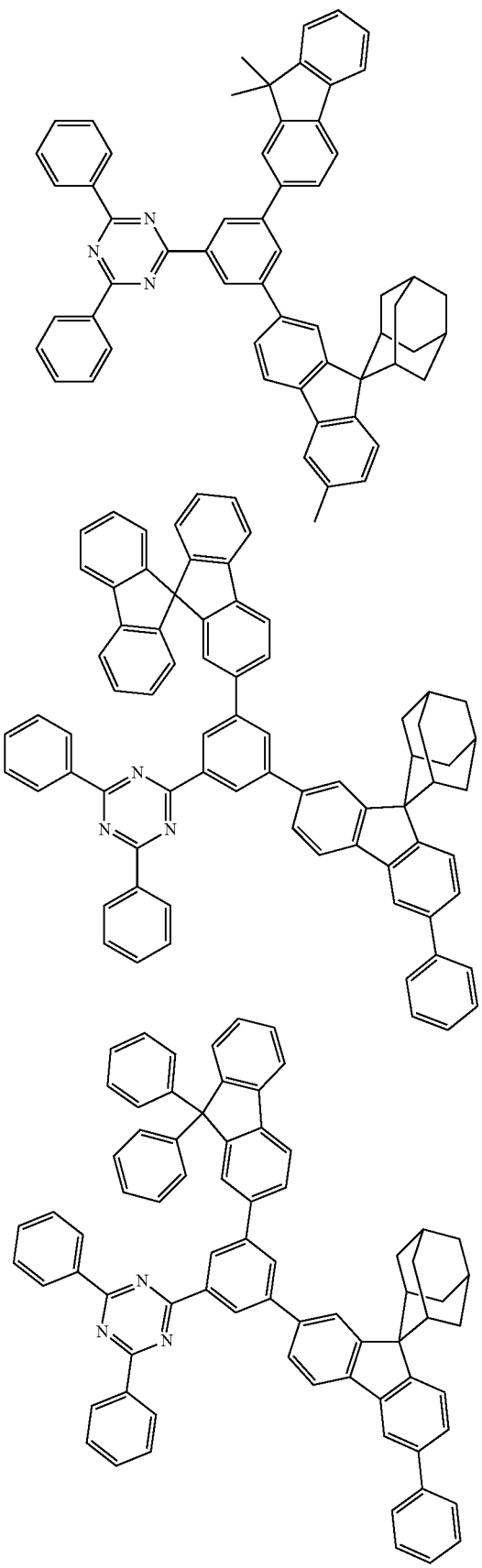
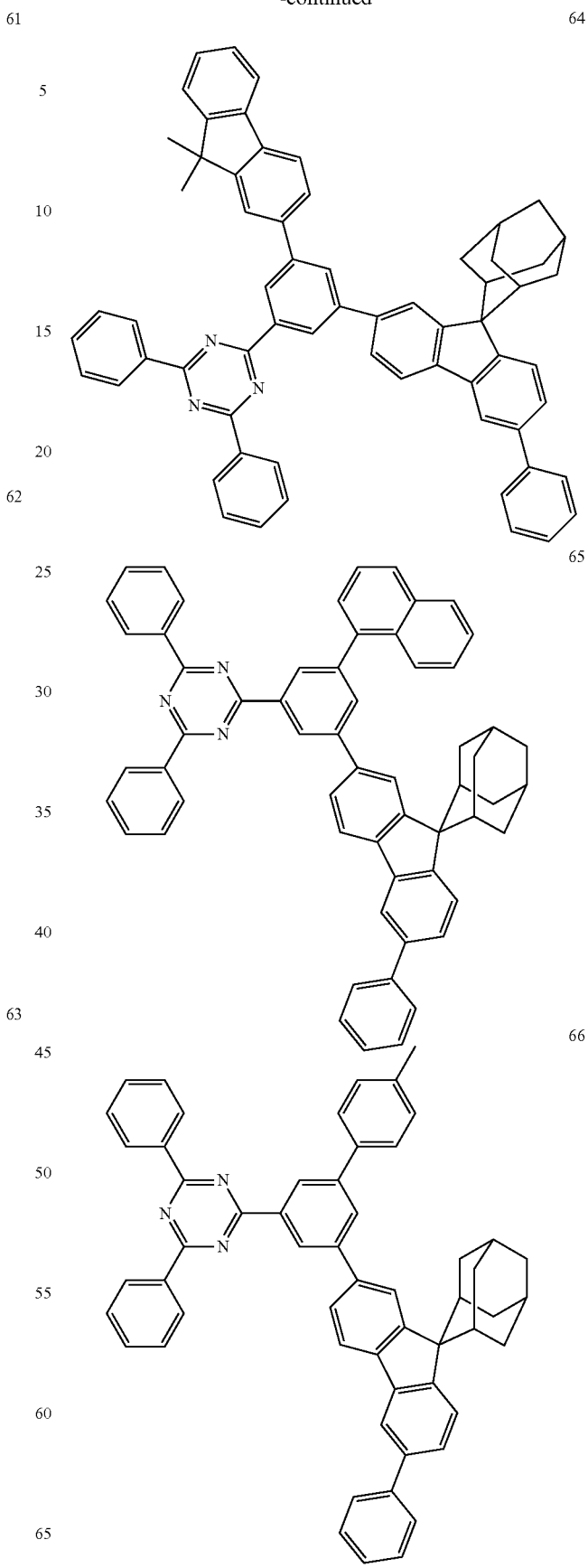

131
-continued
132
-continued
67
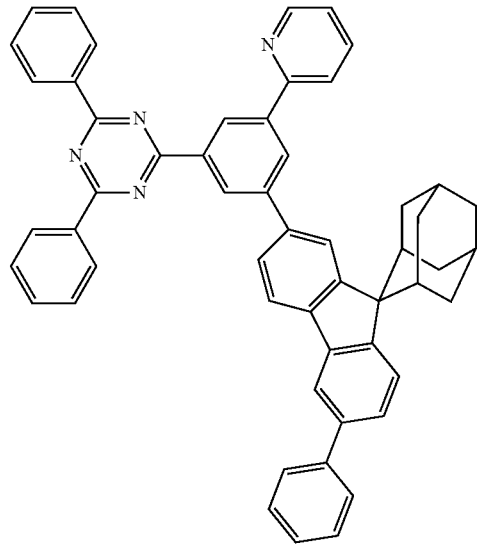
69
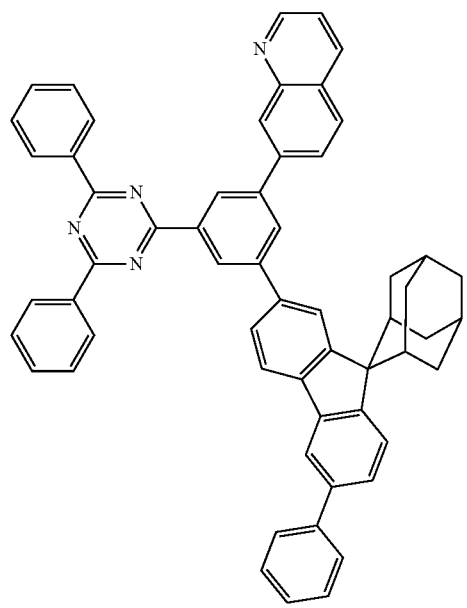
70
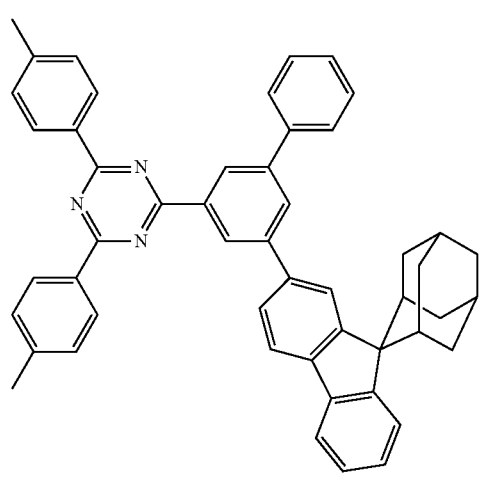
14
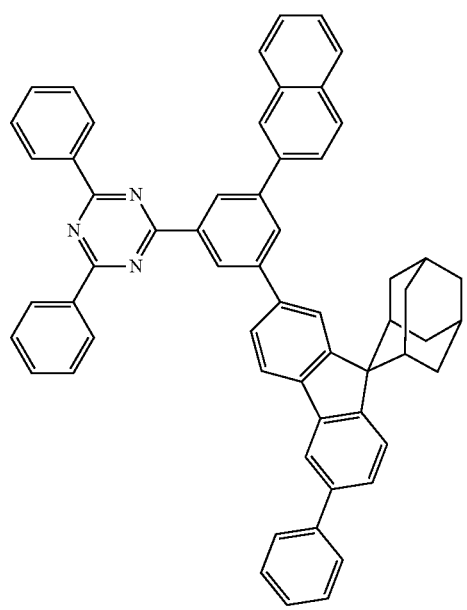
71
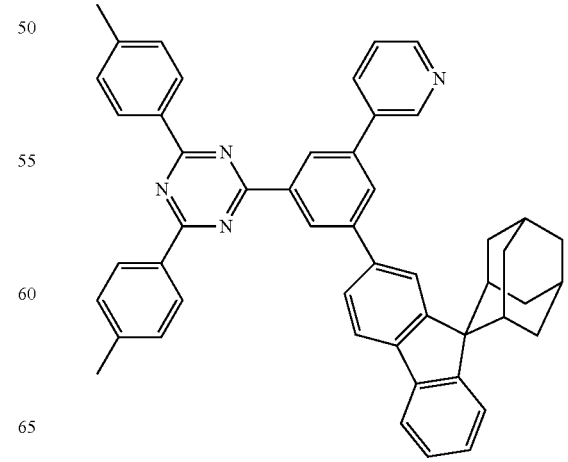

72
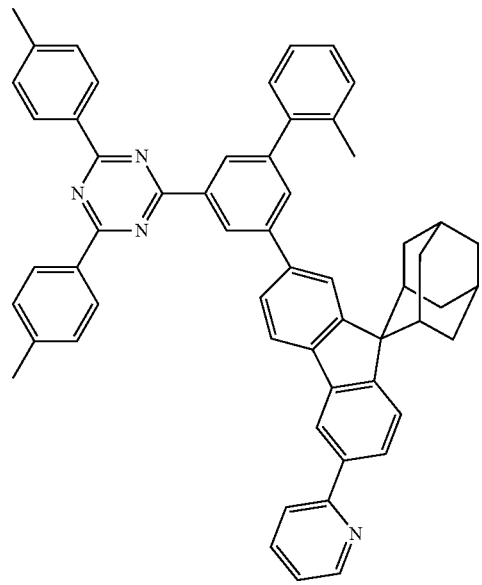
73
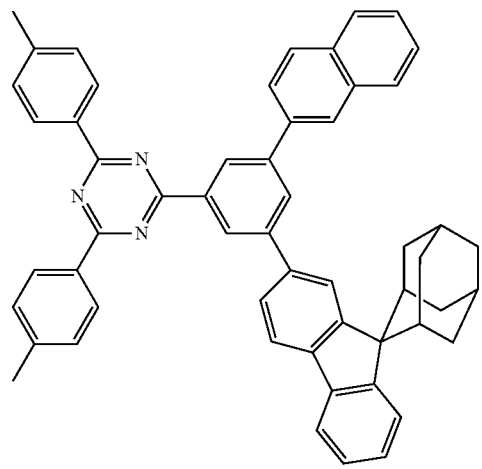
74
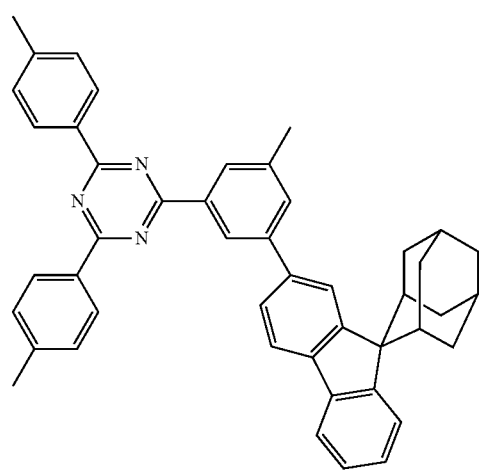
75
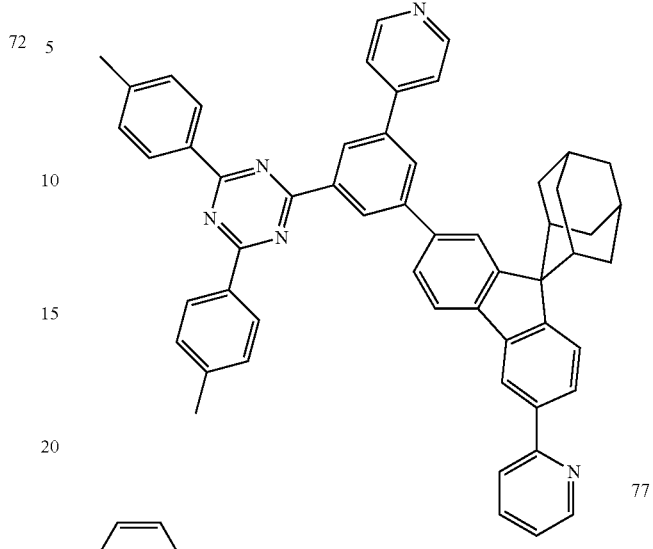
77
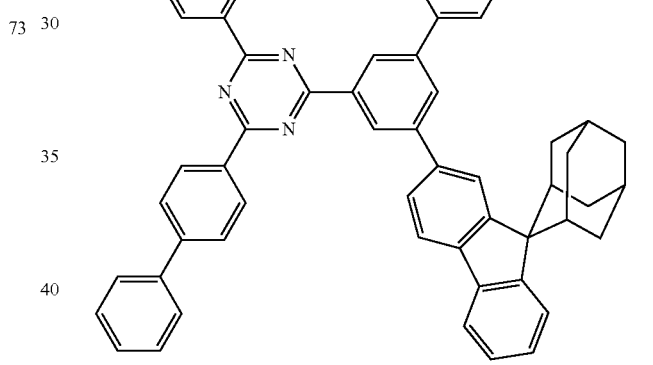
78
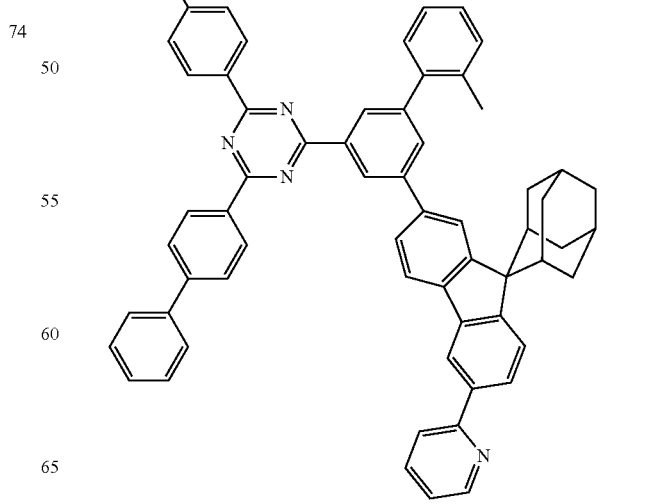

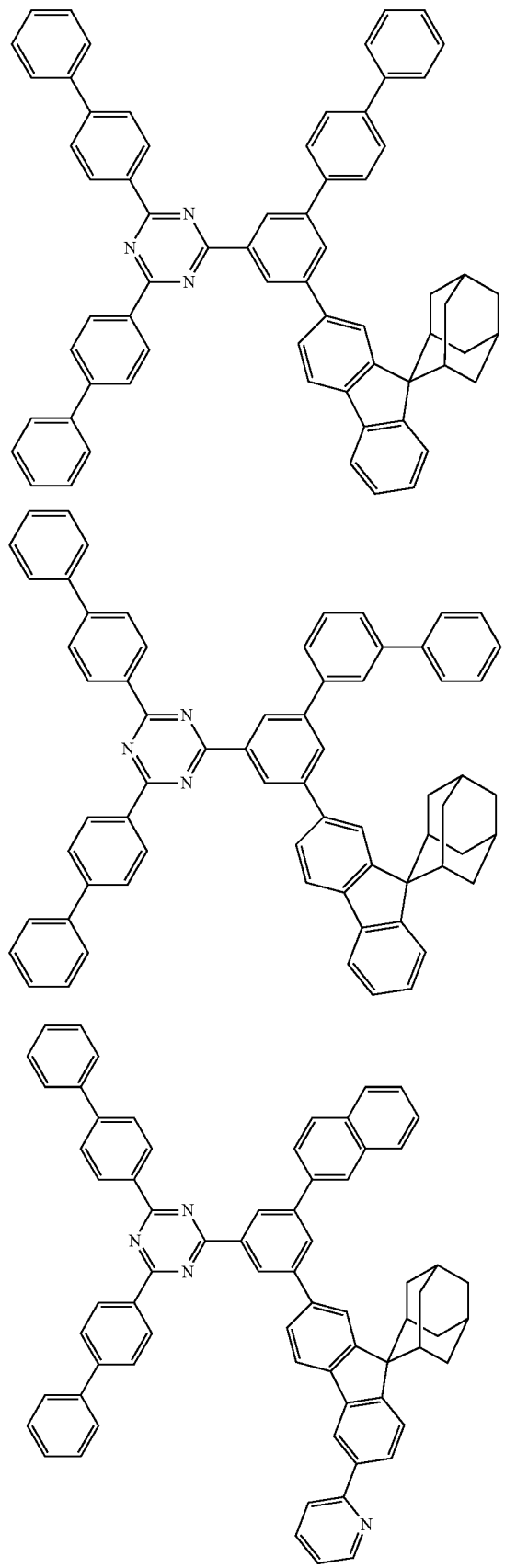
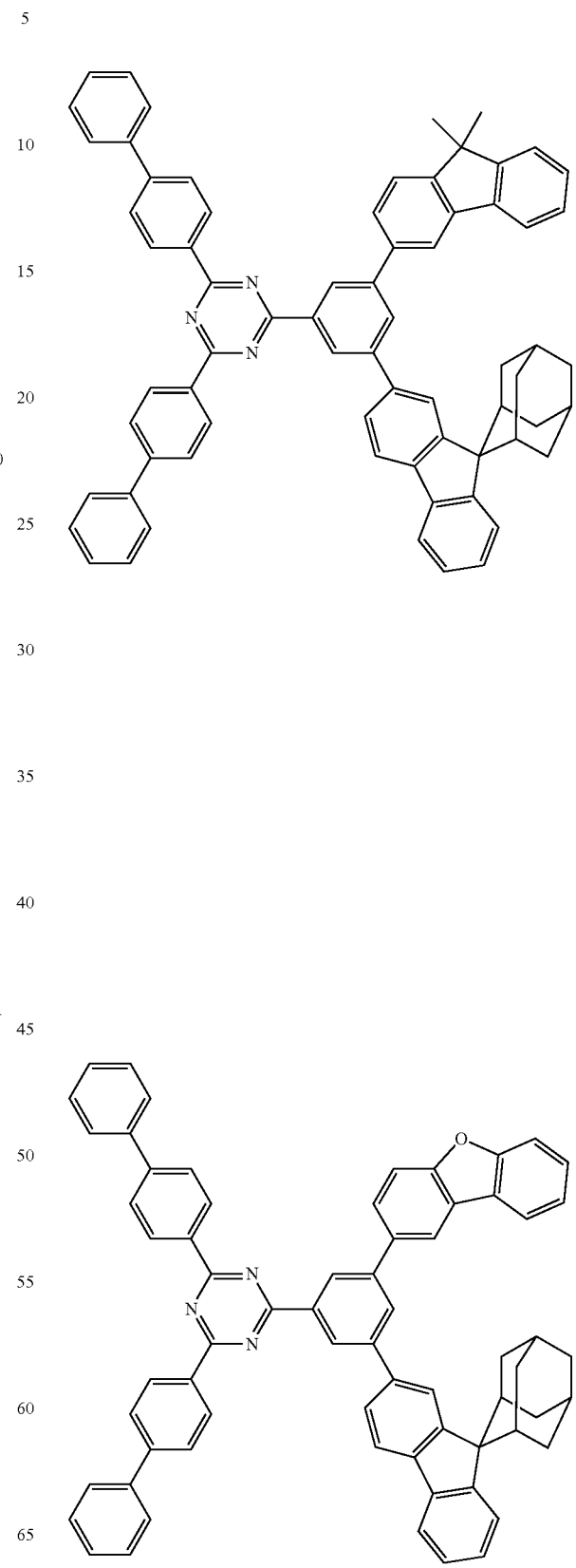

85

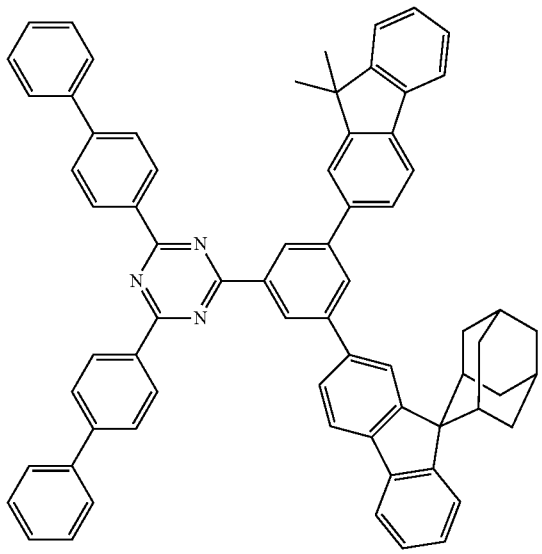

86

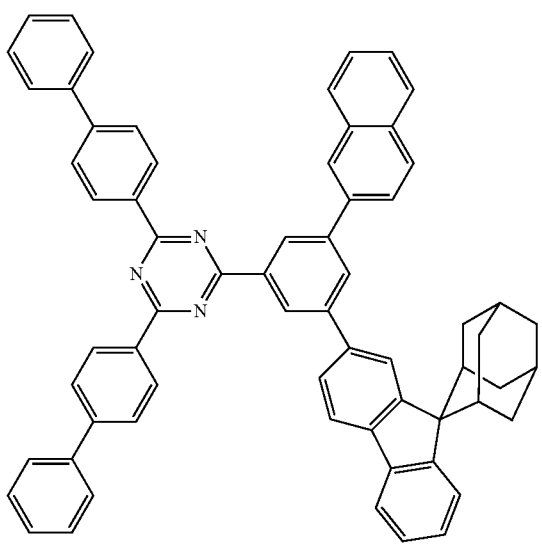

87

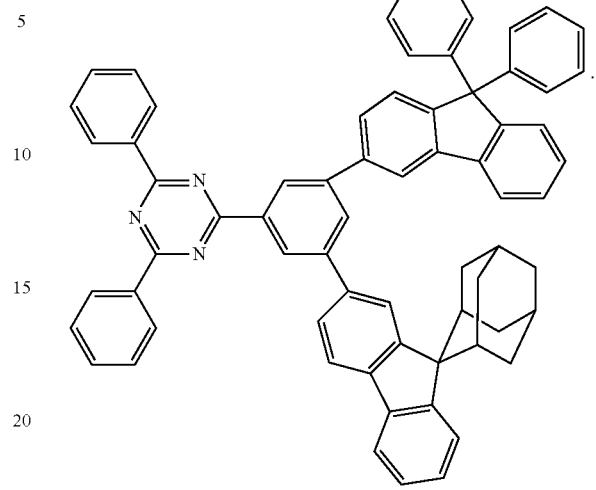

3. An electronic device, comprising a cathode, an anode and a functional layer disposed between the cathode and the anode; wherein the functional layer comprises the compound of claim 1.

4. The electronic device according to claim 3, wherein the electronic device is an organic electroluminescent device or a solar cell.

5. The electronic device according to claim 4, wherein the functional layer comprises an electron transporting layer, and the compound is included in the electron transporting layer.

6. An electronic device, comprising a cathode, an anode and a functional layer disposed between the cathode and the anode; wherein the functional layer comprises the compound of claim 2.

7. The electronic device according to claim 6, wherein the electronic device is an organic electroluminescent device or a solar cell.

* * * * *